US010266877B2

(12) United States Patent
Deng et al.

(10) Patent No.: US 10,266,877 B2
(45) Date of Patent: Apr. 23, 2019

(54) METHOD FOR SIMULTANEOUS SEQUENCE-BASED TYPING OF 14 FUNCTIONAL KILLER CELL IMMUNOGLOBULIN-LIKE RECEPTOR (KIR) GENES

(71) Applicant: SHENZHEN BLOOD CENTER, Shenzhen, Guangdong (CN)

(72) Inventors: Zhihui Deng, Guangdong (CN); Jianxin Zhen, Guangdong (CN); Guobin Zhang, Guangdong (CN)

(73) Assignee: SHENZHEN BLOOD CENTER, Shenzhen (CN)

( * ) Notice: Subject to any disclaimer, the term of this patent is extended or adjusted under 35 U.S.C. 154(b) by 0 days.

(21) Appl. No.: 15/696,120

(22) Filed: Sep. 5, 2017

(65) Prior Publication Data

US 2018/0305744 A1 Oct. 25, 2018

(30) Foreign Application Priority Data

Apr. 25, 2017 (CN) .......................... 2017 1 0284545

(51) Int. Cl.
*C12Q 1/68* (2018.01)
*C12Q 1/6811* (2018.01)
*C12Q 1/6827* (2018.01)
*C12Q 1/686* (2018.01)
*C12Q 1/6881* (2018.01)

(52) U.S. Cl.
CPC ............ *C12Q 1/6811* (2013.01); *C12Q 1/686* (2013.01); *C12Q 1/6827* (2013.01); *C12Q 1/6881* (2013.01); *C12Q 2527/107* (2013.01); *C12Q 2527/113* (2013.01); *C12Q 2527/125* (2013.01); *C12Q 2527/143* (2013.01); *C12Q 2527/146* (2013.01); *C12Q 2527/149* (2013.01); *C12Q 2600/156* (2013.01); *C12Q 2600/16* (2013.01)

(58) Field of Classification Search
None
See application file for complete search history.

(56) References Cited

FOREIGN PATENT DOCUMENTS

CN 105339508 A 2/2016

OTHER PUBLICATIONS

Belle I, Hou L, Chen M, Steiner NK, Ng J, Hurley CK. Investigation of killer cell immunoglobulin-like receptor gene diversity in KIR3DL1 and KIR3DS1 in a transplant population. Tissue Antigens. May 2008; 71(5):434-9. Epub Mar. 10, 2008. (Year: 2008).*

He YM, Tao SD, Dong LN, He J, Zhu FM. Identification of the novel KIR2DL2*00103 allele in a Chinese individual by sequence-based typing. HLA. Jun. 2016; 87(6):476-7. Epub Apr. 13, 2016. (Year: 2016).*
He Y, Tao S, Ying Y, He J, Zhu F, Lv H. Investigation of killer cell immunoglobulin-like receptors KIR2DL2 and KIR2DL3 diversity and identification of ten novel KIR2DL3 alleles in the Chinese Han population. Scand J Immunol. Apr. 2015; 81(4):265-71. (Year: 2015).*
Meenagh A, Gonzalez A, Sleator C, McQuaid S, Middleton D. Investigation of killer cell immunoglobulin-like receptor gene diversity, KIR2DL1 and KIR2DS1. Tissue Antigens. Oct. 2008; 72(4):383-91. Epub Jul. 15, 2008. (Year: 2008).*
Tao SD, He YM, Ying YL, He J, Zhu FM, Lv HJ. KIR3DL1 genetic diversity and phenotypic variation in the Chinese Han population. Genes Immun. Jan. 2014; 15(1):8-15. (Year: 2014).*
Vierra-Green et al. Allele-level haplotype frequencies and pairwise linkage disequilibrium for 14 KIR loci in 506 European-American individuals. PLoS One. 2012; 7(11):e47491 pp. 1-10. Epub Nov. 5, 2012. (Year: 2012).*
Vierra-Green et al. Estimating KIR Haplotype Frequencies on a Cohort of 10,000 Individuals: A Comprehensive Study on Population Variations, Typing Resolutions, and Reference Haplotypes. PLoS One. Oct. 10, 2016; 11(10):e0163973. pp. 1-17. (Year: 2016).*
Vilches C, Castario J, Gomez-Lozano N, Estefania E. Facilitation of KIR genotyping by a PCR-SSP method that amplifies short DNA fragments. Tissue Antigens. Nov. 2007; 70(5):415-22. Epub Sep. 14, 2007. (Year: 2007).*
Bell J. A simple way to treat PCR products prior to sequencing using ExoSAP-IT. Biotechniques. May 2008; 44(6):834. (Year: 2008).*
Cynthia Vierra-Green et al., Allele-Level Haplotype Frequencies and Pairwise Linkage Disequilibrium for 14 KIR Loci in 506 European-American Individuals, PLOS ONE, Nov. 2012, vol. 7, Issue 11.
James Robinson et al., IPD—the Immuno Polymorphism Database, Nucleic Acids Research, 2010, pp. D863-D869, vol. 38.
Colum Mcerlean et al., Differential RNA expression of KIR alleles, Immunogenetics, 2010, pp. 431-440, vol. 62, No. 7.
Makoto Yawata et al., Roles for HLA and KIR polymorphisms in natural killer cell repertoire selection and modulation of effector function, JEM, Mar. 20, 2006, pp. 633-645, vol. 203, No. 3.

(Continued)

*Primary Examiner* — Gary Benzion
*Assistant Examiner* — Olayinka A Oyeyemi

(57) ABSTRACT

Based on the structural features of KIR full genomic sequences, the distribution of single nucleotide polymorphisms in their coding regions and the length of flanking intronic sequence of each exon, a method for high-throughput simultaneous sequence-based typing of all the 14 functional killer cell immunoglobulin-like receptor (KIR) genes is disclosed including: developing a scientific and reasonable polymerase chain reaction (PCR) amplification strategy; simultaneously amplifying the complete coding sequence of each functional KIR gene using 3~5 pairs of KIR gene-specific PCR primers that have similar annealing temperature; and determining the nucleotide sequences of the exons carried by each PCR amplicon in both directions using the forward and reverse sequencing primers, respectively, as shown in FIG. 1.

7 Claims, 14 Drawing Sheets

Specification includes a Sequence Listing.

(56) References Cited

OTHER PUBLICATIONS

Marcelo J. Pando et al., The Protein Made from a Common Allele of KIR3DL1 (3DL1*004) is Poorly Expressed at Cell Surfaces due to Substitution at Positions 86 in Ig Domain 0 and 182 in Ig Domain 1, The Journal of Immunology, 2003, pp. 6640-6649, vol. 171, No. 12.

Xiaojing Bao et al., Distribution of killer cell immunoglobulin-like receptor genes and 2DS4 alleles in the Chinese Han population, Human Immunology, 2010, pp. 289-292, vol. 71, No. 3.

Tatiana V. Lebedeva et al., Comprehensive approach to high-resolution KIR typing, Human Immunology, 2007, pp. 789-796, vol. 68, No. 9.

Li-Xing Yan et al., Diversity of the killer cell immunoglobulin-like receptor gene KIR2DS4 in the Chinese population, Tissue Antigens, 2007, pp. 133-138, vol. 69, No. 2.

Stephane Buhler et al., High levels of molecular polymorphism at the KIR2DL4 locus in French and Congolese populations: Impact for anthropology and clinical studies, Human Immunology, 2009, pp. 953-959, vol. 70, No. 11.

I. Belle et al., Investigation of killer cell immunoglobulin-like receptor gene diversity in KIR3DL1 and KIR3DS1 in a transplant population, Tissue Antigens, 2008, pp. 434-439, vol. 71, No. 5.

Lihua Hou et al., Killer Cell Immunoglobulin-Like Receptors (KIR) Typing by DNA Sequencing, Methods Mol Biol., 2012, pp. 431-468, vol. 882.

A. Meenagh et al., Investigation of killer cell immunoglobulin-like receptor gene diversity, KIR2DL1 and KIR2DS1, Tissue Antigens, 2008, pp. 383-391, vol. 72, No. 4.

Zhen, Jianxin et al., Progress in research on genetic polymorphisms and sequence-based typing of KIR genes, Chin J Med Genet, Dec. 2016, pp. 867-870, vol. 33, No. 6.

Jianxin Zhen, The Molecular Genetic Polymorphism of KIR System in Southern Chinese Han Population and the Association with Leukemia, China's Outstanding Master's Degree Thesis Full-Text Database Medical and Health Science and Technology is Collected, E072-71, Dec. 15, 2014.

* cited by examiner

METHOD FOR SIMULTANEOUS SEQUENCE-BASED TYPING OF 14 FUNCTIONAL KILLER CELL IMMUNOGLOBULIN-LIKE RECEPTOR (KIR) GENES

CROSS REFERENCE TO RELATED APPLICATIONS

The present application claims priority to Chinese Patent Application No. 201710284545.3 filed on Apr. 25, 2017, the entire contents of which are incorporated herein by reference.

REFERENCE TO SEQUENCE LISTING

The substitute Sequence Listing is submitted to replace the previously submitted Sequence Listing as an ASCII formatted text filed via EFS-Web, with a file name of "Substitute_Sequence_Listing.TXT", a creation date of Sep. 14, 2017, and a size of 61,685 bytes. The substitute Sequence Listing filed via EFS-Web is part of the specification and is incorporated in its entirety by reference herein.

FIELD OF THE DISCLOSURE

The present disclosure is involved in biomedicine, and particularly gets involved in DNA sequence-based typing (SBT). The present disclosure provides a method for high-throughput simultaneous sequence-based typing of all the 14 functional killer cell immunoglobulin-like receptor (KIR) genes.

BACKGROUND OF THE DISCLOSURE

Killer cell immunoglobulin-like receptors (KIRs) belong to immunoglobulin superfamily and are expressed on both natural killer (NK) cells and a subset of T cells. Based on the number of extra-cellular domains, KIR genes are classified as KIR2D and KIR3D. Depending on the length of the cytoplasmic tail and the presence or absence of immunoreceptor tyrosine-based inhibitory motif (ITIM), KIRs can be functionally divided into inhibitory KIR (iKIR) and activating KIR (aKIR). KIR receptors regulate NK cell activities and convey activating or inhibitory signal through interaction with class I human leukocyte antigen (HLA) ligands, which play an important role in transplantation, elimination of tumor cells and resistance to viral infection through innate immune pathways.

The KIR gene cluster on human chromosome 19 consists of 14 functional KIR genes (KIR2DL1, 2DL2, 2DL3, 2DL4, 2DL5, 2DS1, 2DS2, 2DS3, 2DS4, 2DS5, 3DL1, 3DL2, 3DL3, 3DS1) and two pseudogenes (KIR2DP1 and 3DP1) (1). The structure of KIR genes is extremely complicated. Except that KIR3DL3 lacks exon 6, other functional KIR3D genes including 3DL1, 3DL2, and 3DS1 possess 9 exons, 8 introns, a 5'-promoter region and a 3'-untranslated region (3'-UTR). Exons 1 and 2 encode leader peptide. Exons 3, 4 and 5 encode the extra-cellular domains D0, D1 and D2, respectively. Exon 6 encodes the stem. Exon 7 encodes the transmembrane region. Exons 8 and 9 encode the cytoplasmic region. Among the KIR2D genes, KIR2DL1~3 and 2DS1~5 have an untranslated pseudoexon 3, which results in the absence of the corresponding extra-cellular domain D0. KIR2DL4 and 2DL5 are characterized by the complete absence of exon 4, and therefore their protein product has no extra-cellular domain D1.

The full genomic sequences for all the KIR alleles released in the IPD-KIR database varies from 9901 bp to 17009 bp in size (2). However, the coding sequences (CDS) of each functional KIR gene has a total length of only 915~1368 bp (see Table 3), which imply that the non-coding sequence (8773~15641 bp) accounts for the majority of full genomic sequences of KIR gene (see Table 4). Particularly, the length of introns 5 and 6 accounts for 44.0%~61.2% of the full genomic sequence of corresponding KIR gene (also see Table 4).

Both exon 1 (either 34 or 40 bp) and exon 2 (36 bp) of each functional KIR gene are short in length and have limited single nucleotide polymorphism sites (SNPs). KIR2DL2, 2DL4 and 2DS4 lack SNPs in both exons 1 and 2, whereas other functional KIR genes possess 1~3 SNPs, respectively. Thus, routine sequence-based typing at exons 1 and 2 is not required for each KIR gene. In addition, intron 1, which is located between exon 1 and exon 2, is 199~2280 bp in length. Polymerase chain reaction (PCR) amplicon covering the entire exon 1, exon 2 and the intervening intron 1 will be moderate in length for each KIR gene and can be amplified effectively.

Exon 3, exon 4 or exon 5 of each functional KIR gene is relatively long in length (282~300 bp) and has much SNPs. Since pseudoexon 3 for KIR2DL1~3 and 2DS1~5 doesn't required to be detected, PCR amplification covering the entire exon 4, intron 4 and exon 5 can be achieved in a single amplicon using one pair of KIR gene-specific PCR primers, and then sequencing of exons 4 and 5 needs to be performed separately in both directions for these 8 functional KIR genes. Likewise, both KIR2DL4 and 2DL5 miss exon 4, PCR amplication covering the entire exon 3, intron 3/4 and exon 5 can be achieved in a single amplicon using one pair of KIR gene-specific PCR primers and then sequencing of exons 3 and 5 needs to be performed separately in both directions. As for the other four functional KIR genes (KIR3DS1, 3DL1~3), which all possess exons 3, 4 and 5, the PCR amplication covering the entire exon 3, intron 3, exon 4, intron 4 and exon 5 can be achieved in a single amplicon using one pair of KIR gene-specific primers and then the sequencing of exons 3, 4 and 5 needs to be performed separately in both directions.

Apart from KIR3DL3 without exon 6, the exon 6 of all the other functional KIR genes is only 51 bp in length. According to the IPD-KIR Database (Release 2.6.0), KIR2DS4, 3DL1, 3DL2, and 3DS1 genes lack SNPs in exon 6, other functional KIR genes possess 1~2 SNPs. The distribution of SNPs located in exon 6 of each KIR gene is limited. However, the flanking intronic sequences of exon 6 which include introns 5 and 6 have a total length of up to 4937~9841 bp (see Table 4). To ensure the effective PCR amplication, the entire intronic sequences of intron 5 and/or intron 6 should be avoided in case of generating extreme long PCR amplicon. Thus, the target sequence of exon 6 for each KIR gene should be amplified separately in a single amplicon if necessary.

The length for exons 7, 8 and 9 of each functional KIR gene is 102~105 bp, 51~53 bp and 8~270 bp, respectively. The length for introns 7 and 8 is 460~462 bp and 98~118 bp, respectively. Therefore, PCR amplification covering entire exon 7, intron 7, exon 8, intron 8, and exon 9 can be performed in a single amplicon and will not generate ultra-long PCR fragment.

The structural features of full genomic sequence for all functional KIR genes, the characteristic of SNPs distribution in coding sequence and the length of each exon and its flanking intronic sequence that we have mentioned above, are critical to develop a scientific and efficient PCR amplification strategy.

KIR genes exhibit extensive diversity in both haplotype content and allelic diversification. So far 698 KIR alleles including 7 null alleles have been released in the IPD-KIR Database (Release 2.6.0). Among the 14 functional KIR genes, KIR3DL2 exhibits the highest level of allelic diversity with 112 different identified alleles (see Table 5).

Identification of KIR alleles can carry functional significance. McErlean et al. (3) have found that mRNA expression level for the 14 functional KIR genes varies with the hierarchy KIR3DL2>KIR2DS2>KIR3DS1>KIR2DS5> KIR2DL5>KIR2DS3>KIR2DL1>KIR3DL1>KIR2DS1> KIR2DL2>KIR2DL4>KIR2DS4>KIR2DL3. Even within the same KIR gene, the expression level on NK cell surface, the affinity to cognate ligand and the capacity of medicated inhibition or activation can be influenced by different allele. It has been reported by Yawata et al. (4) that the expression levels of KIR3DL1 alleles were in the order of KIR3DL1*01502>*020>*001>*007>*005, whereas the levels of 3DL1-mediated NK cell inhibition were in the order of KIR3DL1*001>*005>*01502>*020>*007. KIR3DL1*005 combines low cell surface expression with a high inhibitory capacity. KIR3DL1*004, a most common KIR3DL1 allele in Caucasians, is poorly expressed at the cell surface (5). KIR2DS4*003, *004, *006, *007, *008, *009, *010, *012, and *013 alleles have a 22 bp deletion at coding sequence (CDS) nucleotide position nt454~nt475 in exon 5, which causes a reading frame shift, yielding a truncated KIR2DS4 protein with loss of the transmembrane and cytoplasmic domains. These deleted variants of KIR2DS4 protein can't be anchored to the cell surface (6). Thus, it is critical important to identify allelic variation within the 14 functional KIR genes, especially those common null alleles. Since KIR allelic variation alters the level of protein expression and the affinity for cognate ligand as well as the mediated inhibitory/activating capacity, it is an urgent task to develop a low-cost, high-throughput, simultaneous sequence-based typing (SBT) method and apply the established SBT method in KIR-associated disease studies.

To date, the widely-used polymerase chain reaction-sequence specific primer (PCR-SSP) and PCR-sequence specific oligonucleotide probe (PCR-SSOP) commercial kits can only identify the presence or absence of KIR genes on low-resolution level, but can not identify all the KIR alleles at the allele level, especially for those null alleles.

Sequence-based typing is a powerful technique for KIR genotyping at allele level. However, there are no commercial KIR SBT kit and corresponding software for KIR allele assignment in worldwide until now. As KIR genes share extensive sequence homology, it is difficult to design KIR gene-specific primers for PCR amplification of target sequences. While summarizing the characteristic of the KIR SBT methods in the previously published literatures, several problems existed in: ① Only exons encoding extra-cellular domains and/or cytoplasmic region were sequenced for some KIR genes (7, 8, 9). Since the entire coding sequence was not sequenced and the diversity of each exon could not be allowed for analyzing, which led to being prone to generate ambiguous allele combination in SBT test. ② The PCR amplicons could cover the entire coding sequence of each KIR gene, however, the fragments size of PCR amplicon were extremely too long. For example, the KIR3DS1 amplicon covering exon 3 through 3' untranslated region (3'-UTR) generated a fragment of approximate 12.2 kb in length, and PCR extension at 68V required up to 13 min in each cycle (10), as a result the total PCR amplification time exceeded 10 hours, more high requirement for DNA quality as well as the high-fidelity DNA polymerase were needed in PCR amplification. ③ As KIR genes share extensive sequence homology, non-specific amplification or co-amplification occurred in PCR procedure. e.g., while amplifying the target sequence covering exon 1 through exon 5 of 2DL1 in a subject carrying both 2DL1 and 2DS1 genes, 2DS1 would also be co-amplified (11). To obtain 2DL1 specific PCR products, the secondary amplification needed to be carried out using nested PCR primers, which made the PCR procedure cumbersome. ④ Due to the different annealing temperatures for PCR primers and varied extension time in each PCR cycling, PCR amplifications could not be carried out simultaneously under the same thermocycling parameters while amplifying the target sequences of 14 functional KIR genes (10, 11, 12, 13), which made PCR procedure more time-consuming and labour-consuming. ⑤ Identification of the KIR alleles with one or more base pair insertion/deletion by traditional cloning and sequencing could not allow for the desired rapidity and simplicity in routine KIR genotyping.

With the elucidation of biological functions for KIR molecules, the clinical significance of the increasingly recognized KIR polymorphism and its role played in transplantation and disease associated studies have drawn extensive interest. Therefore, establishment of the method for high-throughput simultaneous sequence-based typing of 14 functional KIR genes, together with its commercialization and industrialization are currently urgent problems to be solved.

SUMMARY OF THE DISCLOSURE

The present disclosure aims to solve the problems mentioned above and for the first time provide a simultaneous sequence-based typing (SBT) method for all the 14 functional KIR genes. The established KIR SBT method can be widely-used in population genetics, tissue typing for bone marrow transplantation, disease-associated studies, and also lays the foundation for the commercialization of KIR SBT reagents, which change the current status that no available commercial KIR SBT reagents meet the marketing.

In order to achieve the above objective, the present disclosure adopts the following technical strategy:

I. Based on the structural features of KIR full genomic sequences, the distribution of single nucleotide polymorphisms in their coding regions and the length of flanking intronic sequence of each exon, a scientific and reasonable PCR amplification strategy has been developed in the present disclosure. The complete coding sequence of each functional KIR gene is simultaneously amplified under the same thermocycling parameters using 3~5 pairs of KIR gene-specific PCR primers that have similar annealing temperature. The nucleotide sequences of the exons carried by each PCR amplicon were determined in both directions using the specific forward and reverse sequencing primers, respectively, as shown in FIG. 1.

The coding sequence of KIR2DL1 is amplified using 5 pairs of KIR2DL1 gene-specific PCR primers. In particular, the first pair of PCR primers is used to amplify the target sequence of KIR2DL1 covering exon 1, intron 1, exon 2, partial sequences of 5'-promoter region and intron 2/3; the second pair of PCR primers is used to amplify the target sequence of KIR2DL1 covering exon 4 and its partial flanking intronic sequences; the third pair of PCR primers is used to amplify the target sequence of KIR2DL1 covering exon 5 and its partial flanking intronic sequences; the fourth pair of PCR primers is used to amplify the target sequence of KIR2DL1 covering exon 6 and partial flanking intronic sequences; the fifth pair of PCR primers is used to amplify the target sequence of KIR2DL1 covering exon 7, intron 7, exon 8, intron 8, exon 9, partial sequences of intron 6 and 3'-UTR region.

The coding sequences of KIR2DL2, 2DL3, 2DS1, 2DS2, 2DS3, 2DS4 and 2DS5 are amplified using 4 pairs of KIR gene-specific PCR primers, respectively. The first pair of PCR primers is used to amplify the target sequence of each KIR gene mentioned above covering exon 1, intron 1, exon 2, partial sequences of 5'-promoter region and intron 2/3 (since exon 3 is a pseudoexon, the sequence between exon 2 and exon 4 is referred as intron 2/3); the second pair of PCR primers is used to amplify the target sequence of each KIR gene mentioned above covering exon 4, intron 4, exon 5, partial sequences of intron 2/3 and intron 5; the third pair of PCR primers is used to amplify the target sequence of each KIR gene mentioned above covering exon 6 and partial flanking intronic sequences; the fourth pair of PCR primers is used to amplify the target sequence of each KIR gene mentioned above covering exon 7, intron 7, exon 8, intron 8, exon 9, partial sequences of intron 6 and 3'-UTR region.

The coding sequences of KIR2DL4 and KIR2DL5 are amplified using 4 pairs of corresponding KIR gene-specific PCR primers, respectively. The first pair of PCR primers is used to amplify the target sequence of each KIR gene mentioned above covering exon 1, intron 1, exon 2, partial sequences of 5'-promoter region and intron 2; the second pair of PCR primers is used to amplify the target sequence of covering exon 3, intron 3/4 (since exon 4 is deleted, the sequence between exon 3 and exon 5 is referred to as intron 3/4), exon 5, partial sequences of intron 2 and intron 5; the third pair of PCR primers is used to amplify the target sequence of each KIR gene mentioned above covering exon 6 and partial flanking intronic sequences; the fourth pair of PCR primers is used to amplify the target sequence of each KIR gene mentioned above covering exon 7, intron 7, exon 8, intron 8, exon 9, partial sequences of intron 6 and 3'-UTR region.

The coding sequences of KIR3DL1, 3DL2 and 3DS1 are amplified using 4 pairs of corresponding KIR gene-specific PCR primers, respectively. The first pair of PCR primers is used to amplify the target sequence of each KIR gene mentioned above covering exon 1, intron 1, exon 2, partial sequences of 5'-promoter region and intron 2; the second pair of PCR primers is used to amplify the target sequence of each KIR gene mentioned above covering exon 3, intron 3, exon 4, intron 4, exon 5, partial sequence of intron 2 and intron 5; the third pair of PCR primers is used to amplify the target sequence of each KIR gene mentioned above covering exon 6 and partial flanking intronic sequences; the fourth pair of PCR primers is used to amplify the target sequence of each KIR gene mentioned above covering exon 7, intron 7, exon 8, intron 8, exon 9, partial sequences of intron 6 and 3'-UTR region.

Since KIR3DL3 lacks exon 6, only 3 pairs of KIR3DL3 specific PCR primers are used to amplify the coding sequence of KIR3DL3. The first pair of PCR primers is used to amplify the target sequence of KIR3DL3 covering exon 1, intron 1, exon 2, partial sequences of 5'-promoter and intron 2; the second pair of PCR primers is used to amplify the target sequence of KIR3DL3 covering exon 3, intron 3, exon 4, intron 4, exon 5, partial sequences of intron 2 and intron 5/6; the third pair of PCR primers is used to amplify the target sequence of KIR3DL3 covering exon 7, intron 7, exon 8, intron 8, exon 9, partial sequences of intron 5/6 and 3'-UTR region.

II. The coding sequences of 14 functional KIR genes are amplified using a total of 56 pairs of KIR gene-specific PCR primers. Except that only three pairs of PCR primers are used for KIR3DL3 and five pairs of PCR primers are used for KIR2DL1, four pairs of KIR gene-specific PCR primers are used for each other functional KIR gene. All the PCR primers are designed using the Primer Premier 5.0 software and have been examined using NCBI BLAST to confirm homology with the expected KIR gene. The sequence of each PCR primer, its position in the full genomic sequence and the length of each PCR amplicon are illustrated in Table 1.

TABLE 1

KIR gene-specific PCR primers for 14 functional KIR genes

| KIR Gene | PCR Primer Name | Direction | SEQ ID No | Primer Sequence (5'→3') | Position in the full genomic sequence | Length of Amplicon (bp) |
|---|---|---|---|---|---|---|
| 2DL1 | 2DL1_PCR_Ex12_F | Forward | 1 | GTTCGGGAGGTTGGATCTC | nt-268~nt-250 | 1618 |
|  | 2DL1_PCR_Ex12_R | Reverse | 2 | CACACTGCAGCCCCTACCG | nt1332~nt1350 |  |
|  | 2DL1_PCR_Ex4_F | Forward | 3 | TGATTCTCCTGAGTCTCCAGAGG | nt2501~NT2523 | 2810 |
|  | 2DL1_PCR_Ex4_R | Reverse | 4 | TGGAAGGAGAAGAGGCAGTTTCC | nt5288~nt5310 |  |
|  | 2DL1_PCR_Ex5_F | Forward | 5 | CTGGCAGGGACCTACAGATGC | nt3692~nt3712 | 1937 |
|  | 2DL1_PCR_Ex5_R | Reverse | 6 | GGACAGCCATGGGCTTTCCTC | nt5608~nt5628 |  |
|  | 2DL1_PCR_Ex6_F | Forward | 7 | TCCTGATTGTGAGTTCTTGGCAT | nt8082~nt9301 | 1220 |
|  | 2DL1_PCR_Ex6_R | Reverse | 8 | TGAGTCAGTSAGTCGAARTGTGC | nt9279~nt9301 |  |
|  | 2DL1_PCR_Ex789_F | Forward | 9 | CCTCAGCACGTTCTATGGTTACT | nt12880~nt12902 | 1392 |
|  | 2DL1_PCR_Ex789_R | Reverse | 10 | TGTGATTGCAGCCTCAAGTAGAC | nt14249~nt14271 |  |
| 2DL2 | 2DL2_PCR_Ex12_F | Forward | 11 | AGAGGTTGGATCTGAGACGTC | nt-263~nt-243 | 3873 |

TABLE 1-continued

KIR gene-specific PCR primers for 14 functional KIR genes

| KIR Gene | PCR Primer Name | Direction | SEQ ID No | Primer Sequence (5'→3') | Position in the full genomic sequence | Length of Amplicon (bp) |
|---|---|---|---|---|---|---|
| | 2DL2_PCR_Ex12_R | Reverse | 12 | GGACCGATGGAGAAGTTGGCT | nt3590~nt3610 | |
| | 2DL2_PCR_Ex45_F | Forward | 13 | GAGGCTACTAGAGACAGAGGGAC | nt3207~nt3229 | 2431 |
| | 2DL2_PCR_Ex45_R | Reverse | 14 | CCCAAGCTTCGTCTTCTCTCT | nt5617~nt5637 | |
| | 2DL2_PCR_Ex6_F | Forward | 15 | CATGCCAACATCATGCTGTC | nt8530~nt8549 | 1370 |
| | 2DL2_PCR_Ex6_R | Reverse | 16 | TCCCTGTCCTAGCCTCCATAC | nt9879~nt9899 | |
| | 2DL2_PCR_Ex789_F | Forward | 17 | GAAGTTCCACTTGCCAAGGAATG | nt9210~nt9232 | 4882 |
| | 2DL2_PCR_Ex789_R | Reverse | 18 | CAGCTGCTGGTACATGGGAGC | nt14071~nt14091 | |
| 2DL3 | 2DL3_PCR_Ex12_F | Forward | 19 | GGCYGMCTGTCTGCACAGA | nt-26~nt-8 | 2606 |
| | 2DL3_PCR_Ex12_R | Reverse | 20 | GGTTTCCTGTTGCTGCTGTAG | nt2560~nt2580 | |
| | 2DL3_PCR_Ex45_F | Forward | 21 | AGAGAAGAGGGAGGGAGACAGAT | nt3231~nt3253 | 2439 |
| | 2DL3_PCR_Ex45_R | Reverse | 22 | GCCATCCTGTGCCCTGATC | nt5651~nt5669 | |
| | 2DL3_PCR_Ex6_F | Forward | 23 | CCCACCTCAGGCTCTCAAAGG | nt7497~nt7517 | 1432 |
| | 2DL3_PCR_Ex6_R | Reverse | 24 | GGCGTACAATGTCAGAGCTGC | nt8908~nt8928 | |
| | 2DL3_PCR_Ex789_F | Forward | 25 | ACTGAGAAAGCAGGAGAAAGCTG | nt12934~nt12956 | 1150 |
| | 2DL3_PCR_Ex789_R | Reverse | 26 | CCTTCAGATTCCAGCTGCTGG | nt14063~nt14083 | |
| 2DL4 | 2DL4_PCR_Ex12_F | Forward | 27 | GTGGTCAATGTGTCAACTGCACG | nt-99~nt-77 | 1760 |
| | 2DL4_PCR_Ex12_R | Reverse | 28 | CACAGGCTCCAAGGATTACAATG | nt1639~nt1661 | |
| | 2DL4_PCR_Ex35_F | Forward | 29 | CTTTCTTCCCCATGGCTGAGTTG | nt571~nt593 | 3300 |
| | 2DL4_PCR_Ex35_R | Reverse | 30 | CTTGGGCAACAAGAGTGAAACGC | nt3848~nt3870 | |
| | 2DL4_PCR_Ex6_F | Forward | 31 | AACCTCTACCTCCAGGATTCAAG | nt3904~nt3926 | 1857 |
| | 2DL4_PCR_Ex6_R | Reverse | 32 | GTAAGTGGAAGTGTCATGTGCAC | nt5738~nt5760 | |
| | 2DL4_PCR_Ex789_F | Forward | 33 | CCAAGAAATGAGAGACAATCCAC | nt9442~nt9464 | 1119 |
| | 2DL4_PCR_Ex789_R | Reverse | 34 | AGGCACCAGATTTGTGGTGTG | nt10540~nt10560 | |
| 2DL5 | 2DL5_PCR_Ex12_F | Forward | 35 | TCATAGTGAAGGACGYGAGGTGC | nt-230~nt-208 | 1490 |
| | 2DL5_PCR_Ex12_R | Reverse | 36 | AGCCAATGTGTGAACCACAATAC | nt1238~nt1260 | |
| | 2DL5_PCR_Ex35_F | Forward | 37 | CAGGACAAGCCCTTGCTGTCT | nt1571~nt1591 | 1445 |
| | 2DL5_PCR_Ex35_R | Reverse | 38 | GACAGAAACAAGCAGTGGGTCAC | nt2993~nt3015 | |
| | 2DL5_PCR_Ex6_F | Forward | 39 | CATTTCCTCACCTCTCTCCTGTCCT | nt5158~nt5182 | 1216 |
| | 2DL5_PCR_Ex6_R | Reverse | 40 | AAGAGCAGAGGCCAAATGCATCG | nt6451~nt6373 | |
| | 2DL5_PCR_Ex789_F | Forward | 41 | CAGATGTTGTATGTGCTTAGCTG | nt7907~nt7929 | 1053 |
| | 2DL5_PCR_Ex789_R | Reverse | 42 | GGTTTTGAGACAGGGCTGTTGTC | nt8937~nt8959 | |
| 2DS1 | 2DS1_PCR_Ex12_F | Forward | 43 | CATAGTGAAGGACGCTAGGTGTA | nt-229~nt-207 | 2284 |
| | 2DS1_PCR_Ex12_R | Reverse | 44 | GAGCCCTCTGACCTGTGACCG | nt2035~nt2055 | |
| | 2DS1_PCR_Ex45_F | Forward | 45 | GTTCCTCTTCCACCCCCACAC | nt3175~nt3195 | 2595 |

TABLE 1-continued

KIR gene-specific PCR primers for 14 functional KIR genes

| KIR Gene | PCR Primer Name | Direction | SEQ ID No | Primer Sequence (5'→3') | Position in the full genomic sequence | Length of Amplicon (bp) |
|---|---|---|---|---|---|---|
| | 2DS1_PCR_Ex45_R | Reverse | 46 | GAGGGTTTGGAGGTGCCCTGTCG | nt5747~nt5769 | |
| | 2DS1_PCR_Ex6_F | Forward | 47 | TCCTGATTGTGAGTTCTTGGCAT | nt8078~nt8100 | 2687 |
| | 2DS1_PCR_Ex6_R | Reverse | 48 | GTCTCCTAGATTCCAGTTACGCC | nt10742~nt10764 | |
| | 2DS1_PCR_Ex789_F | Forward | 49 | CGTGGAAAAGGCAATTCCCGA | nt10765~nt10785 | 3586 |
| | 2DS1_PCR_Ex789_R | Reverse | 50 | GGAGGTGGAACAGCACGTGTC | nt14330~nt14350 | |
| 2DS2 | 2DS2_PCR_Ex12_F | Forward | 51 | TGAGAGGTTGGATCTGAGACGTC | nt-265~nt-243 | 3243 |
| | 2DS2_PCR_Ex12_R | Reverse | 52 | ACATCCAGGCTCTTATCAGCCTT | nt2956~nt2978 | |
| | 2DS2_PCR_Ex45_F | Forward | 53 | GCTTCCATGCTTCTGATAATTTTG | nt2420~nt2443 | 3240 |
| | 2DS2_PCR_Ex45_R | Reverse | 54 | CTCTGGGTCTCTCCTGACCGT | nt5639~nt5659 | |
| | 2DS2_PCR_Ex6_F | Forward | 55 | CATTCTGCTCCGTTGTTCTATGTC | nt8282~nt8305 | 765 |
| | 2DS2_PCR_Ex6_R | Reverse | 56 | GCCAGGGTTGCTTCATGACCTAT | nt9024~nt9046 | |
| | 2DS2_PCR_Ex789_F | Forward | 57 | GATAGGCCATGGGGAGGTAAAYT | nt11463~nt11485 | 2811 |
| | 2DS2_PCR_Ex789_R | Reverse | 58 | GGGCAGACATGTTTATTTGAAGGC | nt14250~nt14273 | |
| 2DS3 | 2DS3_PCR_Ex12_F | Forward | 59 | TGTAAACTGCATGGGCAGGGA | nt-90~nt-70 | 2480 |
| | 2DS3_PCR_Ex12_R | Reverse | 60 | CTCTGACCTGTGACCATGATCAG | nt2368~nt2390 | |
| | 2DS3_PCR_Ex45_F | Forward | 61 | CTGAGCCCAGCGGCAAGGC | nt3586~nt3604 | 2474 |
| | 2DS3_PCR_Ex45_R | Reverse | 62 | ATCCCTCCCTCACACCGAGGA | nt6039~nt6059 | |
| | 2DS3_PCR_Ex6_F | Forward | 63 | TACCAGGGTTCTCCTTTCTCTAG | nt7491~nt7513 | 2406 |
| | 2DS3_PCR_Ex6_R | Reverse | 64 | AGGAAGGGGACCAGGAGCG | nt9878~nt9896 | |
| | 2DS3_PCR_Ex789_F | Forward | 65 | TGATGTTGAAGGAAGAGGCTCTT | nt10853~nt10875 | 3859 |
| | 2DS3_PCR_Ex789_R | Reverse | 66 | GATAGTCTGAGGGGAGGTGGAACT | nt14688~nt14711 | |
| 2DS4 | 2DS4_PCR_Ex12_F | Forward | 67 | ACCATGTCGCTCATGGTCATCAT | nt3~nt20 | 3093 |
| | 2DS4_PCR_Ex12_R | Reverse | 68 | TTGTCCTGACCACCTTGGGGT | nt3070~3090 | |
| | 2DS4_PCR_Ex45_F | Forward | 69 | TCAGTTCATACCTCCTGCCAAGG | nt4419~nt4441 | 3213 |
| | 2DS4_PCR_Ex45_R | Reverse | 70 | CGTGGTCAGGAGTTCCAGAGC | nt7611~nt7631 | |
| | 2DS4_PCR_Ex6_F | Forward | 71 | CTGGACTCCCAGGGCCCAATG | nt10004~nt10024 | 229 |
| | 2DS4_PCR_Ex6_R | Reverse | 72 | AAGGTTTCCACCTCCCCAGGG | nt10212~nt10232 | |
| | 2DS4_PCR_Ex789_F | Forward | 73 | GAAAGCCCGCTGAATCCTC | nt12884~nt12902 | 2865 |
| | 2DS4_PCR_Ex789_R | Reverse | 74 | GCAGAAGGCTGAAAGATAGTCTG | nt15726~nt15748 | |
| 2DS5 | 2DS5_PCR_Ex12_F | Forward | 75 | TGAGAACAATTTCCAGGAAGCCG | nt-199~nt-177 | 3089 |
| | 2DS5_PCR_Ex12_R | Reverse | 76 | CCTTTCCTGTGGACACTTGTC | nt2870~nt2890 | |
| | 2DS5_PCR_Ex45_F | Forward | 77 | TCCTGCCAAGGATTCCAATTCGA | nt3609~nt3631 | 2595 |
| | 2DS5_PCR_Ex45_R | Reverse | 78 | TCTGTCCATGCTTCTCTCCATCC | nt6181~nt6203 | |
| | 2DS5_PCR_Ex6_F | Forward | 79 | CTTGAAGTCTCAAGACAGTGGGT | nt9083~nt9105 | 863 |

TABLE 1-continued

KIR gene-specific PCR primers for 14 functional KIR genes

| KIR Gene | PCR Primer Name | Direction | SEQ ID No | Primer Sequence (5'→3') | Position in the full genomic sequence | Length of Amplicon (bp) |
|---|---|---|---|---|---|---|
| | 2DS5_PCR_Ex6_R | Reverse | 80 | ATGCACTTCATACTTTGAGCTAG | nt9923~nt9945 | |
| | 2DS5_PCR_Ex789_F | Forward | 81 | TGATGTKGAAGGAAGAGGCTCTG | nt11029~nt11051 | 3851 |
| | 2DS5_PCR_Ex789_R | Reverse | 82 | AGGGGAGGTGGAACTGCATGAGA | nt14857~nt14879 | |
| 3DL1 | 3DL1_PCR_Ex12_F | Forward | 83 | CGAGGTGTCAATTCTAGTGAGAG | nt-215~nt-193 | 2922 |
| | 3DL1_PCR_Ex12_R | Reverse | 84 | TACCACAAACATGGCAGCG | nt2689~nt2707 | |
| | 3DL1_PCR_Ex45_F | Forward | 85 | CACCCAGGTGTGGTAGGAGCC | nt1700~nt1720 | 4007 |
| | 3DL1_PCR_Ex45_R | Reverse | 86 | CTCTGTGTGGGTGAGAGGCCATG | nt5684~nt5706 | |
| | 3DL1_PCR_Ex6_F | Forward | 87 | GCCTGTAATACCACTACTCGGGT | nt8050~nt8072 | 892 |
| | 3DL1_PCR_Ex6_R | Reverse | 88 | CTAAAACACCTCGCCCTCATC | nt8921~nt8941 | |
| | 3DL1_PCR_Ex789_F | Forward | 89 | GCTATAACTGAGAAAGCAGGAGG | nt12700~nt12722 | 1496 |
| | 3DL1_PCR_Ex789_R | Reverse | 90 | CTGGAAAATAGTCCGAAGAAAGG | nt14173~nt14195 | |
| 3DL2 | 3DL2_PCR_Ex12_F | Forward | 91 | TGCAAGGTGGCAATTGTAGTCAC | nt-217~nt-195 | 1827 |
| | 3DL2_PCR_Ex12_R | Reverse | 92 | CGACGATAGTGACACTGAAGAGC | nt1588~nt1610 | |
| | 3DL2_PCR_Ex45_F | Forward | 93 | CCTCCTCTCTAAGGCAGTGCCTC | nt1477~nt1510 | 3964 |
| | 3DL2_PCR_Ex45_R | Reverse | 94 | CGGGTTTTCCTCACCTGTGACAG | nt5429~nt5451 | |
| | 3DL2_PCR_Ex6_F | Forward | 95 | GACAGGGCACCTCCAAACCCTCT | nt5584~nt5606 | 3721 |
| | 3DL2_PCR_Ex6_R | Reverse | 96 | ATTTTAGCCCAGTGACATGCACG | nt9282~nt9304 | |
| | 3DL2_PCR_Ex789_F | Forward | 97 | GCAGGAGAAAGCTGGGTCTCC | nt15186~nt15206 | 1099 |
| | 3DL2_PCR_Ex789_R | Reverse | 98 | CTGGTTTTGAGACAGGGCTGTTG | nt16262~nt16284 | |
| 3DL3 | 3DL3_PCR_Ex12_F | Forward | 99 | ACAACATCCTGTGTGCTGCTGAA | nt-63~nt-41 | 898 |
| | 3DL3_PCR_Ex12_R | Reverse | 100 | GTCAACCCCCTGTGTCGCCTG | nt815~nt835 | |
| | 3DL3_PCR_Ex345_F | Forward | 101 | GGAACCACAGTCATGACCCTGAC | nt1156~nt1178 | 4475 |
| | 3DL3_PCR_Ex345_R | Reverse | 102 | AAAGGGTGTAGGCGTTGCTGG | nt5608~nt5630 | |
| | 3DL3_PCR_Ex789_F | Forward | 103 | TGAGCCAGTCCCTCAAGGCTC | nt9865~nt9885 | 2165 |
| | 3DL3_PCR_Ex789_R | Reverse | 104 | GTTTTACTGCTGACAGAAGGCTG | nt12007~nt12029 | |
| 3DS1 | 3DS1_PCR_Ex12_F | Forward | 105 | CGAGGTGTCAATTCTAGTGAGAG | nt-215~nt-193 | 2314 |
| | 3DS1_PCR_Ex12_R | Reverse | 106 | CCTGTGACCATGATCACCAT | nt2080~nt2099 | |
| | 3DS1_PCR_Ex345_F | Forward | 107 | CAGCTGACACTTGTTGTAGGGAG | nt1634~nt1656 | 4859 |
| | 3DS1_PCR_Ex345_R | Reverse | 108 | AGTGGCATGATCTCGGCTCAG | nt6472~nt6492 | |
| | 3DS1_PCR_Ex6_F | Forward | 109 | TGATCCGCCCACCTCCGCT | nt7633~nt7651 | 1436 |
| | 3DS1_PCR_Ex6_R | Reverse | 110 | GCTGGGAGGTTTGAGCCAACG | nt9048~nt9068 | |
| | 3DS1_PCR_Ex789_F | Forward | 111 | GCTATAACTGAGAAAGCAGGAGG | nt13101~nt13123 | 1484 |
| | 3DS1_PCR_Ex789_R | Reverse | 112 | GAAGGCTGAAAGCTAGTCTGAGG | nt14562~nt14584 | |

(1) The first pair of 2DL1 specific PCR primers includes a forward primer 2DL1_PCR_Ex12_F (sequence: 5'-GTTCGGGAGGTTGGATCTC-3', its position in the full genomic sequence: nt-268~nt-250, SEQ ID No: 1) and a reverse primer 2DL1_PCR_Ex12_R (5'-CACACTGCAGCCCCTACCG-3', nt1332~nt1350, SEQ ID No: 2), which is used for amplifying the target sequence of KIR2DL1 covering exon 1, intron 1, exon 2, partial sequences of 5'-promoter region and intron 2/3, the target amplicon is 1618 bp in length. The second pair of 2DL1 specific PCR primers includes a forward primer 2DL1_PCR_Ex4_F (5'-TGATTCTCCTGAGTCTCCAGAGG-3', nt2501~nt2523, SEQ ID No: 3) and a reverse primer 2DL1_PCR_Ex4_R (5'-TGGAAGGAGAAGAGGCAGTTTCC-3', nt5288~nt5310, SEQ ID No: 4), which is used for amplifying the target sequence of KIR2DL1 covering exon 4 and its partial flanking intronic sequences, the target amplicon is 2810 bp in length. The third pair of 2DL1 specific PCR primers includes a forward primer 2DL1_PCR_Ex5_F (5'-CTGGCAGGGACCTACAGATGC-3', nt3692~nt3712, SEQ ID No: 5) and a reverse primer 2DL1_PCR_Ex5_R (5'-GGACAGCCATGGGCTTTCCTC-3', nt5608~nt5628, SEQ ID No: 6), which is used for amplifying the target sequence of KIR2DL1 covering exon 5 and its partial flanking intronic sequences, the target amplicon is 1937 bp in length. The fourth pair of 2DL1 specific PCR primers includes a forward primer 2DL1_PCR_Ex6_F (5'-TCCTGATTGTGAGTTCTTGGCAT-3', nt8082~nt8104, SEQ ID No: 7) and a reverse primer 2DL1_PCR_Ex6_R (5'-TGAGTCAGTSAGTCGAARTGTGC-3', nt9279~nt9301, SEQ ID No: 8), which is used for amplifying the target sequence of KIR2DL1 covering exon 6 and its partial flanking intronic sequences, the target amplicon is 1220 bp in length. The fifth pair of 2DL1 specific PCR primers includes a forward primer 2DL1_PCR_Ex789_F (5'-CCTCAGCACGTTCTATGGTTACT-3', nt12880~nt12902, SEQ ID No: 9) and a reverse primer 2DL1_PCR_Ex789_R (5'-TGTGATTGCAGCCTCAAGTAGAC-3', nt14249~nt14271, SEQ ID No: 10), which is used for amplifying the target sequence of KIR2DL1 covering exon 7, intron 7, exon 8, intron 8, exon 9, partial sequences of intron 6 and 3'-UTR region, the target amplicon is 1392 bp in length.

(2) The first pair of 2DL2 specific PCR primers includes a forward primer 2DL2_PCR_Ex12_F (5'-AGAGGTTGGATCTGAGACGTC-3', nt-263~nt-243, SEQ ID No: 11) and a reverse primer 2DL2_PCR_Ex12_R (5'-GGACCGATGGAGAAGTTGGCT-3', nt3590~nt3610, SEQ ID No: 12), which is used for amplifying the target sequence of KIR2DL2 covering exon 1, intron 1, exon 2, intron 2/3, partial sequences of the 5'-promoter region and exon 4, the target amplicon is 3873 bp in length. The second pair of 2DL2 specific PCR primers includes a forward primer 2DL2_PCR_Ex45_F (5'-GAGGCTACTAGAGACAGAGGGAC-3', nt3207~nt3229, SEQ ID No: 13) and a reverse primer 2DL2_PCR_Ex45_R (5'-CCCAAGCTTCGTCTTCTCTCT-3', nt5617~nt5637, SEQ ID No: 14), which is used for amplifying the target sequence of KIR2DL2 covering exon 4, intron 4, exon 5, partial sequences of intron 2/3 and intron 5, the target amplicon is 2431 bp in length. The third pair of 2DL2 specific PCR primers includes a forward primer 2DL2_PCR_Ex6_F (5'-CATGCCAACATCATGCTGTC-3', nt8530~nt8549, SEQ ID No: 15) and a reverse primer 2DL2_PCR_Ex6_R (5'-TCCCTGTCCTAGCCTCCATAC-3', nt9879~nt9899, SEQ ID No: 16), which is used for amplifying the target sequence of KIR2DL2 covering exon 6 and its partial flanking intronic sequences, the target amplicon is 1370 bp in length. The fourth pair of 2DL2 specific PCR primers includes a forward primer 2DL2_PCR_Ex789_F (5'-GAAGTTCCACTTGCCAAGGAATG-3', nt9210~nt9232, SEQ ID No: 17) and a reverse primer 2DL2_PCR_Ex789_R (5'-CAGCTGCTGGTACATGGGAGC-3', nt14071~nt14091, SEQ ID No: 18), which is used for amplifying the target sequence of KIR2DL2 covering exon 7, intron 7, exon 8, intron 8, exon 9, partial sequences of intron 6 and 3'-UTR region, the target amplicon is 4882 bp in length.

(3) The first pair of 2DL3 specific PCR primers includes a forward primer 2DL3_PCR_Ex12_F (5'-GGCYGMCTGTCTGCACAGA-3', nt-26~nt-8, SEQ ID No: 19) and a reverse primer 2DL3_PCR_Ex12_R (5'-GGTTTCCTGTTGCTGCTGTAG-3', nt2560~nt2580, SEQ ID No: 20), which is used for amplifying the target sequence of KIR2DL3 covering exon 1, intron 1, exon 2, partial sequences of the 5'-promoter region and intron 2/3, the target amplicon is 2606 bp in length. The second pair of 2DL3 specific PCR primers includes a forward primer 2DL3_PCR_Ex45_F (5'-AGAGAAGAGGGAGGGAGACAGAT-3', nt3231~nt3253, SEQ ID No: 21) and a reverse primer 2DL3_PCR_Ex45_R (5'-GCCATCCTGTGCCCTGATC-3', nt5651~nt5669, SEQ ID No: 22), which is used for amplifying the target sequences of KIR2DL3 covering exon 4, intron 4, exon 5, partial sequences of intron 2/3 and intron 5, the target amplicon is 2439 bp in length. The third pair of 2DL3 specific PCR primers includes a forward primer 2DL3_PCR_Ex6_F (5'-CCCACCTCAGGCTCTCAAAGG-3', nt7497~nt7517, SEQ ID No: 23) and a reverse primer 2DL3_PCR_Ex6_R (5'-GGCGTACAATGTCAGAGCTGC-3', nt8908~nt8928, SEQ ID No: 24), which is used for amplifying the target sequence of KIR2DL3 covering exon 6 and its partial fanking sequences, the target amplicon is 1432 bp in length. The fourth pair of 2DL3 specific PCR primers includes a forward primer 2DL3_PCR_Ex789_F (5'-ACTGAGAAAGCAGGAGAAAGCTG-3', nt12934~nt12956, SEQ ID No: 25) and a reverse primer 2DL3_PCR_Ex789_R (5'-CCTTCAGATTCCAGCTGCTGG-3', nt14063~nt14083, SEQ ID No: 26), which is used for amplifying the target sequence of KIR2DL3 covering exon 7, intron 7, exon 8, intron 8, exon 9, partial sequences of intron 6 and 3'-UTR region, the target amplicon is 1150 bp in length.

(4) The first pair of 2DL4 specific PCR primers includes a forward primer 2DL4_PCR_Ex12_F (5'-GTGGTCAATGTGTCAACTGCACG-3', nt-99~nt-77, SEQ ID No: 27) and a reverse primer 2DL4_PCR_Ex12_R (5'-CACAGGCTCCAAGGATTACAATG-3', nt1639~nt1661, SEQ ID No: 28), which is used for amplifying the target sequence of KIR2DL4 covering exon 1, intron 1, exon 2, intron 2, exon 3, partial sequences of 5'-promoter region and intron 3/4, the target amplicon is 1760 bp in length. The second pair of 2DL4 specific PCR primers includes a forward primer 2DL4_PCR_Ex35_F (5'-CTTTCTTCCCCATGGCTGAGTTG-3', nt571~nt593, SEQ ID No: 29) and a reverse primer 2DL4_PCR_Ex35_R (5'-CTTGGGCAACAAGAGTGAAACGC-3', nt3848~nt3870, SEQ ID No: 30), which is used for amplifying the target sequence of KIR2DL4 covering exon 3, intron 3/4, exon 5, partial sequences of intron 2 and intron 5, the target amplicon is 3300 bp in length. The third pair of 2DL4 specific PCR primers includes a forward primer 2DL4_PCR_Ex6_F (5'-AACCTCTACCTCCAGGATTCAAG-3', nt3904~nt3926, SEQ ID No: 31) and a reverse primer 2DL4_PCR_Ex6_R (5'-GTAAGTGGAAGTGTCATGTGCAC-3', nt5738~nt5760, SEQ ID No: 32), which is used for amplifying the target sequence of KIR2DL4 covering exon 6 and its partial flanking sequences, the target amplicon is 1857 bp in length. The fourth pair of 2DL4 specific PCR primers includes a forward primer 2DL4_PCR_Ex789_F (5'-CCAAGAAATGAGAGACAATCCAC-3', nt9442~nt9464, SEQ ID No: 33) and a reverse primer 2DL4_PCR_Ex789_R (5'-AGGCACCAGATTTGTGGT-GTG-3', nt10540~nt10560, SEQ ID No: 34), which is used for amplifying the target sequence of KIR2DL4 covering exon 7, intron 7, exon 8, intron 8, exon 9, partial sequences of intron 6 and 3'UTR region, the target amplicon is 1119 bp in length.

(5) The first pair of 2DL5 specific PCR primers includes a forward primer 2DL5_PCR_Ex12_F (5'-TCATAGT-GAAGGACGYGAGGTGC-3', nt-230~nt-208, SEQ ID No: 35) and a reverse primer 2DL5_PCR_Ex12_R (5'-AGC-CAATGTGTGAACCACAATAC-3', nt1238~nt1260, SEQ ID No: 36), which is used for amplifying the target sequence of KIR2DL5 covering exon 1, intron 1, exon 2, partial sequences of 5'-promoter region and intron 2, the target amplicon is 1490 bp in length. The second pair of 2DL5 specific PCR primers includes a forward primer 2DL5_PCR_Ex35_F (5'-CAGGACAAGCCCTTGCT-GTCT-3', nt1571~nt1591, SEQ ID No: 37) and a reverse primer 2DL5_PCR_Ex35_R (5'-GACAGAAACAAGCA-GTGGGTCAC-3', nt2993~nt3015, SEQ ID No: 38), which is used for amplifying the target sequence of KIR2DL5 covering exon 3, intron 3/4, exon 5, the target amplicon is 1445 bp in length. The third pair of 2DL5 specific PCR primers includes a forward primer 2DL5_PCR_Ex6_F (5'-CATTTCCTCACCTCTCTCCTGTCCT-3', nt5158~nt5182, SEQ ID No: 39) and a reverse primer 2DL5_PCR_Ex6_R (5'-AAGAGCAGAGGCCAAATGCATCG-3', nt6351~nt6373, SEQ ID No: 40), which is used for amplifying the target sequence of KIR2DL5 covering exon 6 and its partial flanking sequences, the target amplicon is 1216 bp in length. The fourth pair of 2DL5 specific PCR primers includes a forward primer 2DL5_PCR_Ex789_F (5'-CA-GATGTTGTATGTGCTTAGCTG-3', nt7907~nt7929, SEQ ID No: 41) and a reverse primer 2DL5_PCR_Ex789_R (5'-GGTTTTGAGACAGGGCTGTTGTC-3', nt8937~nt8959, SEQ ID No: 42), which is used for amplifying the target sequence of KIR2DL5 covering exon 7, intron 7, exon 8, intron 8, exon 9 and partial sequences of intron 6, the target amplicon is 1053 bp in length.

(6) The first pair of 2DS1 specific PCR primers includes a forward primer 2DS1_PCR_Ex12_F (5'-CATAGT-GAAGGACGCTAGGTGTA-3', nt-229~nt-207, SEQ ID No: 43) and a reverse primer 2DS1_PCR_Ex12_R (5'-GAGCCCTCTGACCTGTGACCG-3', nt2035~nt2055, SEQ ID No: 44), which is used for amplifying the target sequence of KIR2DS1 covering exon 1, intron 1, exon 2, partial sequences of 5'-promoter region and intron 2/3, the target amplicon is 2284 bp in length. The second pair of 2DS1 specific PCR primers includes a forward primer 2DS1_PCR_Ex45_F (5'-GTTCCTCTTCCACCCCCA-CAC-3', nt3175~nt3195, SEQ ID No: 45) and a reverse primer 2DS1_PCR_Ex45_R (5'-GAGGGTTTGGAGGT-GCCCTGTCG-3', nt5747~nt5769, SEQ ID No: 46), which is used for amplifying the target sequence of KIR2DS1 covering exon 4, intron 4, exon 5, partial sequences of intron 2/3 and intron 5, the target amplicon is 2595 bp in length. The third pair of 2DS1 specific PCR primers includes a forward primer 2DS1_PCR_Ex6_F (5'-TCCTGATTGT-GAGTTCTTGGCAT-3', nt8078~nt8100, SEQ ID No: 47) and a reverse primer 2DS1_PCR_Ex6_R (5'-GTCTCCTA-GATTCCAGTTACGCC-3', nt10742~nt10764, SEQ ID No: 48), which is used for amplifying the target sequence of KIR2DS1 covering exon 6 and its partial flanking sequences, the target amplicon is 2687 bp in length. The fourth pair of 2DS1 specific PCR primers includes a forward primer 2DS1_PCR_Ex789_F (5'-CGTGGAAAAGGCAAT-TCCCGA-3', nt10765~nt10785, SEQ ID No: 49) and a reverse primer 2DS1_PCR_Ex789_R (5'-GGAGGTG-GAACAGCACGTGTC-3', nt14330~nt14350, SEQ ID No: 50), which is used for amplifying the sequence of KIR2DS1 covering exon 7, intron 7, exon 8, intron 8, exon 9, partial sequences of intron 6 and 3'-UTR region, the target amplicon is 3586 bp in length.

(7) The first pair of 2DS2 specific PCR primers includes a forward primer 2DS2_PCR_Ex12_F (5'-TGAGAGGTTG-GATCTGAGACGTC-3', nt-265~nt-243, SEQ ID No: 51) and a reverse primer 2DS2_PCR_Ex12_R (5'-ACATCCA-GGCTCTTATCAGCCTT-3', nt2956~nt2978, SEQ ID No: 52), which is used for amplifying the target sequence of KIR2DS2 covering exon 1, intron 1, exon 2, partial sequences of 5'-promoter region and intron 2/3, the target amplicon is 3243 bp in length. The second pair of 2DS2 specific PCR primers includes a forward primer 2DS2_PCR_Ex45_F (5'-GCTTCCATGCTTCTGA-TAATTTTG-3', nt2420~nt2443, SEQ ID No: 53) and a reverse primer 2DS2_PCR_Ex45_R (5'-CTCTGGGTCTCTCCTGACCGT-3', nt5639~nt5659, SEQ ID No: 54), which is used for amplifying the sequence of KIR2DS2 covering exon 4, intron 4, exon 5, partial sequences of intron 2/3 and intron 5, the target amplicon is 3240 bp in length. The third pair of 2DS2 specific PCR primers includes a forward primer 2DS2_PCR_Ex6_F (5'-CATTCTGCTCCGTTGTTCTATGTC-3', nt8282~nt8305, SEQ ID No: 55) and a reverse primer 2DS2_PCR_Ex6_R (5'-GCCAGGGTTGCTTCATGACCTAT-3', nt9024~nt9046, SEQ ID No: 56), which is used for amplifying the sequence of KIR2DS2 covering exon 6 and its partial flanking sequences, the target amplicon is 765 bp in length. The fourth pair of 2DS2 specific PCR primers includes a forward primer 2DS2_PCR_Ex789_F (5'-GA-TAGGCCATGGGGAGGTAAATT-3', nt11463~nt11485, SEQ ID No: 57) and a reverse primer 2DS2_PCR_Ex789_R (5'-GGGCAGACATGTTTATTTGAAGGC-3', nt14250~nt14273, SEQ ID No: 58), which is used for amplifying the sequence of KIR2DS2 covering exon 7, intron 7, exon 8, intron 8, exon 9, partial sequences of intron 6 and 3'-UTR region, the target amplicon is 2811 bp in length.

(8) The first pair of 2DS3 specific PCR primers includes a forward primer 2DS3_PCR_Ex12_F (5'-TGTAAACTG-CATGGGCAGGGA-3', nt-90~nt-70, SEQ ID No: 59) and a reverse primer 2DS3_PCR_Ex12_R (5'-CTCTGACCTGT-GACCATGATCAG-3', nt2368~nt2390, SEQ ID No: 60), which is used for amplifying the target sequence of KIR2DS3 covering exon 1, intron 1, exon 2, partial sequences of 5'-promoter region and intron 2/3, the target amplicon is 2480 bp in length. The second pair of 2DS3 specific PCR primers includes a forward 2DS3_PCR_Ex45_F (5'-CTGAGCCCAGCGGCAAGGC-3', nt3586~nt3604, SEQ ID No: 61) and a reverse primer 2DS3_PCR_Ex45_R (5'-ATCCCTCCCTCACAC-CGAGGA-3', nt6039~nt6059, SEQ ID No: 62), which is used for amplifying the sequence of KIR2DS3 covering exon 4, intron 4, exon 5, partial sequences of intron 2/3 and intron 5, the target amplicon is 2474 bp in length. The third pair of 2DS3 specific PCR primers includes a forward primer 2DS3_PCR_Ex6_F (5'-TACCAGGGTTCTC-CTTTCTCTAG-3', nt7491~nt7513, SEQ ID No: 63) and a reverse primer 2DS3_PCR_Ex6_R (5'-AGGAAGGGGAC-CAGGAGCG-3', nt9878~nt9896, SEQ ID No: 64), which is used for amplifying the sequence of KIR2DS3 covering exon 6 and its partial flanking sequences, the target amplicon is 2406 bp in length. The fourth pair of 2DS3 specific PCR primers includes a forward primer 2DS3_PCR_Ex789_F (5'-TGATGTTGAAGGAAGAGGCTCTT-3', nt10853~nt10875, SEQ ID No: 65) and a reverse primer 2DS3_PCR_Ex789_R (5'-GATAGTCTGAGGGGAGGTG-GAACT-3', nt14688~nt14711, SEQ ID No: 66), which is used for amplifying the sequence of KIR2DS3 covering exon 7, intron 7, exon 8, intron 8, exon 9, partial sequences of intron 6 and 3'-UTR region, the target amplicon is 3859 bp in length.

(9) The first pair of 2DS4 specific PCR primers includes a forward primer 2DS4_PCR_Ex12_F (5'-ACCAT-GTCGCTCATGGTCATCAT-3', nt-3~nt20, SEQ ID No: 67) and a reverse primer 2DS4_PCR_Ex12_R (5'-TTGTCCT-GACCACCTTGGGGT-3', nt3070~nt3090, SEQ ID No: 68), which is used for amplifying the target sequence of KIR2DS4 covering exon 1, intron 1, exon 2, partial sequences of 5'-promoter region and intron 2/3, the target amplicon is 3093 bp in length. The second pair of 2DS4 specific PCR primers includes a forward primer 2DS4_PCR_Ex45_F (5'-TCAGTTCATACCTCCTGC-CAAGG-3', nt4419~nt4441, SEQ ID No: 69) and a reverse primer 2DS4_PCR_Ex45_R (5'-CGTGGTCAGGAGTTC-CAGAGC-3', nt7611~nt7631, SEQ ID No: 70), which is used for amplifying the target sequence of KIR2DS4 covering exon 4, intron 4, exon 5, partial sequences of intron 2/3 and intron 5, the target amplicon is 3213 bp in length. The third pair of 2DS4 specific PCR primers includes a forward primer 2DS4_PCR_Ex6_F (5'-CTGGACTCCCAGGGC-CCAATG-3', nt10004~nt10024, SEQ ID No: 71) and a reverse primer 2DS4_PCR_Ex6_R (5'-AAGGTTTCCAC-CTCCCCAGGG-3', nt10212~nt10232, SEQ ID No: 72), which is used for amplifying the target sequence of KIR2DS4 covering exon 6 and its partial flanking sequences, the target amplicon is 229 bp in length. The fourth pair of 2DS4 specific PCR primers includes a forward primer 2DS4_PCR_Ex789_F (5'-GAAAGCCCGCT-GAATCCTC-3', nt12884~nt12902, SEQ ID No: 73) and a reverse primer 2DS4_PCR_Ex789_R (5'-GCAGAAGGCT-GAAAGATAGTCTG-3', nt15726~nt15748, SEQ ID No: 74), which is used for amplifying the target sequence of KIR2DS4 covering exon 7, intron 7, exon 8, intron 8, exon 9, partial sequences of intron 6 and 3'-UTR region, the target amplicon is 2865 bp in length.

(10) The first pair of 2DS5 specific PCR primers includes a forward primer 2DS5_PCR_Ex12_F (5'-TGAGAACAATTTCCAGGAAGCCG-3', nt-199~nt-177, SEQ ID No: 75) and a reverse primer 2DS5_PCR_Ex12_R (5'-CCTTTCCTGTGGACACTTGTC-3', nt2870~nt2890, SEQ ID No: 76), which is used for amplifying the sequence of KIR2DS5 covering exon 1, intron 1, exon 2, partial sequences of 5'-promoter region and intron 2/3, the target amplicon is 3089 bp in length. The second pair of 2DS5 specific PCR primers includes a forward primer 2DS5_PCR_Ex45_F (5'-TCCTGCCAAGGATTCCAAT-TCGA-3', nt3609~nt3631, SEQ ID No: 77) and a reverse primer 2DS5_PCR_Ex45_R (5'-TCTGTCCATGCT-TCTCTCCATCC-3', nt6181~nt6203, SEQ ID No: 78), which is used for amplifying the sequence of KIR2DS5 covering exon 4, intron 4, exon 5, partial of intron 2/3 and intron 5, the target amplicon is 2595 bp in length. The third pair of 2DS5 specific PCR primers includes a forward primer 2DS5_PCR_Ex6_F (5'-CTTGAAGTCT-CAAGACAGTGGGT-3', nt9083~nt9105, SEQ ID No: 79) and a reverse primer 2DS5_PCR_Ex6_R (5'-ATGCACT-TCATACTTTGAGCTAG-3', nt9923~nt9945, SEQ ID No: 80), which is used for amplifying the target sequence of KIR2DS5 covering exon 6 and its partial flanking sequences, the target amplicon is 863 bp in length. The fourth pair of 2DS5 specific PCR primers includes a forward primer 2DS5_PCR_Ex789_F (5'-TGATGTK-GAAGGAAGAGGCTCTG-3', nt11029~nt11051, SEQ ID No: 81) and a reverse primer 2DS5_PCR_Ex789_R (5'-AGGGGAGGTGGAACTGCATGAGA-3', nt14857~nt14879, SEQ ID No: 82), which is used for amplifying the target sequence of KIR2DS5 covering exon 7, intron 7, exon 8, intron 8, exon 9, partial sequences of intron 6 and 3'-UTR region, the target amplicon is 3851 bp in length.

(11) The first pair of 3DL1 specific PCR primers includes a forward primer 3DL1_PCR_Ex12_F (5'-CGAGGTGT-CAATTCTAGTGAGAG-3', nt-215~nt-193, SEQ ID No: 83) and a reverse primer 3DL1_PCR_Ex12_R (5'-TACCA-CAAACATGGCAGCG-3', nt2689~nt2707, SEQ ID No: 84), which is used for amplifying the target sequence of KIR3DL1 covering exon 1, intron 1, exon 2, intron 2, exon 3, partial sequences of 5'-promoter region and intron 3, the target amplicon is 2922 bp in length. The second pair of 3DL1 specific PCR primers includes a forward primer 3DL1_PCR_Ex345_F (5'-CACCCAGGTGTGGTAG-GAGCC-3', nt1700~nt1720, SEQ ID No: 85) and a reverse primer 3DL1_PCR_Ex345_R (5'-CTCTGTGTGGGT-GAGAGGCCATG-3', nt5684~nt5706, SEQ ID No: 86), which is used for amplifying the target sequence of KIR3DL1 covering exon 3, intron 3, exon 4, intron 4, exon 5, partial sequences of intron 2 and intron 5, the target amplicon is 4007 bp in length. The third pair of 3DL1 specific PCR primers includes a forward primer 3DL1_PCR_Ex6_F (5'-GCCTGTAATACCAC-TACTCGGGT-3', nt8050~nt8072, SEQ ID No: 87) and a reverse primer 3DL1_PCR_Ex6_R (5'-CTAAAACAC-CTCGCCCTCATC-3', nt8921~nt8941, SEQ ID No: 88), which is used for amplifying the sequence of KIR3DL1 covering exon 6 and its partial flanking sequences, the target amplicon is 892 bp in length. The fourth pair of 3DL1 specific PCR primers includes a forward primer 3DL1_PCR_Ex789_F (5'-GCTATAACTGAGAAAGCAG-GAGG-3', nt12700~nt12722, SEQ ID No: 89) and a reverse primer 3DL1_PCR_Ex789_R (5'-CTGGAAAATAGTC-CGAAGAAAGG-3', nt14173~nt14195, SEQ ID No: 90), which is used for amplifying the target sequence of KIR3DL1 covering exon 7, intron 7, exon 8, intron 8, exon 9, partial sequences of intron 6 and 3'-UTR region, the target amplicon is 1496 bp in length.

(12) The first pair of 3DL2 specific PCR primers includes a forward primer 3DL2_PCR_Ex12_F (5'-TGCAAGGTG-GCAATTGTAGTCAC-3', nt-217~nt-195, SEQ ID No: 91) and a reverse primer 3DL2_PCR_Ex12_R (5'-CGACGA-TAGTGACACTGAAGAGC-3', nt1588~nt1610, SEQ ID No: 92), which is used for amplifying the target sequence of KIR3DL2 covering exon 1, intron 1, exon 2, intron 2, partial sequences of 5'-promoter region and exon 3, the target amplicon is 1827 bp in length. The second pair of 3DL2 specific PCR primers includes a forward primer 3DL2_PCR_Ex345_F (5'-CCTCCTCTCTAAGGCAGT-GCCTC-3', nt1488~nt1510, SEQ ID No: 93) and a reverse primer 3DL2_PCR_Ex345_R (5'-CGGGTTTTCCTCAC-CTGTGACAG-3', nt5429~nt5451, SEQ ID No: 94), which is used for amplifying the target sequence of KIR3DL2 covering exon 3, intron 3, exon 4, intron 4, exon 5, partial sequences of intron 2 and intron 5, the target amplicon is 3964 bp in length. The third pair of 3DL2 specific PCR primers includes a forward primer 3DL2_PCR_Ex6_F (5'-GACAGGGCACCTCCAAACCCTCT-3', nt5584~nt5606, SEQ ID No: 95) and a reverse primer 3DL2_PCR_Ex6_R (5'-ATTTTAGCCCAGTGACATGCACG-3', nt9282~nt9304, SEQ ID No: 96), which is used for amplifying the target sequence of KIR3DL2 covering exon 6 and its partial flanking sequences, the target amplicon is 3721 bp in length. The fourth pair of 3DL2 specific PCR primers includes a forward primer 3DL2_PCR_Ex789_F (5'-GCAGGAGAAAGCTGGGTCTCC-3', nt15186~nt15206, SEQ ID No: 97) and a reverse primer 3DL2_PCR_Ex789_R (5'-CTGGTTTTGAGACAGGGCTGTTG-3', nt16262~nt16284, SEQ ID No: 98), which is used for amplifying the target sequence of KIR3DL2 covering exon 7, intron 7, exon 8, intron 8, exon 9, partial sequences of intron 6 and 3'-UTR region, the target amplicon is 1099 bp in length.

(13) The first pair of 3DL3 specific PCR primers includes a forward primer 3DL3_PCR_Ex12_F (5'-ACAACATCCTGTGTGCTGCTGAA-3', nt-63~nt-41, SEQ ID No: 99) and a reverse primer 3DL3_PCR_Ex12_R (5'-GTCAACCCCTGTGTCGCCTG-3', nt815~nt835, SEQ ID No: 100), which is used for amplifying the target sequence of KIR3DL3 covering exon 1, intron 1, exon 2, partial sequences of 5'-promoter region and intron 2, the target amplicon is 898 bp in length. The second pair of 3DL3 specific PCR primers includes a forward primer 3DL3_PCR_Ex345_F (5'-GGAACCACAGTCATGACCCTGAC-3', nt1156~nt1178, SEQ ID No: 101) and a reverse primer 3DL3_PCR_Ex345_R (5'-AAAGGGTGTAGGCGTTGCTGG-3', nt5608~nt5630, SEQ ID No: 102), which is used for amplifying the target sequence of KIR3DL3 covering exon 3, intron 3, exon 4, intron 4, exon 5, partial sequences of intron 2 and intron 5/6, the target amplicon is 4475 bp. The third pair of 3DL3 specific PCR primers includes a forward primer 3DL3_PCR_Ex789_F (5'-TGAGCCAGTCCCTCAAGGCTC-3', nt9865~nt9885, SEQ ID No: 103) and a reverse primer 3DL3_PCR_Ex789_R (5'-GTTTTACTGCTGACAGAAGGCTG-3', nt12007~nt12029, SEQ ID No: 104), which is used for amplifying the target sequence of KIR3DL3 covering exon 7, intron 7, exon 8, intron 8, exon 9, partial sequences of intron 5/6 and 3'-UTR region, the target amplicon is 2165 bp in length.

(14) The first pair of 3DS1 specific PCR primers includes a forward primer 3DS1_PCR_Ex12_F (5'-CGAGGTGTCAATTCTAGTGAGAG-3', nt-215~nt-193, SEQ ID No: 105) and a reverse primer 3DS1_PCR_Ex12_R (5'-CCTGTGACCATGATCACCAT-3', nt2080~nt2099, SEQ ID No: 106), which is used for amplifying the target sequence of KIR3DS1 covering exon 1, intron 1, exon 2, intron 2, partial sequences of 5'-promoter region and exon 3, the target amplicon is 2314 bp in length. The second pair of 3DS1 specific PCR primers includes a forward primer 3DS1_PCR_Ex345_F (5'-CAGCTGACACTTGTTGTAGGGAG-3', nt1634~nt1656, SEQ ID No: 107) and a reverse primer 3DS1_PCR_Ex345_R (5'-AGTGGCATGATCTCGGCTCAG-3', nt6472~nt6492, SEQ ID No: 108), which is used for amplifying the target sequence of KIR3DS1 covering exon 3, intron 3, exon 4, intron 4, exon 5, partial sequences of intron 2 and intron 5, the target amplicon is 4859 bp in length. The third pair of 3DS1 specific PCR primers includes a forward primer 3DS1_PCR_Ex6_F (5'-TGATCCGCCCACCTCCGCT-3', nt7633~nt7651, SEQ ID No: 109) and a reverse primer 3DS1_PCR_Ex6_R (5'-GCTGGGAGGTTTGAGCCAACG-3', nt9048~nt9068, SEQ ID No: 110), which is used for amplifying exon 6 and its partial flanking sequences, the target amplicon is 1436 bp in length. The fourth pair of 3DS1 specific PCR primers includes a forward primer 3DS1_PCR_Ex789_F (5'-GCTATAACTGAGAAAGCAGGAGG-3', nt13101~nt13123, SEQ ID No: 111) and a reverse primer 3DS1_PCR_Ex789_R (5'-GAAGGCTGAAAGCTAGTCTGAGG-3', nt14562~nt14584, SEQ ID No: 112), which is used for amplifying the target sequence of KIR3DS1 covering exon 7, intron 7, exon 8, intron 8, exon 9, partial sequences of intron 6 and 3'-UTR region, the target amplicon is 1484 bp in length.

III. All the PCR amplifications can be carried out in a volume of 10 µL containing:

| | |
|---|---|
| 10× PCR Buffer (without MgCl$_2$) | 1.0 µL, |
| 2.5 mM dNTP | 0.8 µL, |
| 5.0 mM MgCl$_2$ | 3.0 µL, |
| 10 µM each PCR Primer | 0.4 µL, |
| 50~100 ng/µL Genomic DNA | 2.0 µL, |
| 5 U/µL Taq DNA Polymerase | 0.1 µL, |
| Add ddH$_2$O to | 10.0 µL. |

IV. PCR amplifications can be conducted simultaneously under the same thermocycling parameters, and the thermocycling parameters are described below:

| | |
|---|---|
| 95° C. | 3 min; |
| 95° C. | 15 Sec, |
| 68° C. | 15 Sec, |
| 72° C. | 3.5 min, 35 cycles; |
| 72° C. | 7 min; |
| 4° C. | Infinite. |

V. Purification of PCR products can be carried out using the purification system described below:

| | |
|---|---|
| 1 U/µL Thermosensitive Alkaline Phosphatase | 1 µL, |
| 20 U/µL Exonuclease I | 0.25 µL, |
| 10× Reaction Buffer | 3 µL, |
| PCR Products | 10 µL. |

VI. Purification of PCR products can be carried out under the same thermocycling parameters, and the thermocycling parameters are described below:

| | |
|---|---|
| 37° C. | 45 min, |
| 85° C. | 15 min, |
| 4° C. | Infinite. |

VII. The nucleotide sequences of each exon carried by purified PCR amplicons are determined in both directions using the forward and reverse sequencing primers. As for KIR2DL1~5, 2DS1~5 and KIR3DL3 genes, each KIR gene is sequenced by sixteen specific sequencing primers, respectively. For KIR3DL1~2 and KIR3DS1 genes, each KIR gene is sequenced by eighteen specific sequencing primers, respectively. A total number of 230 KIR gene-specific forward and reverse sequencing primers for all the 14 functional KIR genes are shown in the following Table 2:

TABLE 2

KIR Gene-specific Forward and Reverse Sequencing Primers for All 14 Functional KIR Genes

| KIR Gene | Sequencing Primer Name | Direction | SEQ ID No | Primer Sequence (5'→3') | Position in Full Genomic Sequence |
|---|---|---|---|---|---|
| 2DL1 | 2DL1_SBT_Ex1_F | Forward | 113 | CGTGTTCCGCTCTTGAGCG | nt-177~nt-159 |
| | 2DL1_SBT_Ex1_R | Reverse | 114 | TCACTCCCTCCCTCTATTG | nt50~nt68 |
| | 2DL1_SBT_Ex2_F | Forward | 115 | TTCTTGGGTGCAGGTAGGC | nt855~nt873 |
| | 2DL1_SBT_Ex2_R | Reverse | 116 | ACCCTGGTCCCCACAGAAC | nt1210~nt1228 |
| | 2DL1_SBT_Ex4_F | Forward | 117 | AAGGGGAAGCCTGACTCAA | nt3400~nt3418 |
| | 2DL1_SBT_Ex4_R | Reverse | 118 | CCAATTCCTGGATCATTCAC | nt3827~nt3846 |
| | 2DL1_SBT_Ex5_F | Forward | 119 | GTTCTCAGCTCAGGTGAAG | nt5420~nt5258 |
| | 2DL1_SBT_Ex5_R | Reverse | 120 | AAACAAGCAGTGGGTCACTTGAC | nt5574~nt5596 |
| | 2DL1_SBT_Ex6_F | Forward | 121 | TTTCCACTGAGTGGAGGAC | nt8698~nt8716 |
| | 2DL1_SBT_Ex6_R | Reverse | 122 | TGGAGTTCGGAGATGGTGG | nt8920~nt8938 |
| | 2DL1_SBT_Ex7_F | Forward | 123 | ATGTGGTTACCTGTCAATC | nt12979~nt12997 |
| | 2DL1_SBT_Ex7_R | Reverse | 124 | TCCTGCTTCCCCACATGGC | nt13207~nt13225 |
| | 2DL1_SBT_Ex8_F | Forward | 125 | CTCAGCCACCTATGGTCTC | nt13533~nt13551 |
| | 2DL1_SBT_Ex8_R | Reverse | 126 | TCTCTGTGTGAAAACGCAG | nt13835~nt13853 |
| | 2DL1_SBT_Ex9_F | Forward | 127 | ACAGAACAGCGAATAGCGA | nt13667~nt13685 |
| | 2DL1_SBT_Ex9_R | Reverse | 128 | TAAGATGCAGACTCATGCC | nt14060~nt14078 |
| 2DL2 | 2DL2_SBT_Ex1_F | Forward | 129 | AGAGGTTGGATCTGAGACGTC | nt-263~nt-243 |
| | 2DL2_SBT_Ex1_R | Reverse | 130 | TCTCCAACTCTGGGCCCCG | nt81~nt99 |
| | 2DL2_SBT_Ex2_F | Forward | 131 | TTCTTGGGTGCAGGTAGGC | nt799~nt817 |
| | 2DL2_SBT_Ex2_R | Reverse | 132 | CCCAGTCTAACCCTGGTCC | nt1163~nt1181 |
| | 2DL2_SBT_Ex4_F | Forward | 133 | AAGGGGAAGCCTCACTCAT | nt3332~nt3350 |
| | 2DL2_SBT_Ex4_R | Reverse | 134 | GGCCCCTGTGTCTGTCCTC | nt3900~nt3918 |
| | 2DL2_SBT_Ex5_F | Forward | 135 | GCTGTGACAAGGAAGATCC | nt5179~nt5197 |
| | 2DL2_SBT_Ex5_R | Reverse | 136 | AAGCTCCTCAGCTAAGGCT | nt5564~nt5582 |
| | 2DL2_SBT_Ex6_F | Forward | 137 | ATCCCAGGACTCCCAGGGC | nt8669~nt8687 |
| | 2DL2_SBT_Ex6_R | Reverse | 138 | GGCGTACAATGTCAGAGCTGC | nt8928~nt8948 |
| | 2DL2_SBT_Ex7_F | Forward | 139 | ATCTGGGTGCTTGTCCTAA | nt12990~nt13008 |
| | 2DL2_SBT_Ex7_R | Reverse | 140 | CCTCTGCTTCGTGAGACTTAC | nt13213~nt13233 |
| | 2DL2_SBT_Ex8_F | Forward | 141 | CCCAGAAGTGCCCTCCGAG | nt13628~nt13646 |
| | 2DL2_SBT_Ex8_R | Reverse | 142 | TCTCTGTGTGAAAACGCAG | nt13876~nt13894 |
| | 2DL2_SBT_Ex9_F | Forward | 143 | ACAGAACAGCGAATAGCGA | nt13708~nt13726 |
| | 2DL2_SBT_Ex9_R | Reverse | 144 | GGCTGTTGTCTCCCTAGAAGACG | |
| 2DL3 | 2DL3_SBT_Ex1_F | Forward | 145 | CYGMCTGTCTGCACAGA | nt-24~nt-8 |
| | 2DL3_SBT_Ex1_R | Reverse | 146 | TCTCCAACTCTGGGCCCCG | nt81~nt99 |
| | 2DL3_SBT_Ex2_F | Forward | 147 | TTCTTGGGTGCAGGTAGGC | nt799~nt817 |
| | 2DL3_SBT_Ex2_R | Reverse | 148 | ACCCTGGTCCCCACAGAAC | nt1154~nt1172 |
| | 2DL3_SBT_Ex4_F | Forward | 149 | CAGCAAGGGGAAGCCTCA | nt3329~nt3346 |
| | 2DL3_SBT_Ex4_R | Reverse | 150 | GGCCCCTGTGTCTGTCCTC | nt3901~nt3919 |
| | 2DL3_SBT_Ex5_F | Forward | 151 | GAGCATTAGGTCATAGAGC | nt5131~nt5149 |
| | 2DL3_SBT_Ex5_R | Reverse | 152 | CTCTCTGCATCTGTCCATGCTTC | nt5602~nt5624 |
| | 2DL3_SBT_Ex6_F | Forward | 153 | TACTCAGGAGTTTGAGGCC | nt8310~nt8328 |
| | 2DL3_SBT_Ex6_R | Reverse | 154 | GGCGTACAATGTCAGAGCTGC | nt8908~nt8928 |
| | 2DL3_SBT_Ex7_F | Forward | 155 | TCTGGGTGCTTGTCCTAAAGG | nt12969~nt12989 |
| | 2DL3_SBT_Ex7_R | Reverse | 156 | CAGGCAATGGTCTGTGAGC | nt13361~nt13379 |
| | 2DL3_SBT_Ex8_F | Forward | 157 | CTTCATCGCTGGTGCTG | nt13166~nt13182 |
| | 2DL3_SBT_Ex8_R | Reverse | 158 | GCTGAGTGAGGGAGGGTGC | nt13772~nt13790 |
| | 2DL3_SBT_Ex9_F | Forward | 159 | CCCAGCCTCGTGGCTAG | nt13724~nt13740 |
| | 2DL3_SBT_Ex9_R | Reverse | 160 | GGCAGGAGACAACTTTGGATCW | nt13957~nt13978 |
| 2DL4 | 2DL4_SBT_Ex1_F | Forward | 161 | GTGGTCAATGTGTCAACTGCACG | nt-99~nt-77 |
| | 2DL4_SBT_Ex1_R | Reverse | 162 | CCTGAGCCACTGGGCGCCA | nt166~nt184 |
| | 2DL4_SBT_Ex2_F | Forward | 163 | GAGCCATGTTCTGAAGCAAGT | nt111~nt131 |
| | 2DL4_SBT_Ex2_R | Reverse | 164 | CACCCTCTGTGCTGCCTCC | nt345~nt363 |
| | 2DL4_SBT_Ex4_F | Forward | 165 | TACTCCTCTCTGAGGCGGC | nt1140~nt1158 |
| | 2DL4_SBT_Ex4_R | Reverse | 166 | CCAGAAGCTCTGGGACTCA | nt1502~nt1520 |
| | 2DL4_SBT_Ex5_F | Forward | 167 | GGGAGGGGAGCTGTGACA | nt2275~nt2293 |
| | 2DL4_SBT_Ex5_R | Reverse | 168 | GCTTCTCTCCATCATCAGC | nt2691~nt2709 |
| | 2DL4_SBT_Ex6_F | Forward | 169 | CAGGCATCCTCATTGCCAC | nt5179~nt5197 |
| | 2DL4_SBT_Ex6_R | Reverse | 170 | TGGCAGGTGCTGAGCCAAC | nt5341~nt5359 |
| | 2DL4_SBT_Ex7_F | Forward | 171 | TCGCCAGACACCTGCATGC | nt9519~nt9537 |

TABLE 2-continued

KIR Gene-specific Forward and Reverse Sequencing Primers for All 14 Functional KIR Genes

| KIR Gene | Sequencing Primer Name | Direction | SEQ ID No | Primer Sequence (5'→3') | Position in Full Genomic Sequence |
|---|---|---|---|---|---|
| | 2DL4_SBT_Ex7_R | Reverse | 172 | TTTGGAGCACCAGC | nt9600~nt9613 |
| | 2DL4_SBT_Ex8_F | Forward | 173 | GAGGACCCAGAAGTGCCCT | nt10030~nt10048 |
| | 2DL4_SBT_Ex8_R | Reverse | 174 | CTGGAGAGAGGGAAATCCT | nt10215~nt10233 |
| | 2DL4_SBT_Ex9_F | Forward | 175 | CCAGCCTCATGGATACAGTCT | nt10150~nt10233 |
| | 2DL4_SBT_Ex9_R | Reverse | 176 | GGAAGAGTGATGCTCTAAGATGG | nt10516~nt10538 |
| 2DL5 | 2DL5_SBT_Ex1_F | Forward | 177 | CCAAATAACATCCTGTGCGCT | nt-67~nt-47 |
| | 2DL5_SBT_Ex1_R | Reverse | 178 | AGATCTCCATCCCCGCACT | nt64~nt82 |
| | 2DL5_SBT_Ex2_F | Forward | 179 | CAGCAAGGGCCTGGCTACC | nt668~nt686 |
| | 2DL5_SBT_Ex2_R | Reverse | 180 | GAAAATCCCCACCGGGCT | nt872~nt890 |
| | 2DL5_SBT_Ex4_F | Forward | 181 | ACAAGCCCTTGCTGTCTGCCT | nt1575~nt1595 |
| | 2DL5_SBT_Ex4_R | Reverse | 182 | CAGATGCTCTGGGATTCAG | nt1891~nt1909 |
| | 2DL5_SBT_Ex5_F | Forward | 183 | CAGGTGTGAGGGGAGCTGT | nt2665~nt2683 |
| | 2DL5_SBT_Ex5_R | Reverse | 184 | CGGGTCTGACCACTCATAGGGT | nt2970~nt2991 |
| | 2DL5_SBT_Ex6_F | Forward | 185 | TCACCTCTCTCCTGTCCTGTGT | nt5165~nt5186 |
| | 2DL5_SBT_Ex6_R | Reverse | 186 | TGAGCCAATGCTTGAATCCAAGA | nt5295~nt5317 |
| | 2DL5_SBT_Ex7_F | Forward | 187 | ATCCATAAAGAGGAACTGCTATA | nt7951~nt7973 |
| | 2DL5_SBT_Ex7_R | Reverse | 188 | CCTTGGTCCAGGGACCATC | nt8201~nt8219 |
| | 2DL5_SBT_Ex8_F | Forward | 189 | CACCTACGGCCTCCCGCTG | nt8480~nt8498 |
| | 2DL5_SBT_Ex8_R | Reverse | 190 | GAGGGTGCTCACATTCTTCAA | nt8680~nt8700 |
| | 2DL5_SBT_Ex9_F | Forward | 191 | TGCCGGGGACAGAACAGTG | nt8600~nt8618 |
| | 2DL5_SBT_Ex9_R | Reverse | 192 | CTCAAGGCCTGACTGTGGTGCTT | nt8899~nt8921 |
| 2DS1 | 2DS1_SBT_Ex1_F | Forward | 193 | CTCCCATGATGTGGTCAAC | nt-109~nt-91 |
| | 2DS1_SBT_Ex1_R | Reverse | 194 | TCTCCAACCCCACACTCCC | nt61~nt79 |
| | 2DS1_SBT_Ex2_F | Forward | 195 | TTCTTGGGTGCAGGTAGGC | nt855~nt873 |
| | 2DS1_SBT_Ex2_R | Reverse | 196 | CTGCCAAGGGAATGAAAGG | nt1185~nt1203 |
| | 2DS1_SBT_Ex4_F | Forward | 197 | GGTGCCATGGATGGGATGA | nt3423~nt3441 |
| | 2DS1_SBT_Ex4_R | Reverse | 198 | CAAGTCCTGGATCATTCAC | nt3827~nt3845 |
| | 2DS1_SBT_Ex5_F | Forward | 199 | AGAGCAGGGGAGTGAGTTC | nt5221~nt5239 |
| | 2DS1_SBT_Ex5_R | Reverse | 200 | GGCTCTAGGATCATAGGAC | nt5628~nt5646 |
| | 2DS1_SBT_Ex6_F | Forward | 201 | TCCTCAAAGATTTCCACTGAGTG | nt8694~nt8706 |
| | 2DS1_SBT_Ex6_R | Reverse | 202 | GTGAGATGCTGAGTCAACGC | nt8871~nt8890 |
| | 2DS1_SBT_Ex7_F | Forward | 203 | GTGGTTACCTGCCAATCAAG | nt12981~nt13000 |
| | 2DS1_SBT_Ex7_R | Reverse | 204 | TGAGGAACACACATCCGCGT | nt13236~nt13255 |
| | 2DS1_SBT_Ex8_F | Forward | 205 | ATGGCCTCCCCCTGTTTGT | nt13547~nt13565 |
| | 2DS1_SBT_Ex8_R | Reverse | 206 | GGGAATAAGACTAGCCACG | nt13713~nt13731 |
| | 2DS1_SBT_Ex9_F | Forward | 207 | CTCCTCGGCCCAGCCTCGT | nt13697~nt13715 |
| | 2DS1_SBT_Ex9_R | Reverse | 208 | TCCCCTCAAGGCCTGACTG | nt13971~nt13989 |
| 2DS2 | 2DS2_SBT_Ex1_F | Forward | 209 | ATAACATCCTGTGCGCTGC | nt-63~nt-45 |
| | 2DS2_SBT_Ex1_R | Reverse | 210 | CCAACTCTGGGCCCCGATC | nt78~nt96 |
| | 2DS2_SBT_Ex2_F | Forward | 211 | AAGGGAGTCCTGGTTTGCC | nt772~nt790 |
| | 2DS2_SBT_Ex2_R | Reverse | 212 | GTCAGAAATGTGGGCCGAG | nt981~nt999 |
| | 2DS2_SBT_Ex4_F | Forward | 213 | CACCTTCTAAACTCACAACC | nt3268~nt3287 |
| | 2DS2_SBT_Ex4_R | Reverse | 214 | CACTCTGCAGCCCAATGAC | nt3624~nt3642 |
| | 2DS2_SBT_Ex5_F | Forward | 215 | AGAGCAGGGGAGTGAGTTC | nt5030~nt5048 |
| | 2DS2_SBT_Ex5_R | Reverse | 216 | GAAGCTCCTCAGCTAAGGC | nt5453~nt5471 |
| | 2DS2_SBT_Ex6_F | Forward | 217 | CCAGGGCCCAATATTAGAT | nt8465~nt8483 |
| | 2DS2_SBT_Ex6_R | Reverse | 218 | TGAGTCAACGCCTGAATCC | nt8686~nt8704 |
| | 2DS2_SBT_Ex7_F | Forward | 219 | GCCAATCAAGAAATGCGAG | nt12815~nt12833 |
| | 2DS2_SBT_Ex7_R | Reverse | 220 | GTCCTGCCTCTGTGGCTCC | nt13108~nt13126 |
| | 2DS2_SBT_Ex8_F | Forward | 221 | ATGAGGACCCAGAAGTGCC | nt13407~nt13425 |
| | 2DS2_SBT_Ex8_R | Reverse | 222 | CCTCCTGATGGTCTTGTTC | nt13621~nt13639 |
| | 2DS2_SBT_Ex9_F | Forward | 223 | AGGTAGGTGCTCCTCGGCC | nt13512~nt13530 |
| | 2DS2_SBT_Ex9_R | Reverse | 224 | AGAAGATCCCCTCAAGGCC | nt13801~nt13819 |
| 2DS3 | 2DS3_SBT_Ex1_F | Forward | 225 | CAGGGAGCCAAATAACATC | nt-75~nt-57 |
| | 2DS3_SBT_Ex1_R | Reverse | 226 | CGCTCCCTCCCTCTATTCC | nt49~nt67 |

TABLE 2-continued

KIR Gene-specific Forward and Reverse Sequencing Primers for All 14 Functional KIR Genes

| KIR Gene | Sequencing Primer Name | Direction | SEQ ID No | Primer Sequence (5'→3') | Position in Full Genomic Sequence |
|---|---|---|---|---|---|
| | 2DS3_SBT_Ex2_F | Forward | 227 | GCCGAGAGCCCTGTTCTTG | nt1182~nt1200 |
| | 2DS3_SBT_Ex2_R | Reverse | 228 | ACAGGACTTCCCTCCCGTT | nt1432~nt1450 |
| | 2DS3_SBT_Ex4_F | Forward | 229 | AGAGAGACACCTTCTAAAT | nt3780~nt3798 |
| | 2DS3_SBT_Ex4_R | Reverse | 230 | ATCATTCACTCTGTGTCCG | nt4152~nt4170 |
| | 2DS3_SBT_Ex5_F | Forward | 231 | AGGAAGATCCTCCATAAGG | nt5596~nt5614 |
| | 2DS3_SBT_Ex5_R | Reverse | 232 | GGCTCTAGGATCATAGGAC | nt5957~nt5975 |
| | 2DS3_SBT_Ex6_F | Forward | 233 | TCCCAGGGCCCAATATTAG | nt8968~nt8986 |
| | 2DS3_SBT_Ex6_R | Reverse | 234 | CACTGAGCCCTGTGTTGGG | nt9291~nt9309 |
| | 2DS3_SBT_Ex7_F | Forward | 235 | GTGCTTGTCCTAAAGAGACGT | nt13284~nt13304 |
| | 2DS3_SBT_Ex7_R | Reverse | 236 | TGAGTGGCTGCAGGGGACG | nt13709~nt13727 |
| | 2DS3_SBT_Ex8_F | Forward | 237 | GACCTCAGGCACCTATGGC | nt13862~nt13880 |
| | 2DS3_SBT_Ex8_R | Reverse | 238 | GCTGAGTGAGGGAGGGTGC | nt14082~nt14100 |
| | 2DS3_SBT_Ex9_F | Forward | 239 | CGGCCCAGCCTCGTGGCTA | nt14031~nt14049 |
| | 2DS3_SBT_Ex9_R | Reverse | 240 | TGTCTTGGGCCTCTGAGAAGGGG | nt14196~nt14218 |
| 2DS4 | 2DS4_SBT_Ex1_F | Forward | 241 | ACCATGTCGCTCATGGTC | nt-3~nt15 |
| | 2DS4_SBT_Ex1_R | Reverse | 242 | GGCTCATCACTCCATCTCT | nt148~nt166 |
| | 2DS4_SBT_Ex2_F | Forward | 243 | GAAGGGGCTGGCTATCAAG | nt2218~nt2236 |
| | 2DS4_SBT_Ex2_R | Reverse | 244 | GACTTCCCTCCCGTTTCAG | nt2404~nt2422 |
| | 2DS4_SBT_Ex4_F | Forward | 245 | AGAGAGACACCTTCTAAAC | nt4774~nt4792 |
| | 2DS4_SBT_Ex4_R | Reverse | 246 | CACCTGGGTCTCCAAGTCC | nt5168~nt5186 |
| | 2DS4_SBT_Ex5_F | Forward | 247 | AGTTCTCAGGTCAGGTGTG | nt6589~nt6607 |
| | 2DS4_SBT_Ex5_R | Reverse | 248 | GGAAGCTCCTCAGCTAAGG | nt7001~nt7019 |
| | 2DS4_SBT_Ex6_F | Forward | 249 | CTGGACTCCCAGGGCCCAATG | nt10004~nt10024 |
| | 2DS4_SBT_Ex6_R | Reverse | 250 | TTCCACCTCCCCAGGGTTC | nt10209~nt10227 |
| | 2DS4_SBT_Ex7_F | Forward | 251 | CGCCATTTGGGTGCTTGTC | nt14317~nt14335 |
| | 2DS4_SBT_Ex7_R | Reverse | 252 | GGTGAGGAACACACATCCG | nt14611~nt14629 |
| | 2DS4_SBT_Ex8_F | Forward | 253 | AGTCTGCTGTTGGCAACTG | nt14883~nt14901 |
| | 2DS4_SBT_Ex8_R | Reverse | 254 | CCTCCTGATGGTCTTGTTC | nt15169~nt15187 |
| | 2DS4_SBT_Ex9_F | Forward | 255 | CTCGGCCCAGCCTCGTGGC | nt15072~nt15090 |
| | 2DS4_SBT_Ex9_R | Reverse | 256 | CAACTTTGGATCTGGGCTC | nt15304~nt15322 |
| 2DS5 | 2DS5_SBT_Ex1_F | Forward | 257 | GGCGCCAAATAACATCCTG | nt-72~nt-54 |
| | 2DS5_SBT_Ex1_R | Reverse | 258 | GCCCAGATCTCCATCCCCG | nt68~nt86 |
| | 2DS5_SBT_Ex2_F | Forward | 259 | GGCACTGAGKGTGAGTTTC | nt1383~nt1401 |
| | 2DS5_SBT_Ex2_R | Reverse | 260 | TGACAGGACTTCCCTCCCG | nt1606~nt1624 |
| | 2DS5_SBT_Ex4_F | Forward | 261 | GACACCTTCTAAATTCACAAAC | nt3958~nt3979 |
| | 2DS5_SBT_Ex4_R | Reverse | 262 | CTCTGCATCCCAATGACAATG | nt4315~nt4335 |
| | 2DS5_SBT_Ex5_F | Forward | 263 | CCTCCCTGAGGAAAATGCC | nt5786~nt5804 |
| | 2DS5_SBT_Ex5_R | Reverse | 264 | TCATAGGACATGGGACAGC | nt6192~nt6147 |
| | 2DS5_SBT_Ex6_F | Forward | 265 | CAGGGCCCAATATTAGATAAC | nt9147~nt9167 |
| | 2DS5_SBT_Ex6_R | Reverse | 266 | GGAGTATCTGGAGTTCGGAGA | nt9426~nt9446 |
| | 2DS5_SBT_Ex7_F | Forward | 267 | CTGTCAATCAAGAAATGCGAG | nt13495~nt13515 |
| | 2DS5_SBT_Ex7_R | Reverse | 268 | GGAACACACACCCGCGTGC | nt13740~nt13758 |
| | 2DS5_SBT_Ex8_F | Forward | 269 | AGATAGAATGTCTGAGTCTGC | nt14003~nt14023 |
| | 2DS5_SBT_Ex8_R | Reverse | 270 | ACACAGTGATCCAATTATGCG | nt14329~nt14349 |
| | 2DS5_SBT_Ex9_F | Forward | 271 | GGTAGGTGCTCCTCGGCCC | nt14195~nt14213 |
| | 2DS5_SBT_Ex9_R | Reverse | 272 | ATGGGAGCTGGCAACCCGG | nt14528~nt14546 |
| 3DL1 | 3DL1_SBT_Ex1_F | Forward | 273 | CAGGGCGCCAAATAACATC | nt-74~nt-56 |
| | 3DL1_SBT_Ex1_R | Reverse | 274 | CAGATCTCCATCCCCGCAC | nt65~nt83 |
| | 3DL1_SBT_Ex2_F | Forward | 275 | AGGGCCTGGCTGCCAAGAC | nt940~nt958 |
| | 3DL1_SBT_Ex2_R | Reverse | 276 | AATGTGGGCCGAGCATCCG | nt1182~nt1200 |
| | 3DL1_SBT_Ex3_F | Forward | 277 | GGGGAGAATCTTCTGGGCACT | nt1736~nt1756 |
| | 3DL1_SBT_Ex3_R | Reverse | 278 | TGATGGGACCCTGACGGAC | nt2167~nt2185 |
| | 3DL1_SBT_Ex4_F | Forward | 279 | TGGAGGCACCTGCACCAGG | nt3052~nt3070 |
| | 3DL1_SBT_Ex4_R | Reverse | 280 | TGGTACAGACCTCACCAAG | nt3633~nt3651 |
| | 3DL1_SBT_Ex5_F | Forward | 281 | CAGGTATGAGGGGAGCTATG | nt5001~nt5020 |
| | 3DL1_SBT_Ex5_R | Reverse | 282 | CCTGTCTGCCATCCTGCGC | nt5490~nt5508 |
| | 3DL1_SBT_Ex6_F | Forward | 283 | AAGCACCCTCATTTCCTCAC | nt8485~nt8504 |
| | 3DL1_SBT_Ex6_R | Reverse | 284 | CAACACTTGCATCCAAGGC | nt8631~nt8649 |

TABLE 2-continued

KIR Gene-specific Forward and Reverse Sequencing Primers for All 14 Functional KIR Genes

| KIR Gene | Sequencing Primer Name | Direction | SEQ ID No | Primer Sequence (5'→3') | Position in Full Genomic Sequence |
|---|---|---|---|---|---|
| | 3DL1_SBT_Ex7_F | Forward | 285 | CCCGCCATCTGGGTGCTTG | nt12734~nt12752 |
| | 3DL1_SBT_Ex7_R | Reverse | 286 | TCCTGCTTCCCCACATGGC | nt13001~nt13019 |
| | 3DL1_SBT_Ex8_F | Forward | 287 | CCAGAAGTGCCCTCCGAGC | nt13882~nt13400 |
| | 3DL1_SBT_Ex8_R | Reverse | 288 | TGTTTGGGAATAACACTAGCC | nt13507~13527 |
| | 3DL1_SBT_Ex9_F | Forward | 289 | CGTGGCTAGTGTTATTCCC | nt13504~nt13522 |
| | 3DL1_SBT_Ex9_R | Reverse | 290 | ATGGGAGCTGGCAACTCGG | nt13833~nt13851 |
| 3DL2 | 3DL2_SBT_Ex1_F | Forward | 291 | GCCAAATAACATCCTGTGCGC | nt-68~nt-48 |
| | 3DL2_SBT_Ex1_R | Reverse | 292 | TAGGCCGAGATCTCCATCC | nt71~nt89 |
| | 3DL2_SBT_Ex2_F | Forward | 293 | GAGGCTAAGTTTACCTTCAGC | nt624~nt644 |
| | 3DL2_SBT_Ex2_R | Reverse | 294 | GACTTCCCTCCTGTTTCAG | nt834~nt852 |
| | 3DL2_SBT_Ex3_F | Forward | 295 | GGCCCAGCACTGTGGTGCC | nt1553~nt1571 |
| | 3DL2_SBT_Ex3_R | Reverse | 296 | GCCCATTTCCCCTGTATTC | nt1930~nt1948 |
| | 3DL2_SBT_Ex4_F | Forward | 297 | GAGAGATGCCTTCTAAACT | nt3235~nt3253 |
| | 3DL2_SBT_Ex4_R | Reverse | 298 | TCTCCATAAGAATCCCACGCT | nt3663~nt3683 |
| | 3DL2_SBT_Ex5_F | Forward | 299 | CCTCCCTGAGGAAACTGCC | nt5111~nt5129 |
| | 3DL2_SBT_Ex5_R | Reverse | 300 | GAAAGAGCCGAAGCATCTG | nt5361~nt5379 |
| | 3DL2_SBT_Ex6_F | Forward | 301 | CAACCTCAAAGATTTCCATTG | nt8530~nt8550 |
| | 3DL2_SBT_Ex6_R | Reverse | 302 | CAACACTTGCATCCAAGGC | nt8707~nt8725 |
| | 3DL2_SBT_Ex7_F | Forward | 303 | GAGATGTTCCATGTGGTTACC | nt15231~nt15251 |
| | 3DL2_SBT_Ex7_R | Reverse | 304 | GGAACACACACCCGCGTGC | nt15494~nt15512 |
| | 3DL2_SBT_Ex8_F | Forward | 305 | TCTGAGTCTGGATGTTGGC | nt15764~nt15782 |
| | 3DL2_SBT_Ex8_R | Reverse | 306 | GGGTCTTGTTCATCAGAGTCC | nt16046~nt16066 |
| | 3DL2_SBT_Ex9_F | Forward | 307 | CCTCGGCCCAGCCTCACGG | nt15957~nt15975 |
| | 3DL2_SBT_Ex9_R | Reverse | 308 | GACTGTGGTGCTCGTGGGC | nt16216~nt16234 |
| 3DL3 | 3DL3_SBT_Ex1_F | Forward | 309 | ACAACATCCTGTGTGCTGCTGAA | nt-63~nt-41 |
| | 3DL3_SBT_Ex1_R | Reverse | 310 | TCCCTCCCTCGATTCCCTT | nt46~nt64 |
| | 3DL3_SBT_Ex2_F | Forward | 311 | GATGTACAGATGGATCATC | nt672~nt690 |
| | 3DL3_SBT_Ex2_R | Reverse | 312 | GTCAACCCCTGTGTCGCCTG | nt815~nt835 |
| | 3DL3_SBT_Ex3_F | Forward | 313 | GCTCCACATCCTCCTCTCT | nt1474~nt1492 |
| | 3DL3_SBT_Ex3_R | Reverse | 314 | ATCCCCCTTTACCCCAAAT | nt1905~nt1923 |
| | 3DL3_SBT_Ex4_F | Forward | 315 | GGGAAGCCTCACTTATTTCAG | nt2996~nt3016 |
| | 3DL3_SBT_Ex4_R | Reverse | 316 | ACCTGGGGCTTCCAGTCCT | nt3431~nt3449 |
| | 3DL3_SBT_Ex5_F | Forward | 317 | GAGAGCTGTGACAASGAAG | nt4900~nt4918 |
| | 3DL3_SBT_Ex5_R | Reverse | 318 | GCAGGAAGCTCCTCAGCTA | nt5294~nt5312 |
| | 3DL3_SBT_Ex7_F | Forward | 319 | GTGAGACAATTCATATAGA | nt10650~nt10668 |
| | 3DL3_SBT_Ex7_R | Reverse | 320 | TGCTTCCCCACATGGCCCT | nt10852~nt10870 |
| | 3DL3_SBT_Ex8_F | Forward | 321 | GACCTCAGGCACCTATGGC | nt11178~nt11196 |
| | 3DL3_SBT_Ex8_R | Reverse | 322 | GAGTGAGGGAGGGTGCTCA | nt11395~nt11413 |
| | 3DL3_SBT_Ex9_F | Forward | 323 | CRTGGCTAGTCTTATTCCC | nt11358~nt11376 |
| | 3DL3_SBT_Ex9_R | Reverse | 324 | CCCTAGAAGATCCCATCAA | nt11627~nt11645 |
| 3DS1 | 3DS1_SBT_Ex1_F | Forward | 325 | AAGCCATGCTCCGCTCTTG | nt-181~nt-163 |
| | 3DS1_SBT_Ex1_R | Reverse | 326 | CAGATCTCCATCCCCGCAC | nt65~nt83 |
| | 3DS1_SBT_Ex2_F | Forward | 327 | AGTGGGGCAGCAGGGTG | nt968~nt985 |
| | 3DS1_SBT_Ex2_R | Reverse | 328 | AATGTGGGCCGAGCATCCG | nt1182~nt1200 |
| | 3DS1_SBT_Ex3_F | Forward | 329 | GGGGAGAATCTTCTGGGCACT | nt1735~nt1755 |
| | 3DS1_SBT_Ex3_R | Reverse | 330 | TGATGGGACCCTGACGGAC | nt2166~nt2184 |
| | 3DS1_SBT_Ex4_F | Forward | 331 | GGAGAGAGACAGACACGGG | nt3485~nt3503 |
| | 3DS1_SBT_Ex4_R | Reverse | 332 | TGGTACAGACCTCACCAAG | nt4007~nt4025 |
| | 3DS1_SBT_Ex5_F | Forward | 333 | CAGGTGTGAGGGGAGCTGT | nt5403~nt5421 |
| | 3DS1_SBT_Ex5_R | Reverse | 334 | CCTGTCTGCCATCCTGCGC | nt5892~nt5910 |
| | 3DS1_SBT_Ex6_F | Forward | 335 | TCAAGACAGTGGGCATCGCAC | nt8763~nt8783 |
| | 3DS1_SBT_Ex6_R | Reverse | 336 | GGGAGGTTTGAGCCAACGCTT | nt9045~nt9065 |
| | 3DS1_SBT_Ex7_F | Forward | 337 | CGCTGTATGTGGTTACCTGTG | nt13165~nt13185 |
| | 3DS1_SBT_Ex7_R | Reverse | 338 | GGTGAGGAACACACACCCG | nt13432~nt13450 |
| | 3DS1_SBT_Ex8_F | Forward | 339 | CCAGAAGTGCCCTCCGAGC | nt13784~nt13802 |
| | 3DS1_SBT_Ex8_R | Reverse | 340 | GCTGAGTGAGGGAGGGTGC | nt13944~nt13962 |

TABLE 2-continued

KIR Gene-specific Forward and Reverse Sequencing Primers for All 14 Functional KIR Genes

| KIR Gene | Sequencing Primer Name | Direction | SEQ ID No | Primer Sequence (5'→3') | Position in Full Genomic Sequence |
|---|---|---|---|---|---|
| | 3DS1_SBT_Ex9_F | Forward | 341 | CGTGGCTAGTGTTATTCCC | nt13904~nt13922 |
| | 3DS1_SBT_Ex9_R | Reverse | 342 | GGCCTCTGAGAAGGGCGAG | nt14055~nt14073 |

(1) The forward and reverse sequencing primers for exon 1 of KIR2DL1 are 2DL1_SBT_Ex1_F (5'-CGTGTTC-CGCTCTTGAGCG-3', nt-177~nt-159, SEQ ID No: 113) and 2DL1_SBT_Ex1_R (5'-TCACTCCCTCCCTCTATTG-3', nt50~nt68, SEQ ID No: 114), respectively;

The forward and reverse sequencing primers for exon 2 of KIR2DL1 are 2DL1_SBT_Ex2_F (5'-TTCTTGGGTGCA-GGTAGGC-3', nt855~nt873, SEQ ID No: 115) and 2DL1_SBT_Ex2_R (5'-ACCCTGGTCCCCACAGAAC-3', nt1210~nt1228, SEQ ID No: 116), respectively;

The forward and reverse sequencing primers for exon 4 of KIR2DL1 are 2DL1_SBT_Ex4_F (5'-AAGGGGAAGCCT-GACTCAA-3', nt3400~nt3418, SEQ ID No: 117) and 2DL1_SBT_Ex4_R (5'-CCAATTCCTGGATCATTCAC-3', nt3827~nt3846, SEQ ID No: 118), respectively;

The forward and reverse sequencing primers for exon 5 of KIR2DL1 are 2DL1_SBT_Ex5_F (5'-GTTCTCAGCTCA-GGTGAAG-3', nt5240~nt5258, SEQ ID No: 119) and 2DL1_SBT_Ex5_R (5'-AAACAAGCAGTGGGTCACTT-GAC-3', nt5574~nt5596, SEQ ID No: 120), respectively;

The forward and reverse sequencing primers for exon 6 of KIR2DL1 are 2DL1_SBT_Ex6_F (5'-TTTCCACT-GAGTGGAGGAC-3', nt8698~nt8716, SEQ ID No: 121) and 2DL1_SBT_Ex6_R (5'-TGGAGTTCGGAGATG-GTGG-3', nt8920~nt8938, SEQ ID No: 122), respectively;

The forward and reverse sequencing primers for exon 7 of KIR2DL1 are 2DL1_SBT_Ex7_F (5'-ATGTGGTTACCT-GTCAATC-3', nt12979~nt12997, SEQ ID No: 123) and 2DL1_SBT_Ex7_R (5'-TCCTGCTTCCCCACATGGC-3', nt13207~nt13225, SEQ ID No: 124), respectively;

The forward and reverse sequencing primers for exon 8 of KIR2DL1 are 2DL1_SBT_Ex8_F (5'-CTCAGCCAC-CTATGGTCTC-3', nt13533~nt13551, SEQ ID No: 125) and 2DL1_SBT_Ex8_R (5'-TCTCTGTGTGAAAACGCAG-3', nt13835~nt13853, SEQ ID No: 126), respectively;

The forward and reverse sequencing primers for exon 9 of KIR2DL1 are 2DL1_SBT_Ex9_F (5'-ACAGAACAGC-GAATAGCGA-3', nt13667~nt13685, SEQ ID No: 127) and 2DL1_SBT_Ex9_R (5'-TAAGATGCAGACTCATGCC-3', nt14060~nt14078, SEQ ID No: 128), respectively.

(2) The forward and reverse sequencing primers for exon 1 of KIR2DL2 are 2DL2_SBT_Ex1_F (5'-AGAGGTTG-GATCTGAGACGTC-3', nt-263~nt-243, SEQ ID No: 129) and 2DL2_SBT_Ex1_R (5'-TCTCCAACTCTGGGC-CCCG-3', nt81~nt99, SEQ ID No: 130), respectively;

The forward and reverse sequencing primers for exon 2 of KIR2DL2 are 2DL2_SBT_Ex2_F (5'-TTCTTGGGTGCA-GGTAGGC-3', nt799~nt817, SEQ ID No: 131) and 2DL2_SBT_Ex2_R (5'-CCCAGTCTAACCCTGGTCC-3', nt1163~nt1181, SEQ ID No: 132), respectively;

The forward and reverse sequencing primers for exon 4 of KIR2DL2 are 2DL2_SBT_Ex4_F (5'-AAGGGGAAGCCT-CACTCAT-3', nt3332~nt3350, SEQ ID No: 133) and 2DL2_SBT_Ex4_R (5'-GGCCCTGTGTCTGTCCTC-3', nt3900~nt3918, SEQ ID No: 134), respectively;

The forward and reverse sequencing primers for exon 5 of KIR2DL2 are 2DL2_SBT_Ex5_F (5'-GCTGT-GACAAGGAAGATCC-3', nt5179~nt5197, SEQ ID No: 135) and 2DL2_SBT_Ex5_R (5'-AAGCTCCTCA-GCTAAGGCT-3', nt5564~nt5582, SEQ ID No: 136), respectively;

The forward and reverse sequencing primers for exon 6 of KIR2DL2 are 2DL2_SBT_Ex6_F (5'-ATCCCAGGACTC-CCAGGGC-3', nt8669~nt8687, SEQ ID No: 137) and 2DL2_SBT_Ex6_R (5'-GGCGTACAATGTCA-GAGCTGC-3', nt8928~nt8948, SEQ ID No: 138), respectively;

The forward and reverse sequencing primers for exon 7 of KIR2DL2 are 2DL2_SBT_Ex7_F (5'-ATCTGGGTGCTT-GTCCTAA-3', nt12990~nt13008, SEQ ID No: 139) and 2DL2_SBT_Ex7_R (5'-CCTCTGCTTCGTGAGACTTAC-3', nt13213~nt13233, SEQ ID No: 140), respectively;

The forward and reverse sequencing primers for exon 8 of KIR2DL2 are 2DL2_SBT_Ex8_F (5'-CCCAGAAGTGC-CCTCCGAG-3', nt13628~nt13646, SEQ ID No: 141) and 2DL2_SBT_Ex8_R (5'-TCTCTGTGTGAAAACGCAG-3', nt13876~nt13894, SEQ ID No: 142), respectively;

The forward and reverse sequencing primers for exon 9 of KIR2DL2 are 2DL2_SBT_Ex9_F (5'-ACAGAACAGC-GAATAGCGA-3', nt13708~nt13726, SEQ ID No: 143) and 2DL2_SBT_Ex9_R (5'-GGCTGTTGTCTCCCTA-GAAGACG-3', nt14026~nt14048, SEQ ID No: 144), respectively.

(3) The forward and reverse sequencing primers for exon 1 of KIR2DL3 are 2DL3_SBT_Ex1_F (5'-CYGMCTGTCT-GCACAGA-3', nt-24~nt-8, SEQ ID No: 145) and 2DL3_SBT_Ex1_R (5'-TCTCCAACTCTGGGCCCCG-3', nt81~nt99, SEQ ID No: 146), respectively;

The forward and reverse sequencing primers for exon 2 of KIR2DL3 are 2DL3_SBT_Ex2_F (5'-TTCTTGGGTGCA-GGTAGGC-3', nt799~nt817, SEQ ID No: 147) and 2DL3_SBT_Ex2_R (5'-ACCCTGGTCCCCACAGAAC-3', nt1154~nt1172, SEQ ID No: 148), respectively;

The forward and reverse sequencing primers for exon 4 of KIR2DL3 are 2DL3_SBT_Ex4_F (5'-CAG-CAAGGGGAAGCCTCA-3', nt3329~nt3346, SEQ ID No: 149) and 2DL3_SBT_Ex4_R (5'-GGCCCTGTGTCT-GTCCTC-3', nt3901~nt3919, SEQ ID No: 150), respectively;

The forward and reverse sequencing primers for exon 5 of KIR2DL3 are 2DL3_SBT_Ex5_F (5'-GAGCATTAGGT-CATAGAGC-3', nt5131~nt5149, SEQ ID No: 151) and 2DL3_SBT_Ex5_R (5'-CTCTCTGCATCTGTCCAT-GCTTC-3', nt5602~nt5624, SEQ ID No: 152), respectively;

The forward and reverse sequencing primers for exon 6 of KIR2DL3 are 2DL3_SBT_Ex6_F (5'-TACTCAGGAGTTT-GAGGCC-3', nt8310~nt8328, SEQ ID No: 153) and 2DL3_SBT_Ex6_R (5'-GGCGTACAATGTCA-GAGCTGC-3', nt8908~nt8928, SEQ ID No: 154), respectively;

The forward and reverse sequencing primers for exon 7 of KIR2DL3 are 2DL3_SBT_Ex7_F (5'-TCTGGGTGCTT-GTCCTAAAGG-3', nt12969~nt12989, SEQ ID No: 155) and 2DL3_SBT_Ex7_R (5'-CAGGCAATGGTCTGT-GAGC-3', nt13361~nt13379, SEQ ID No: 156), respectively;

The forward and reverse sequencing primers for exon 8 of KIR2DL3 are 2DL3_SBT_Ex8_F (5'-CTTCATCGCTGGT-GCTG-3', nt13166~nt13182, SEQ ID No: 157) and 2DL3_SBT_Ex8_R (5'-GCTGAGTGAGGGAGGGTGC-3', nt13772~nt13790, SEQ ID No: 158), respectively;

The forward and reverse sequencing primers for exon 9 of KIR2DL3 are 2DL3_SBT_Ex9_F (5'-CCCAGCCTCGTG-GCTAG-3', nt13724~nt13740, SEQ ID No: 159) and 2DL3_SBT_Ex9_R (5'-GGCAGGAGACAACTTTG-GATCW-3', nt13957~nt13978, SEQ ID No: 160), respectively.

(4) The forward and reverse sequencing primers for exon 1 of KIR2DL4 are 2DL4_SBT_Ex1_F (5'-GTGGTCAAT-GTGTCAACTGCACG-3', nt-99~nt-77, SEQ ID No: 161) and 2DL4_SBT_Ex1_R (5'-CCTGAGC-CACTGGGCGCCA-3', nt166~nt184, SEQ ID No: 162), respectively;

The forward and reverse sequencing primers for exon 2 of KIR2DL4 are 2DL4_SBT_Ex2_F (5'-GAGCCATGTTCT-GAAGCAAGT-3', nt111~nt131, SEQ ID No: 163) and 2DL4_SBT_Ex2_R (5'-CACCCTCTGTGCTGCCTCC-3', nt345~nt363, SEQ ID No: 164), respectively;

The forward and reverse sequencing primers for exon 3 of KIR2DL4 are 2DL4_SBT_Ex3_F (5'-TACTCCTCTCT-GAGGCGGC-3', nt1140~nt1158, SEQ ID No: 165) and 2DL4_SBT_Ex3_R (5'-CCAGAAGCTCTGGGACTCA-3', nt1502~nt1520, SEQ ID No: 166), respectively;

The forward and reverse sequencing primers for exon 5 of KIR2DL4 are 2DL4_SBT_Ex5_F (5'-GGGAGGGGAGCT-GTGACAA-3', nt2275~nt2293, SEQ ID No: 167) and 2DL4_SBT_Ex5_R (5'-GCTTCTCTCCATCATCAGC-3', nt2691~nt2709, SEQ ID No: 168), respectively;

The forward and reverse sequencing primers for exon 6 of KIR2DL4 are 2DL4_SBT_Ex6_F (5'-CAGGCATCCTCAT-TGCCAC-3', nt5179~nt5197, SEQ ID No: 169) and 2DL4_SBT_Ex6_R (5'-TGGCAGGTGCTGAGCCAAC-3', nt5341~nt5359, SEQ ID No: 170), respectively;

The forward and reverse sequencing primers for exon 7 of KIR2DL4 are 2DL4_SBT_Ex7_F (5'-TCGCCAGACAC-CTGCATGC-3', nt9519~nt9537, SEQ ID No: 171) and 2DL4_SBT_Ex7_R (5'-TTTGGAGCACCAGC-3', nt9600~nt9613, SEQ ID No: 172), respectively;

The forward and reverse sequencing primers for exon 8 of KIR2DL4 are 2DL4_SBT_Ex8_F (5'-GAGGACCCA-GAAGTGCCCT-3', nt10030~nt10048, SEQ ID No: 173) and 2DL4_SBT_Ex8_R (5'-CTGGAGA-GAGGGAAATCCT-3', nt10215~nt10233, SEQ ID No: 174), respectively;

The forward and reverse sequencing primers for exon 9 of KIR2DL4 are 2DL4_SBT_Ex9_F (5'-CCAGCCTCATG-GATACAGTCT-3', nt10150~nt10170, SEQ ID No: 175) and 2DL4_SBT_Ex9_R (5'-GGAAGAGTGAT-GCTCTAAGATGG-3', nt10516~nt10538, SEQ ID No: 176), respectively.

(5) The forward and reverse sequencing primers for exon 1 of KIR2DL5 are 2DL5_SBT_Ex1_F (5'-CCAAATAACATCCTGTGCGCT-3', nt-67~nt-47, SEQ ID No: 177) and 2DL5_SBT_Ex1_R (5'-AGATCTCCATC-CCCGCACT-3', nt64~nt82, SEQ ID No: 178), respectively;

The forward and reverse sequencing primers for exon 2 of KIR2DL5 are 2DL5_SBT_Ex2_F (5'-CAGCAAGGGC-CTGGCTACC-3', nt668~nt686, SEQ ID No: 179) and 2DL5_SBT_Ex2_R (5'-GAAAATCCCCCACCGGGCT-3', nt872~nt890, SEQ ID No: 180), respectively;

The forward and reverse sequencing primers for exon 3 of KIR2DL5 are 2DL5_SBT_Ex3_F (5'-ACAAGCCCTT-GCTGTCTGCCT-3', nt1575~nt1595, SEQ ID No: 181) and 2DL5_SBT_Ex3_R (5'-CAGATGCTCTGGGATTCAG-3', nt1891~nt1909, SEQ ID No: 182), respectively;

The forward and reverse sequencing primers for exon 5 of KIR2DL5 are 2DL5_SBT_Ex5_F (5'-CAGGTGT-GAGGGGAGCTGT-3', nt2665~nt2683, SEQ ID No: 183) and 2DL5_SBT_Ex5_R (5'-CGGGTCTGACCACT-CATAGGGT-3', nt2970~nt2991, SEQ ID No: 184), respectively;

The forward and reverse sequencing primers for exon 6 of KIR2DL5 are 2DL5_SBT_Ex6_F (5'-TCACCTCTCTCCT-GTCCTGTGT-3', nt5165~nt5186, SEQ ID No: 185) and 2DL5_SBT_Ex6_R (5'-TGAGCCAATGCTTGAATC-CAAGA-3', nt5295~nt5317, SEQ ID No: 186), respectively;

The forward and reverse sequencing primers for exon 7 of KIR2DL5 are 2DL5_SBT_Ex7_F (5'-ATCCATAAAGAG-GAACTGCTATA-3', nt7951~nt7973, SEQ ID No: 187) and 2DL5_SBT_Ex7_R (5'-CCTTGGTCCAGGGACCATC-3', nt8201~nt8219, SEQ ID No: 188), respectively;

The forward and reverse sequencing primers for exon 8 of KIR2DL5 are 2DL5_SBT_Ex8_F (5'-CACCTACGGC-CTCCCGCTG-3', nt8480~nt8498, SEQ ID No: 189) and 2DL5_SBT_Ex8_R (5'-GAGGGTGCTCACATTCTTCAA-3', nt8680~nt8700, SEQ ID No: 190), respectively;

The forward and reverse sequencing primers for exon 9 of KIR2DL5 are 2DL5_SBT_Ex9_F (5'-TGCCGGGGACA-GAACAGTG-3', nt8600~nt8618, SEQ ID No: 191) and 2DL5_SBT_Ex9_R (5'-CTCAAGGCCTGACTGTGGT-GCTT-3', nt8899~nt8921, SEQ ID No: 192), respectively.

(6) The forward and reverse sequencing primers for exon 1 of KIR2DS1 are 2DS1_SBT_Ex1_F (5'-CTCCCATGAT-GTGGTCAAC-3', nt-109~nt-91, SEQ ID No: 193) and 2DS1_SBT_Ex1_R (5'-TCTCCAACCCCACACTCCC-3', nt61~nt79, SEQ ID No: 194), respectively;

The forward and reverse sequencing primers for exon 2 of KIR2DS1 are 2DS1_SBT_Ex2_F (5'-TTCTTGGGTGCA-GGTAGGC-3', nt855~nt873, SEQ ID No: 195) and 2DS1_SBT_Ex2_R (5'-CTGCCAAGGGAATGAAAGG-3', nt1185~nt1203, SEQ ID No: 196), respectively;

The forward and reverse sequencing primers for exon 4 of KIR2DS1 are 2DS1_SBT_Ex4_F (5'-GGTGCCATG-GATGGGATGA-3', nt3423~nt3441, SEQ ID No: 197) and 2DS1_SBT_Ex4_R (5'-CAAGTCCTGGATCATTCAC-3', nt3827~nt3845, SEQ ID No: 198), respectively;

The forward and reverse sequencing primers for exon 5 of KIR2DS1 are 2DS1_SBT_Ex5_F (5'-AGAGCA-GGGGAGTGAGTTC-3', nt5221~nt5239, SEQ ID No: 199) and 2DS1_SBT_Ex5_R (5'-GGCTCTAGGATCATAG-GAC-3', nt5628~nt5646, SEQ ID No: 200), respectively;

The forward and reverse sequencing primers for exon 6 of KIR2DS1 are 2DS1_SBT_Ex6_F (5'-TCCT-CAAAGATTTCCACTGAGTG-3', nt8684~nt8706, SEQ ID No: 201) and 2DS1_SBT_Ex6_R (5'-GTGAGATGCT-GAGTCAACGC-3', nt8871~nt8890, SEQ ID No: 202), respectively;

The forward and reverse sequencing primers for exon 7 of KIR2DS1 are 2DS1_SBT_Ex7_F (5'-GTGGTTACCTGC-CAATCAAG-3', nt12981~nt13000, SEQ ID No: 203) and 2DS1_SBT_Ex7_R (5'-TGAGGAACACACATCCGCGT-3', nt13236~nt13255, SEQ ID No: 204), respectively;

The forward and reverse sequencing primers for exon 8 of KIR2DS1 are 2D51_SBT_Ex8_F (5'-ATGGCCTCCCCCT-GTTTGT-3', nt13547~nt13565, SEQ ID No: 205) and 2DS1_SBT_Ex8_R (5'-GGGAATAAGACTAGCCACG-3', nt13713~nt13731, SEQ ID No: 206), respectively;

The forward and reverse sequencing primers for exon 9 of KIR2DS1 are 2DS1_SBT_Ex9_F (5'-CTCCTCGGCCCA-GCCTCGT-3', nt13697~nt13715, SEQ ID No: 207) and 2DS1_SBT_Ex9_R (5'-TCCCCTCAAGGCCTGACTG-3', nt13971~nt13989, SEQ ID No: 208), respectively.

(7) The forward and reverse sequencing primers for exon 1 of KIR2DS2 are 2DS2_SBT_Ex1_F (5'-ATAACATCCT-GTGCGCTGC-3', nt-63~nt-45, SEQ ID No: 209) and 2DS2_SBT_Ex1_R (5'-CCAACTCTGGGCCCCGATC-3', nt78~nt96, SEQ ID No: 210), respectively;

The forward and reverse sequencing primers for exon 2 of KIR2DS2 are 2DS2_SBT_Ex2_F (5'-AAGGGAGTCCTG-GTTTGCC-3', nt772~nt790, SEQ ID No: 211) and 2DS2_SBT_Ex2_R (5'-GTCAGAAATGTGGGCCGAG-3', nt981~nt999, SEQ ID No: 212), respectively;

The forward and reverse sequencing primers for exon 4 of KIR2DS2 are 2DS2_SBT_Ex4_F (5'-CACCTTCTAAACT-CACAACC-3', nt3268~nt3287, SEQ ID No: 213) and 2DS2_SBT_Ex4_R (5'-CACTCTGCAGCCCAATGAC-3', nt3624~nt3642, SEQ ID No: 214), respectively;

The forward and reverse sequencing primers for exon 5 of KIR2DS2 are 2DS2_SBT_Ex5_F (5'-AGAGCA-GGGGAGTGAGTTC-3', nt5030~nt5048, SEQ ID No: 215) and 2DS2_SBT_Ex5_R (5'-GAAGCTCCTCA-GCTAAGGC-3', nt5453~nt5471, SEQ ID No: 216), respectively;

The forward and reverse sequencing primers for exon 6 of KIR2DS2 are 2DS2_SBT_Ex6_F (5'-CCAGGGCCCAAT-ATTAGAT-3', nt8465~nt8483, SEQ ID No: 217) and 2DS2_SBT_Ex6_R (5'-TGAGTCAACGCCTGAATCC-3', nt8686~nt8704, SEQ ID No: 218), respectively;

The forward and reverse sequencing primers for exon 7 of KIR2DS2 are 2DS2_SBT_Ex7_F (5'-GCCAAT-CAAGAAATGCGAG-3', nt12815~nt12833, SEQ ID No: 219) and 2DS2_SBT_Ex7_R (5'-GTCCTGCCTCTGTG-GCTCC-3', nt13108~nt13126, SEQ ID No: 220), respectively;

The forward and reverse sequencing primers for exon 8 of KIR2DS2 are 2DS2_SBT_Ex8_F (5'-ATGAGGACCCA-GAAGTGCC-3', nt13407~nt13425, SEQ ID No: 221) and 2DS2_SBT_Ex8_R (5'-CCTCCTGATGGTCTTGTTC-3', nt13621~nt13639, SEQ ID No: 222), respectively;

The forward and reverse sequencing primers for exon 9 of KIR2DS2 are 2DS2_SBT_Ex9_F (5'-AGGTAGGTGCTC-CTCGGCC-3', nt13512~nt13530, SEQ ID No: 223) and 2DS2_SBT_Ex9_R (5'-AGAAGATCCCCTCAAGGCC-3', nt13801~nt13819, SEQ ID No: 224), respectively.

(8) The forward and reverse sequencing primers for exon 1 of KIR2DS3 are 2DS3_SBT_Ex1_F (5'-CAGGGAGC-CAAATAACATC-3', nt-75~nt-57, SEQ ID No: 225) and 2DS3_SBT_Ex1_R (5'-CGCTCCCTCCCTCTATTCC-3', nt49~nt67, SEQ ID No: 226), respectively;

The forward and reverse sequencing primers for exon 2 of KIR2DS3 are 2DS3_SBT_Ex2_F (5'-GCCGAGAGCCCT-GTTCTTG-3', nt1182~nt1200, SEQ ID No: 227) and 2DS3_SBT_Ex2_R (5'-ACAGGACTTCCCTCCCGTT-3', nt1432~nt1450, SEQ ID No: 228), respectively;

The forward and reverse sequencing primers for exon 4 of KIR2DS3 are 2DS3_SBT_Ex4_F (5'-AGAGAGACACCT-TCTAAAT-3', nt3780~nt3798, SEQ ID No: 229) and 2DS3_SBT_Ex4_R (5'-ATCATTCACTCTGTGTCCG-3', nt4152~nt4170, SEQ ID No: 230), respectively;

The forward and reverse sequencing primers for exon 5 of KIR2DS3 are 2DS3_SBT_Ex5_F (5'-AGGAAGATCCTC-CATAAGG-3', nt5596~nt5614, SEQ ID No: 231) and 2DS3_SBT_Ex5_R (5'-GGCTCTAGGATCATAGGAC-3', nt5957~nt5975, SEQ ID No: 232), respectively;

The forward and reverse sequencing primers for exon 6 of KIR2DS3 are 2DS3_SBT_Ex6_F (5'-TCCCAGGGC-CCAATATTAG-3', nt8968~nt8986, SEQ ID No: 233) and 2DS3_SBT_Ex6_R (5'-CACTGAGCCCTGTGTTGGG-3', nt9291~nt9309, SEQ ID No: 234), respectively;

The forward and reverse sequencing primers for exon 7 of KIR2DS3 are 2DS3_SBT_Ex7_F (5'-GTGCTTGTC-CTAAAGAGACGT-3', nt13284~nt13304, SEQ ID No: 235) and 2DS3_SBT_Ex7_R (5'-TGAGTGGCTGCA-GGGGACG-3', nt13709~nt13727, SEQ ID No: 236), respectively;

The forward and reverse sequencing primers for exon 8 of KIR2DS3 are 2DS3_SBT_Ex8_F (5'-GACCTCAGGCAC-CTATGGC-3', nt13862~nt13880, SEQ ID No: 237) and 2DS3_SBT_Ex8_R (5'-GCTGAGTGAGGGAGGGTGC-3', nt14082~nt14100, SEQ ID No: 238), respectively;

The forward and reverse sequencing primers for exon 9 of KIR2DS3 are 2DS3_SBT_Ex9_F (5'-CGGCCCAGC-CTCGTGGCTA-3', nt14031~nt14049, SEQ ID No: 239) and 2DS3_SBT_Ex9_R (5'-TGTCTTGGGCCTCT-GAGAAGGGG-3', nt14196~nt14218, SEQ ID No: 240), respectively.

(9) The forward and reverse sequencing primers for exon 1 of KIR2DS4 are 2DS4_SBT_Ex1_F (5'-ACCAT-GTCGCTCATGGTC-3', nt-3~nt15, SEQ ID No: 241) and 2DS4_SBT_Ex1_R (5'-GGCTCATCACTCCATCTCT-3', nt148~nt166, SEQ ID No: 242), respectively;

The forward and reverse sequencing primers for exon 2 of KIR2DS4 are 2DS4_SBT_Ex2_F (5'-GAAGGGGCTGGC-TATCAAG-3', nt2218~nt2236, SEQ ID No: 243) and 2DS4_SBT_Ex2_R (5'-GACTTCCCTCCCGTTTCAG-3', nt2404~nt2422, SEQ ID No: 244), respectively;

The forward and reverse sequencing primers for exon 4 of KIR2DS4 are 2DS4_SBT_Ex4_F (5'-AGAGAGACACCT-TCTAAAC-3', nt4774~nt4792, SEQ ID No: 245) and 2DS4_SBT_Ex4_R (5'-CACCTGGGTCTCCAAGTCC-3', nt5168~nt5186, SEQ ID No: 246), respectively;

The forward and reverse sequencing primers for exon 5 of KIR2DS4 are 2DS4_SBT_Ex5_F (5'-AGTTCTCAG-GTCAGGTGTG-3', nt6589~nt6607, SEQ ID No: 247) and 2DS4_SBT_Ex5_R (5'-GGAAGCTCCTCAGCTAAGG-3', nt7001~nt7019, SEQ ID No: 248), respectively;

The forward and reverse sequencing primers for exon 6 of KIR2DS4 are 2DS4_SBT_Ex6_F (5'-CTGGACTCCCA-GGGCCCAATG-3', nt10004~nt10024, SEQ ID No: 249) and 2DS4_SBT_Ex6_R (5'-TTCCACCTCCCCA-GGGTTC-3', nt10209~nt10227, SEQ ID No: 250), respectively;

The forward and reverse sequencing primers for exon 7 of KIR2DS4 are 2DS4_SBT_Ex7_F (5'-CGCCATTTGGGT-GCTTGTC-3', nt14317~nt14335, SEQ ID No: 251) and 2DS4_SBT_Ex7_R (5'-GGTGAGGAACACACATCCG-3', nt14611~nt14629, SEQ ID No: 252), respectively;

The forward and reverse sequencing primers for exon 8 of KIR2DS4 are 2DS4_SBT_Ex8_F (5'-AGTCTGCTGTTG-GCAACTG-3', nt14883~nt14901, SEQ ID No: 253) and 2DS4_SBT_Ex8_R (5'-CCTCCTGATGGTCTTGTTC-3', nt15169~nt15187, SEQ ID No: 254), respectively;

The forward and reverse sequencing primers for exon 9 of KIR2DS4 are 2DS4_SBT_Ex9_F (5'-CTCGGCCCAGC-CTCGTGGC-3', nt15072~nt15090, SEQ ID No: 255) and 2DS4_SBT_Ex9_R (5'-CAACTTTGGATCTGGGCTC-3', nt15304~nt15322, SEQ ID No: 256), respectively.

(10) The forward and reverse sequencing primers for exon 1 of KIR2DS5 are 2DS5_SBT_Ex1_F (5'-GGCGC-CAAATAACATCCTG-3', nt-72~nt-54, SEQ ID No: 257) and 2DS5_SBT_Ex1_R (5'-GCCCAGATCTCCATC-CCCG-3', nt68~nt86, SEQ ID No: 258), respectively;

The forward and reverse sequencing primers for exon 2 of KIR2DS5 are 2DS5_SBT_Ex2_F (5'-GGCACTGAGKGT-GAGTTTC-3', nt1383~nt1401, SEQ ID No: 259) and 2DS5_SBT_Ex2_R (5'-TGACAGGACTTCCCTCCCG-3', nt1606~nt1624, SEQ ID No: 260), respectively;

The forward and reverse sequencing primers for exon 4 of KIR2DS5 are 2DS5_SBT_Ex4_F (5'-GACACCT-TCTAAATTCACAAAC-3', nt3958~nt3979, SEQ ID No: 261) and 2DS5_SBT_Ex4_R (5'-CTCTGCATCCCAAT-GACAATG-3', nt4315~nt4335, SEQ ID No: 262), respectively;

The forward and reverse sequencing primers for exon 5 of KIR2DS5 are 2DS5_SBT_Ex5_F (5'-CCTCCCTGAG-GAAAATGCC-3', nt5786~nt5804, SEQ ID No: 263) and 2DS5_SBT_Ex5_R (5'-TCATAGGACATGGGACAGC-3', nt6129~nt6147, SEQ ID No: 264), respectively;

The forward and reverse sequencing primers for exon 6 of KIR2DS5 are 2DS5_SBT_Ex6_F (5'-CAGGGCCCAAT-ATTAGATAAC-3', nt9147~nt9167, SEQ ID No: 265) and 2DS5_SBT_Ex6_R (5'-GGAGTATCTGGAGTTCG-GAGA-3', nt9426~nt9446, SEQ ID No: 266), respectively;

The forward and reverse sequencing primers for exon 7 of KIR2DS5 are 2DS5_SBT_Ex7_F (5'-CTGTCAAT-CAAGAAATGCGAG-3', nt13495~nt13515, SEQ ID No: 267) and 2DS5_SBT_Ex7_R (5'-GGAACACACAC-CCGCGTGC-3', nt13740~nt13758, SEQ ID No: 268), respectively;

The forward and reverse sequencing primers for exon 8 of KIR2DS5 are 2DS5_SBT_Ex8_F (5'-AGATAGAATGTCT-GAGTCTGC-3', nt14003~nt14023, SEQ ID No: 269) and 2DS5_SBT_Ex8_R (5'-ACACAGTGATCCAATTATGCG-3', nt14329~nt14349, SEQ ID No: 270), respectively;

The forward and reverse sequencing primers for exon 9 of KIR2DS5 are 2DS5_SBT_Ex9_F (5'-GGTAGGTGCTC-CTCGGCCC-3', nt14195~nt14213, SEQ ID No: 271) and 2DS5_SBT_Ex9_R (5'-ATGGGAGCTGGCAACCCGG-3', nt14528~nt14546, SEQ ID No: 272), respectively.

(11) The forward and reverse sequencing primers for exon 1 of KIR3DL1 are 3DL1_SBT_Ex1_F (5'-CAGGGCGC-CAAATAACATC-3', nt-74~nt-56, SEQ ID No: 273) and 3DL1_SBT_Ex1_R (5'-CAGATCTCCATCCCCGCAC-3', nt65~nt83, SEQ ID No: 274), respectively;

The forward and reverse sequencing primers for exon 2 of KIR3DL1 are 3DL1_SBT_Ex2_F (5'-AGGGCCTGGCT-GCCAAGAC-3', nt940~nt958, SEQ ID No: 275) and 3DL1_SBT_Ex2_R (5'-AATGTGGGCCGAGCATCCG-3', nt1182~nt1200, SEQ ID No: 276), respectively;

The forward and reverse sequencing primers for exon 3 of KIR3DL1 are 3DL1_SBT_Ex3_F (5'-GGGGAGAATCT-TCTGGGCACT-3', nt1736~nt1756, SEQ ID No: 277) and 3DL1_SBT_Ex3_R (5'-TGATGGGACCCTGACGGAC-3', nt2167~nt2185, SEQ ID No: 278), respectively;

The forward and reverse sequencing primers for exon 4 of KIR3DL1 are 3DL1_SBT_Ex4_F (5'-TGGAGGCACCTG-CACCAGG-3', nt3052~nt3070, SEQ ID No: 278) and 3DL1_SBT_Ex4_R (5'-TGGTACAGACCTCACCAAG-3', nt3633~nt3651, SEQ ID No: 280), respectively;

The forward and reverse sequencing primers for exon 5 of KIR3DL1 are 3DL1_SBT_Ex5_F (5'-CAGGTAT-GAGGGGAGCTATG-3', nt5001~nt5020, SEQ ID No: 281) and 3DL1_SBT_Ex5_R (5'-CCTGTCTGCCATCCT-GCGC-3', nt5490~nt5508, SEQ ID No: 282), respectively;

The forward and reverse sequencing primers for exon 6 of KIR3DL1 are 3DL1_SBT_Ex6_F (5'-AAGCACCCT-CATTTCCTCAC-3', nt8485~nt8504, SEQ ID No: 283) and 3DL1_SBT_Ex6_R (5'-CAACACTTGCATCCAAGGC-3', nt8631~nt8649, SEQ ID No: 284), respectively;

The forward and reverse sequencing primers for exon 7 of KIR3DL1 are 3DL1_SBT_Ex7_F (5'-CCCGC-CATCTGGGTGCTTG-3', nt12734~nt12752, SEQ ID No: 285) and 3DL1_SBT_Ex7_R (5'-TCCTGCTTCCCCA-CATGGC-3', nt13001~nt13019, SEQ ID No: 286), respectively;

The forward and reverse sequencing primers for exon 8 of KIR3DL1 are 3DL1_SBT_Ex8_F (5'-CCAGAAGTGC-CCTCCGAGC-3', nt13382~nt13400, SEQ ID No: 287) and 3DL1_SBT_Ex8_R (5'-TGTTTGGGAATAACACTAGCC-3', nt13507~nt13527, SEQ ID No: 288), respectively;

The forward and reverse sequencing primers for exon 9 of KIR3DL1 are 3DL1_SBT_Ex9_F (5'-CGTGGCTAGTGT-TATTCCC-3', nt13504~nt13522, SEQ ID No: 289) and 3DL1_SBT_Ex9_R (5'-ATGGGAGCTGGCAACTCGG-3', nt13833~nt13851, SEQ ID No: 290), respectively.

(12) The forward and reverse sequencing primers for exon 1 of KIR3DL2 are 3DL2_SBT_Ex1_F (5'-GC-CAAATAACATCCTGTGCGC-3', nt-68~nt-48, SEQ ID No: 291) and 3DL2_SBT_Ex1_R (5'-TAGGCCGA-GATCTCCATCC-3', nt71~nt89, SEQ ID No: 292), respectively;

The forward and reverse sequencing primers for exon 2 of KIR3DL2 are 3DL2_SBT_Ex2_F (5'-GAGGCTAAGTT-TACCTTCAGC-3', nt624~nt644, SEQ ID No: 293) and 3DL2_SBT_Ex2_R (5'-GACTTCCCTCCTGTTTCAG-3', nt834~nt852, SEQ ID No: 294), respectively;

The forward and reverse sequencing primers for exon 3 of KIR3DL2 are 3DL2_SBT_Ex3_F (5'-GGCCCAGCACT-GTGGTGCC-3', nt1553~nt1571, SEQ ID No: 295) and 3DL2_SBT_Ex3_R (5'-GCCCATTTCCCCTGTATTC-3', nt1930~nt1948, SEQ ID No: 296), respectively;

The forward and reverse sequencing primers for exon 4 of KIR3DL2 are 3DL2_SBT_Ex4_F (5'-GAGAGATGCCT-TCTAAACT-3', nt3235~nt3253, SEQ ID No: 297) and 3DL2_SBT_Ex4_R (5'-TCTCCATAAGAATCCCACGCT-3', nt3663~nt3683, SEQ ID No: 298), respectively;

The forward and reverse sequencing primers for exon 5 of KIR3DL2 are 3DL2_SBT_Ex5_F (5'-CCTCCCTGAG-GAAACTGCC-3', nt5111~nt5129, SEQ ID No: 299) and 3DL2_SBT_Ex5_R (5'-GAAAGAGCCGAAGCATCTG-3', nt5361~nt5379, SEQ ID No: 300), respectively;

The forward and reverse sequencing primers for exon 6 of KIR3DL2 are 3DL2_SBT_Ex6_F (5'-CAACCT-CAAAGATTTCCATTG-3', nt8530~nt8550, SEQ ID No: 301) and 3DL2_SBT_Ex6_R (5'-CAACACTTGCATC-CAAGGC-3', nt8707~nt8725, SEQ ID No: 302), respectively;

The forward and reverse sequencing primers for exon 7 of KIR3DL2 are 3DL2_SBT_Ex7_F (5'-GAGATGTTCCAT-GTGGTTACC-3', nt15231~nt15251, SEQ ID No: 303) and 3DL2_SBT_Ex7_R (5'-GGAACACACACCCGCGTGC-3', nt15494~nt15512, SEQ ID No: 304), respectively;

The forward and reverse sequencing primers for exon 8 of KIR3DL2 are 3DL2_SBT_Ex8_F (5'-TCTGAGTCTGGAT-GTTGGC-3', nt15764~nt15782, SEQ ID No: 305) and 3DL2_SBT_Ex8_R (5'-GGGTCTTGTTCATCAGAGTCC-3', nt16046~nt16066, SEQ ID No: 306), respectively;

The forward and reverse sequencing primers for exon 9 of KIR3DL2 are 3DL2_SBT_Ex9_F (5'-CCTCGGCCCAGC- CTCACGG-3', nt15957~nt15975, SEQ ID No: 307) and 3DL2_SBT_Ex9_R (5'-GACTGTGGTGCTCGTGGGC-3', nt16216~nt16234, SEQ ID No: 308), respectively.

(13) The forward and reverse sequencing primers for exon 1 of KIR3DL3 are 3DL3_SBT_Ex1_F (5'-ACAACATCCT-GTGTGCTGCTGAA-3', nt-63~nt-41, SEQ ID No: 309) and 3DL3_SBT_Ex1_R (5'-TCCCTCCCTCGATTCCCTT-3', nt46~nt64, SEQ ID No: 310), respectively;

The forward and reverse sequencing primers for exon 2 of KIR3DL3 are 3DL3_SBT_Ex2_F (5'-GATGTACAGATG-GATCATC-3', nt672~nt690, SEQ ID No: 311) and 3DL3_SBT_Ex2_R (5'-GTCAACCCCTGTGTCGCCTG-3', nt815~nt835, SEQ ID No: 312), respectively;

The forward and reverse sequencing primers for exon 3 of KIR3DL3 are 3DL3_SBT_Ex3_F (5'-GCTCCACATCCTC-CTCTCT-3', nt1474~nt1492, SEQ ID No: 313) and 3DL3_SBT_Ex3_R (5'-ATCCCCCTTTACCCCAAAT-3', nt1905~nt1923, SEQ ID No: 314), respectively;

The forward and reverse sequencing primers for exon 4 of KIR3DL3 are 3DL3_SBT_Ex4_F (5'-GGGAAGCCT-CACTTATTTCAG-3', nt2996~nt3016, SEQ ID No: 315) and 3DL3_SBT_Ex4_R (5'-ACCTGGGGCTTCCA-GTCCT-3', nt3431~nt3449, SEQ ID No: 316), respectively;

The forward and reverse sequencing primers for exon 5 of KIR3DL3 are 3DL3_SBT_Ex5_F (5'-GAGAGCTGT-GACAASGAAG-3', nt4900~nt4918, SEQ ID No: 317) and 3DL3_SBT_Ex5_R (5'-GCAGGAAGCTCCTCAGCTA-3', nt5294~nt5312, SEQ ID No: 318), respectively;

The forward and reverse sequencing primers for exon 7 of KIR3DL3 are 3DL3_SBT_Ex7_F (5'-GTGAGACAAT-TCATATAGA-3', nt10650~nt10668, SEQ ID No: 319) and 3DL3_SBT_Ex7_R (5'-TGCTTCCCCACATGGCCCT-3', nt10852~nt10870, SEQ ID No: 320), respectively;

The forward and reverse sequencing primers for exon 8 of KIR3DL3 are 3DL3_SBT_Ex8_F (5'-GACCTCAGGCAC-CTATGGC-3', nt11178~nt11196, SEQ ID No: 321) and 3DL3_SBT_Ex8_R (5'-GAGTGAGGGAGGGTGCTCA-3', nt11395~nt11413, SEQ ID No: 322), respectively;

The forward and reverse sequencing primers for exon 9 of KIR3DL3 are 3DL3_SBT_Ex9_F (5'-CRTGGCTAGTCTT-ATTCCC-3', nt11358~nt11376, SEQ ID No: 323) and 3DL3_SBT_Ex9_R (5'-CCCTAGAAGATCCCATCAA-3', nt11627~nt11645, SEQ ID No: 324), respectively.

(14) The forward and reverse sequencing primers for exon 1 of KIR3DS1 are 3DS1_SBT_Ex1_F (5'-AAGCCAT-GCTCCGCTCTTG-3', nt-181~nt-163, SEQ ID No: 325) and 3DS1_SBT_Ex1_R (5'-CAGATCTCCATCCCCG-CAC-3', nt65~nt83, SEQ ID No: 326), respectively;

The forward and reverse sequencing primers for exon 2 of KIR3DS1 are 3D51_SBT_Ex2_F (5'-AGTGGGGGCA-GCAGGGTG-3', nt968~nt985, SEQ ID No: 327) and 3DS1_SBT_Ex2_R (5'-AATGTGGGCCGAGCATCCG-3', nt1182~nt1200, SEQ ID No: 328), respectively;

The forward and reverse sequencing primers for exon 3 of KIR3DS1 are 3D51_SBT_Ex3_F (5'-GGGGAGAATCT-TCTGGGCACT-3', nt1735~nt1755, SEQ ID No: 329) and 3DS1_SBT_Ex3_R (5'-TGATGGGACCCTGACGGAC-3', nt2166~nt2184, SEQ ID No: 330), respectively;

The forward and reverse sequencing primers for exon 4 of KIR3DS1 are 3DS1_SBT_Ex4_F (5'-GGAGAGAGACA-GACACGGG-3', nt3485~nt3503, SEQ ID No: 331) and 3DS1_SBT_Ex4_R (5'-TGGTACAGACCTCACCAAG-3', nt4007~nt4025, SEQ ID No: 332), respectively;

The forward and reverse sequencing primers for exon 5 of KIR3DS1 are 3D51_SBT_Ex5_F (5'-CAGGTGT-GAGGGGAGCTGT-3', nt5403~nt5421, SEQ ID No: 333) and 3DS1_SBT_Ex5_R (5'-CCTGTCTGCCATCCTGCGC-3', nt5892~nt5910, SEQ ID No: 334), respectively;

The forward and reverse sequencing primers for exon 6 of KIR3DS1 are 3DS1_SBT_Ex6_F (5'-TCAAGACA-GTGGGCATCGCAC-3', nt8763~nt8783, SEQ ID No: 335) and 3D51_SBT_Ex6_R (5'-GGGAGGTTTGAGC-CAACGCTT-3', nt9045~nt9065, SEQ ID No: 336), respectively;

The forward and reverse sequencing primers for exon 7 of KIR3DS1 are 3DS1_SBT_Ex7_F (5'-CGCTGTATGTGGT-TACCTGTG-3', nt13165~nt13185, SEQ ID No: 337) and 3DS1_SBT_Ex7_R (5'-GGTGAGGAACACACACCCG-3', nt13432~nt13450, SEQ ID No: 338), respectively;

The forward and reverse sequencing primers for exon 8 of KIR3DS1 are 3D51_SBT_Ex8_F (5'-CCAGAAGTGC-CCTCCGAGC-3', nt13784~nt13802, SEQ ID No: 339) and 3DS1_SBT_Ex8_R (5'-GCTGAGTGAGGGAGGGTGC-3', nt13944~nt13962, SEQ ID No: 340), respectively;

The forward and reverse sequencing primers for exon 9 of KIR3DS1 are 3D51_SBT_Ex9_F (5'-CGTGGCTAGTGTT-ATTCCC-3', nt13904~nt13922, SEQ ID No: 341) and 3DS1_SBT_Ex9_R (5'-GGCCTCTGAGAAGGGCGAG-3', nt14055~nt14073, SEQ ID No: 342), respectively.

VIII. All the sequencing reactions can be carried out in a volume of 10 μL containing:

| | |
|---|---|
| 5× BigDye Sequencing Buffer | 2.075 μL, |
| BigDye Terminator 3.1 | 0.25 μL, |
| 10 μM Sequencing Primer | 0.32 μL, |
| Purified PCR Products Diluted 1:3 with ddH$_2$O | 2.0 μL, |
| Add ddH$_2$O to | 10.0 μL. |

IX. The thermocycling parameters for the sequencing reaction are described below:

| | |
|---|---|
| 95° C. | 1 min; |
| 95° C. | 10 Sec, |
| 50° C. | 5 Sec, |
| 60° C. | 4 min, 25 cycles; |
| 4° C. | Infinite. |

Based on the structural features of KIR full genomic sequences, the distribution of single nucleotide polymorphisms in their coding regions and the length of flanking intronic sequence of each exon, the present disclosure has established a scientific and efficient PCR amplification strategy for all the 14 functional KIR genes. We design KIR gene-specific PCR and sequencing primers, and explore the optimal PCR amplification and sequencing conditions. This disclosure allows for simultaneous genotyping of 14 functional KIR genes by SBT, which is suitable for high-resolution level KIR genotyping, population genetics, tissue typing for bone marrow transplant and disease-associated studies.

The contributions of the present disclosure include: for the first time this disclosure has established the method for high-throughput simultaneous sequence-based typing of 14 functional KIR genes at high-resolution level. KIR gene-specific PCR primers with similar annealing temperatures have been designed, which allow for simultaneous PCR amplification of 14 functional KIR genes under the same PCR conditions and make the PCR procedure less time-consuming and labor-consuming. The occurrence of non-specific amplification or co-amplification events has been solved via designing KIR gene-specific PCR primers. Without using the extra commercial KIR-SSP kit, the presence or absence of 14 functional KIR genes can also be identified by agarose gel electrophoresis of PCR products. Based on our KIR SBT method, the entire coding sequence for all the 14 functional KIR genes are sequenced in both direction, the deficiencies existed in previous literatures can be overcome. Moreover, no noise and artifacts are observed in the obtained sequences, which can greatly facilitate the process of KIR allele assignment.

BRIEF DESCRIPTION OF THE DRAWINGS

In order to more clearly illustrate the embodiments of the present disclosure or the prior art solutions, a brief description of the accompanying drawings for use with the illustration of the embodiments or the prior art are provided below. It is obvious that the drawings described below depict merely some embodiments of the disclosure and those of

TABLE 3

Figure 1:
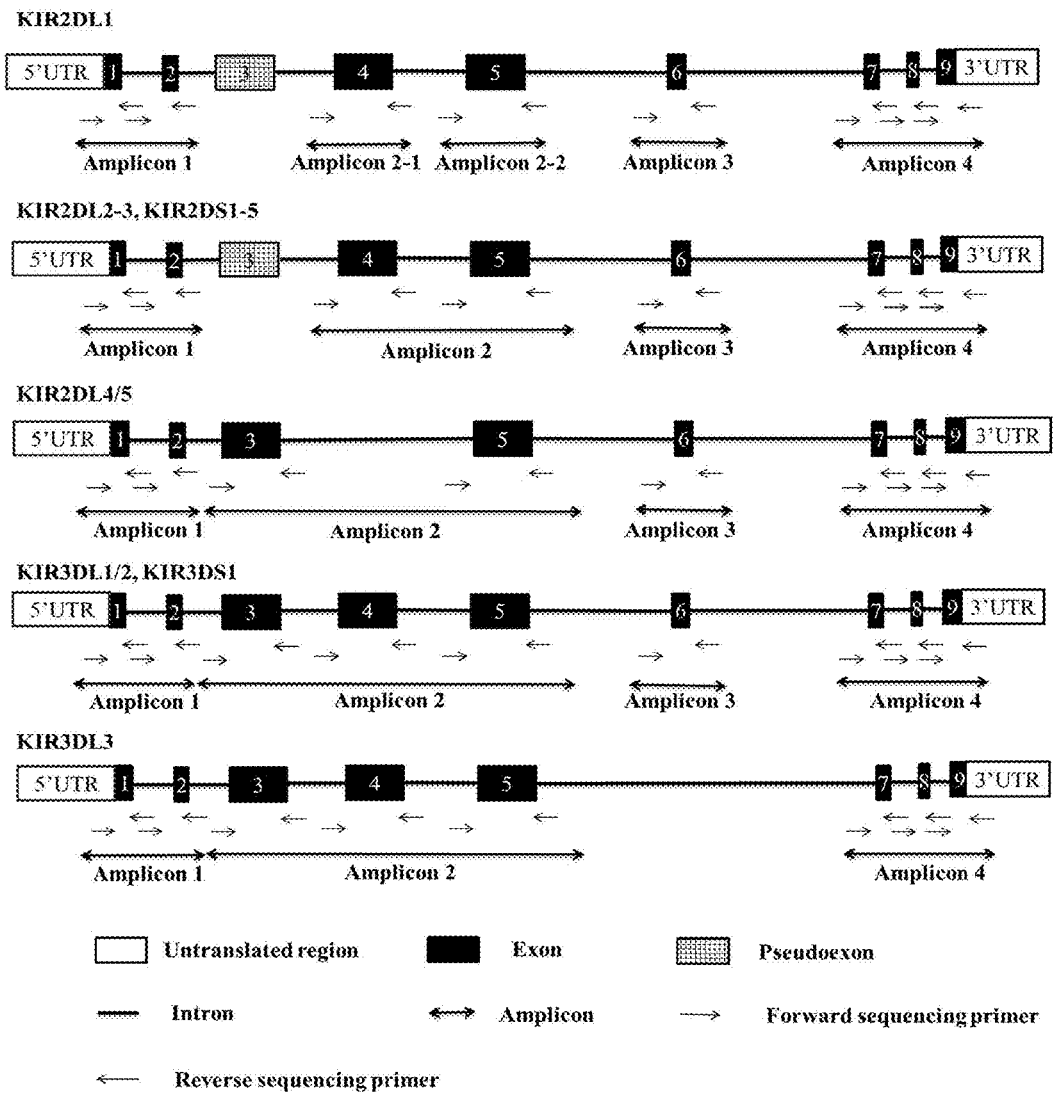

Structure of the Coding Region and Length of Exons of the 14 Functional KIR Genes

| KIR Protein KIR Gene | Leader Peptides | | Extracellular Domains | | | Stem | Transmembrane and Cytoplasmic Region | | | Length of Coding Sequence (bp) |
|---|---|---|---|---|---|---|---|---|---|---|
| | Exon 1 (bp) | Exon 2 (bp) | Exon 3 (bp) | Exon 4 (bp) | Exon 5 (bp) | Exon 6 (bp) | Exon 7 (bp) | Exon 8 (bp) | Exon 9 (bp) | |
| 2DL1 | 34 | 36 | Pseudoex | 300 | 294 | 51 | 102 | 53 | 177 | 1047 |
| 2DL2 | 34 | 36 | Pseudoex | 300 | 294 | 51 | 102 | 53 | 177 | 1047 |
| 2DL3 | 34 | 36 | Pseudoex | 300 | 294 | 51 | 105 | 53 | 177 | 1050 |
| 2DL4 | 40 | 36 | 285 | Del | 294 | 51 | 105 | 53 | 270 | 1134 |
| 2DL5 | 34 | 36 | 285 | Del | 294 | 51 | 105 | 53 | 270 | 1128 |
| 2DS1 | 34 | 36 | Pseudoex | 300 | 294 | 51 | 105 | 53 | 42 | 915 |
| 2DS2 | 34 | 36 | Pseudoex | 300 | 294 | 51 | 105 | 53 | 42 | 915 |
| 2DS3 | 34 | 36 | Pseudoex | 300 | 294 | 51 | 105 | 53 | 42 | 915 |
| 2DS4 | 34 | 36 | Pseudoex | 300 | 294 | 51 | 105 | 53 | 42 | 915 |
| 2DS5 | 34 | 36 | Pseudoex | 300 | 294 | 51 | 105 | 53 | 42 | 915 |
| 3DL1 | 34 | 36 | 285 | 300 | 294 | 51 | 105 | 53 | 177 | 1335 |
| 3DL2 | 34 | 36 | 285 | 300 | 294 | 51 | 105 | 53 | 210 | 1368 |
| 3DL3 | 34 | 36 | 285 | 300 | 294 | Del | 105 | 53 | 126 | 1233 |
| 3DS1 | 34 | 36 | 285 | 300 | 294 | 51 | 105 | 51 | 8 | 1164 |

Del: deleted exon.

TABLE 4

Structure and Length of Non-coding Sequence of the 14 Functional KIR Genes

| KIR Gene | 5'UTR (bp) | Intron 1 (bp) | Intron 2 (bp) | Intron 3 (bp) | Intron 4 (bp) | Intron 5 (bp) | Intron 6 (bp) | Intron 7 (bp) | Intron 8 (bp) | 3'-UTR (bp) | Length of non-coding sequence (bp) | Full genomic sequence (bp) | Length of introns 5 and 6 accounting for % of full genomic sequence |
|---|---|---|---|---|---|---|---|---|---|---|---|---|---|
| 2DL1 | 268 | 964 | Intron 2/3: 2448 | | 1529 | 3154 | 4259 | 462 | 98 | 510 | 13692 | 14739 | 50.3% (7413/14739) |
| 2DL2 | 300 | 908 | Intron 2/3: 2436 | | 1514 | 3272 | 4265 | 462 | 98 | 510 | 13765 | 14812 | 50.9% (7537/14812) |
| 2DL3 | 268 | 908 | Intron 2/3: 2437 | | 1515 | 3250 | 4263 | 462 | 98 | 510 | 13711 | 14761 | 50.9% (7513/14761) |
| 2DL4 | 267 | 199 | 900 | Intron 3/4: 873 | | 2595 | 4242 | 461 | 99 | 407 | 10043 | 11177 | 61.2% (6837/11177) |
| 2DL5 | 489 | 733 | 762 | Intron 3/4: 875 | | 2172 | 2765 | 462 | 100 | 415 | 8773 | 9901 | 49.9% (4937/9901) |
| 2DS1 | 267 | 964 | Intron 2/3: 2448 | | 1525 | 3154 | 4263 | 462 | 98 | 624 | 13805 | 14721 | 50.4% (7417/14721) |
| 2DS2 | 300 | 792 | Intron 2/3: 2436 | | 1518 | 3168 | 4264 | 462 | 98 | 624 | 13662 | 14577 | 51% (7432/14577) |
| 2DS3 | 300 | 1305 | Intron 2/3: 2443 | | 1519 | 3153 | 4265 | 462 | 98 | 645 | 14190 | 15105 | 49.1% (7418/15105) |
| 2DS4 | 267 | 2280 | Intron 2/3: 2461 | | 1552 | 3168 | 4265 | 462 | 98 | 624 | 15177 | 16092 | 46.2% (7433/16092) |
| 2DS5 | 268 | 1498 | Intron 2/3: 2444 | | 1528 | 3155 | 4265 | 462 | 98 | 645 | 14363 | 15278 | 48.6% (7420/15278) |
| 3DL3 | 267 | 999 | 745 | 1113 | 1552 | 3169 | 4282 | 462 | 118 | 504 | 13211 | 14546 | 51.2% (7451/14546) |
| 3DS1 | 267 | 1000 | 744 | 1488 | 1580 | 3170 | 4280 | 462 | 98 | 679 | 13768 | 14932 | 49.9% (7450/14932) |
| 3DL3 | 268 | 710 | 742 | 1464 | 1572 | 3166 | 6675 | 460 | 99 | 485 | 15641 | 17009 | 57.9% (9841/17009) |
| 3DL3 | 320 | 677 | 770 | 1273 | 1578 | Intron 5/6: 5466 | | 462 | 98 | 537 | 11181 | 12414 | 44.0% (5466/12414) |

TABLE 5

Alleles of Functional KIR Gene Released in the IPD-KIR Database (Release 2.6.0)

| Gene | 2DS1 | 2DL2 | 2DL3 | 2DL4 | 2DL5 | 2DS1 | 2DS2 | 2DS3 | 2DS4 | 2DS5 | 3DL1 | 3DS1 | 3DL2 | 3DL3 | Total |
|---|---|---|---|---|---|---|---|---|---|---|---|---|---|---|---|
| Number of KIR alleles | 48 | 30 | 55 | 52 | 48 | 16 | 22 | 15 | 31 | 18 | 110 | 30 | 112 | 111 | 698 |
| Number of Null Alleles | 1 | 0 | 1 | 0 | 0 | 0 | 0 | 1 | 0 | 0 | 2 | 1 | 1 | 0 | 7 | ordinary skill in the art can obtain other drawings based on the arrangements shown in these drawings without making inventive efforts.

FIG. 1 is the technical strategy illustrating the simultaneous sequence-based typing (SBT) method for all 14 functional KIR genes, according to which:

3~5 pairs of KIR gene-specific PCR primers (except that three pairs of PCR primers are used for KIR3DL3 and five pairs of PCR primers are used for KIR2DL1, four pairs of KIR gene-specific PCR primers are used for each of other functional KIR genes) are used to amplify the complete coding sequence of each functional KIR gene. The nucleotide sequences of the exons carried by each amplicon were determined in both directions using the specific forward and reverse sequencing primers. As for KIR2DL1~5, 2DS1~5 and KIR3DL3 genes, each KIR gene is sequenced by sixteen specific sequencing primers, respectively. For KIR3DL1~2 and KIR3DS1 genes, each KIR gene is sequenced by eighteen specific sequencing primers, respectively.

Figure 2:
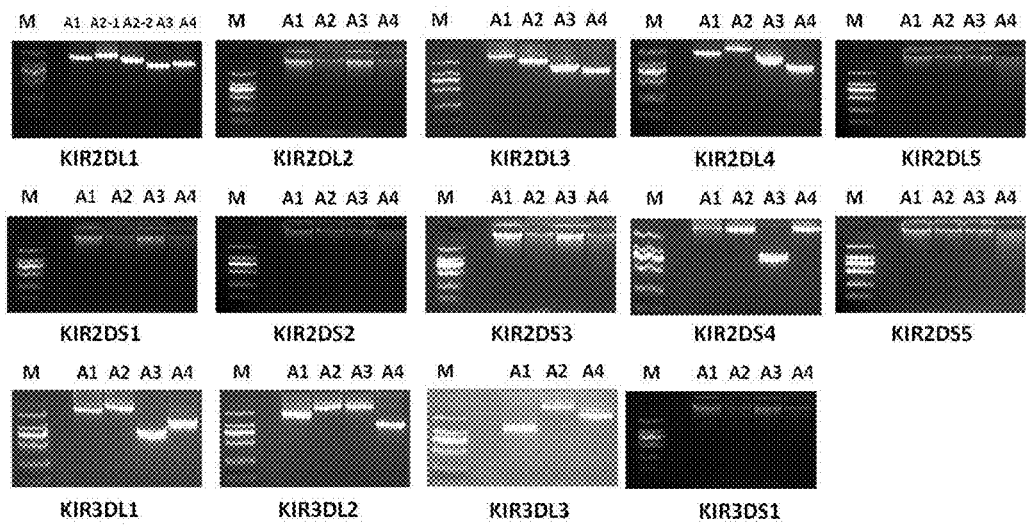

FIG. 2 shows the electrophoresis of the PCR products on a agarose gel for a DNA sample with KIRAA1 profile, according to the first embodiment of this disclosure, wherein, M: DL2000 Marker; A1: Amplicon 1, amplifying the target sequence covering entire exon 1 through exon 2 of each KIR gene. A2: Amplicon 2, as for KIR3DL1~3, 3DS1 and 2DL4~5 genes, PCR ampicon 2 covers the target sequence of entire exon 3 through exon 5; whereas for KIR2DL1~3 and KIR2DS1~5 genes, PCR amplicon 2 covers the target sequence of entire exon 4 through exon 5; In particular, two separate 2DL1-specific PCR amplifications (Amplicon 2-1, Amplicon 2-2) are used for amplifying exon 4 and exon 5 of 2DL1, respectively. A3: Amplicon 3, amplifying the target sequence covering entire exon 6 of each KIR gene; A4: Amplicon 4, amplifying the target sequence covering entire exon 7 through exon 9.

FIGS. 3A to 3H indicate the effect of KIR SBT and allele assignment for a DNA sample with KIRAA1 profile that carrys 7 functional KIR genes (KIR2DL1, 2DL3, 2DL4, 2DS4, 3DL1, 3DL2 and 3DL3). The obtained sequences covering all the exons of each above KIR gene are imported into Assign 3.5 or 4.7 software, the allele level genotype of this sample in the first embodiment is KIR2DL1*00302-2DL3*00101-2DL4*00102,011-2DS4*00101,010-3DL1*00501, 01502-3DL2*00201, 010-3DL3*00901,010.

Figure 4:
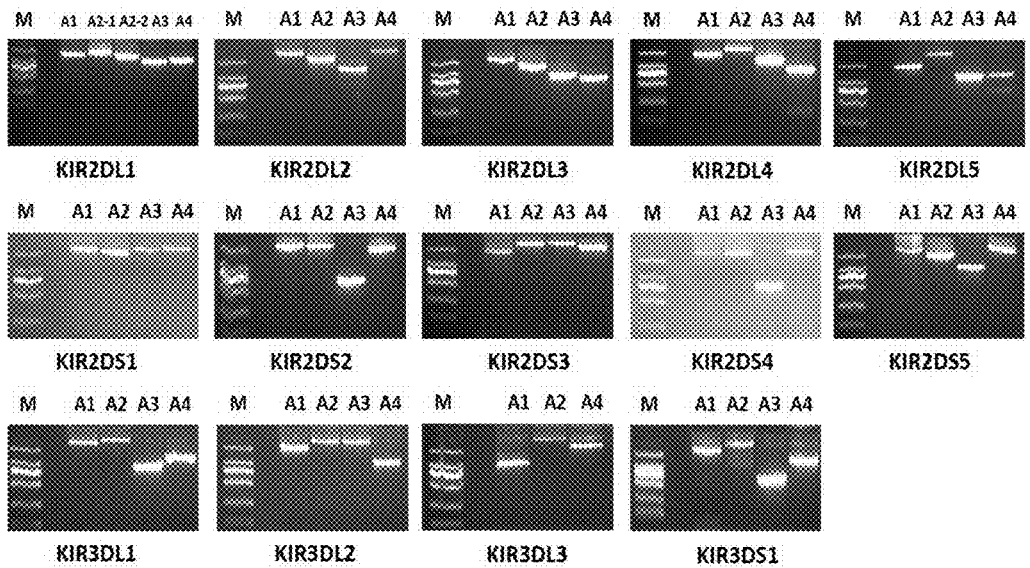

FIG. 4 shows the electrophoresis of the PCR products on an agarose gel for a DNA sample with KIRAB6 profile. According to the second embodiment of this disclosure, wherein, M: DL2000 Marker; A1: Amplicon 1, amplifying the target sequence covering entire exon 1 through exon 2 of each KIR gene; A2: Amplicon 2, as for 3DL1~3, 3DS1, and 2DL4~5 genes, PCR ampicon 2 covers the target sequence of entire exon 3 through exon 5; whereas for KIR2DL1~3 and KIR2DS1~5 genes, PCR amplicon 2 covers the target sequence of entire exon 4 through exon 5; In particular, two separate 2DL1 specific PCR amplifications (Amplicon 2-1, Amplicon 2-2) are used for amplifying exon 4 and exon 5 of 2DL1, respectively; A3: Amplicon 3, amplifying the target sequence covering entire exon 6 of each KIR gene; A4: Amplicon 4, amplifying the target sequence covering entire exon 7 through exon 9.

Figure 5A:
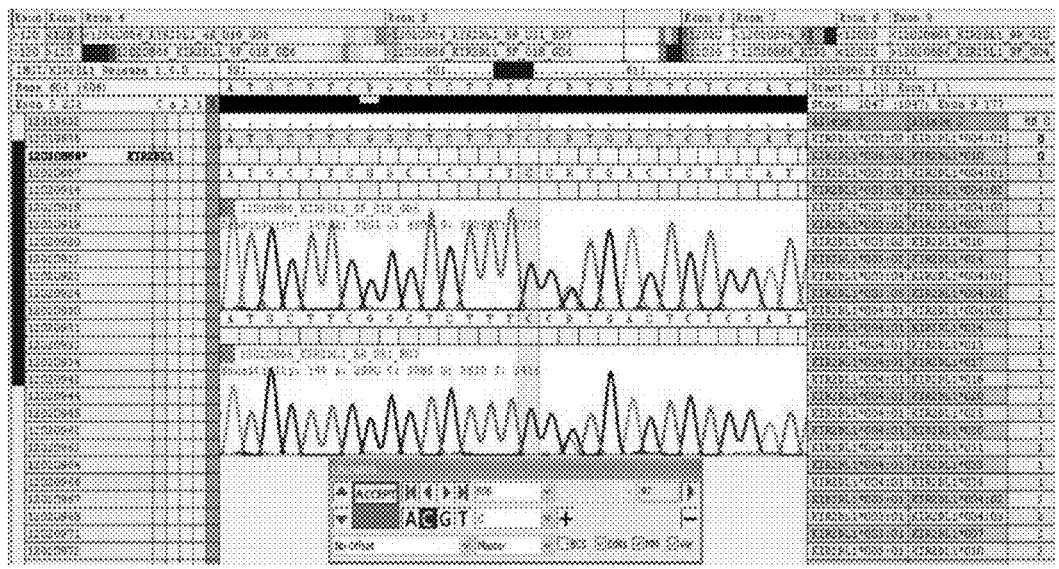
Figure 5B:
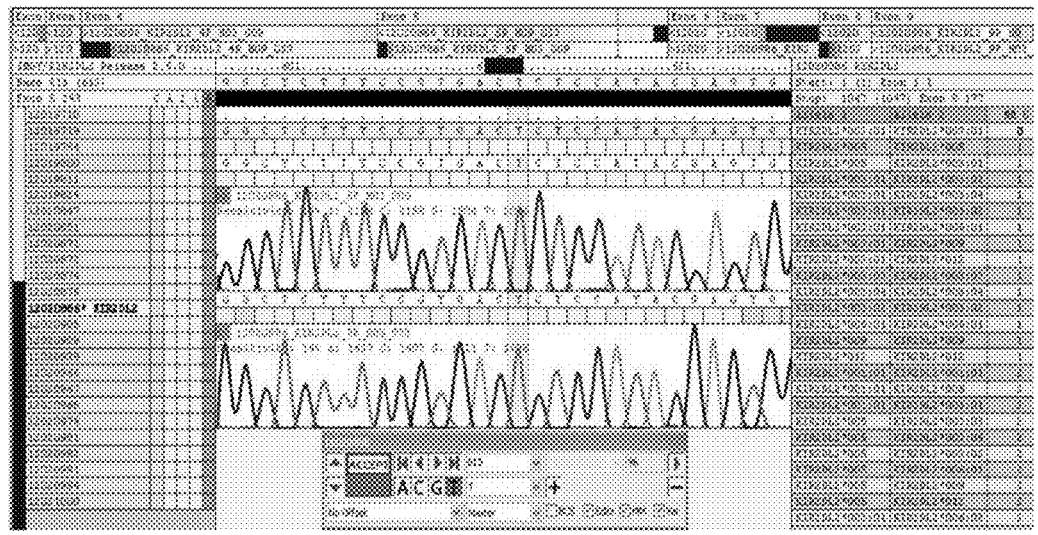
Figure 5C:
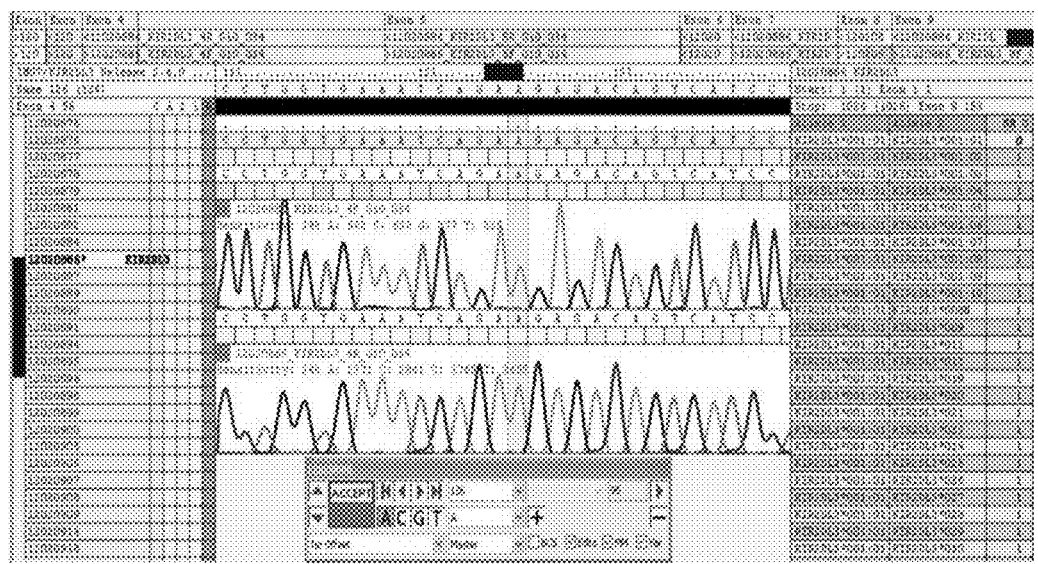
Figure 5D:
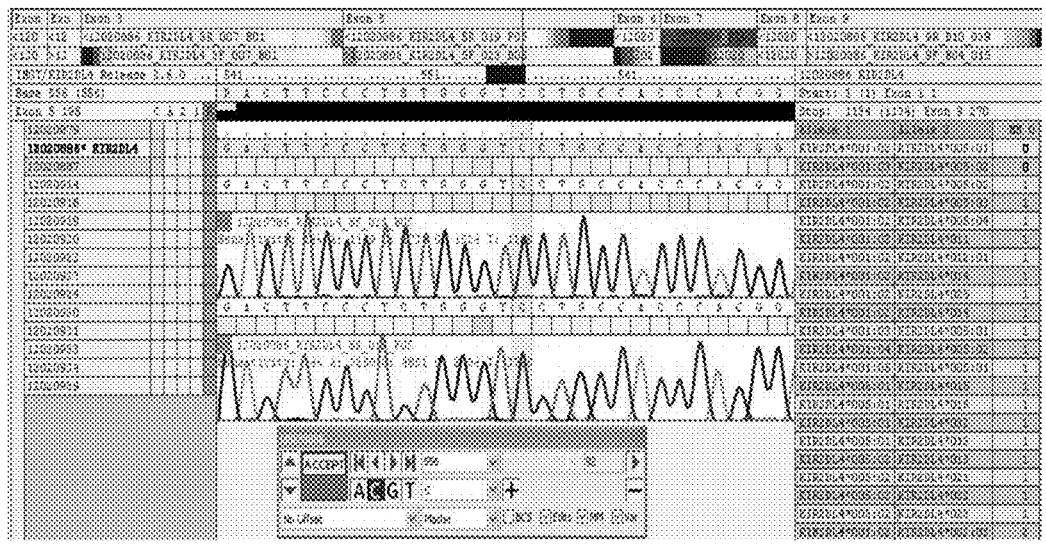
Figure 5E:
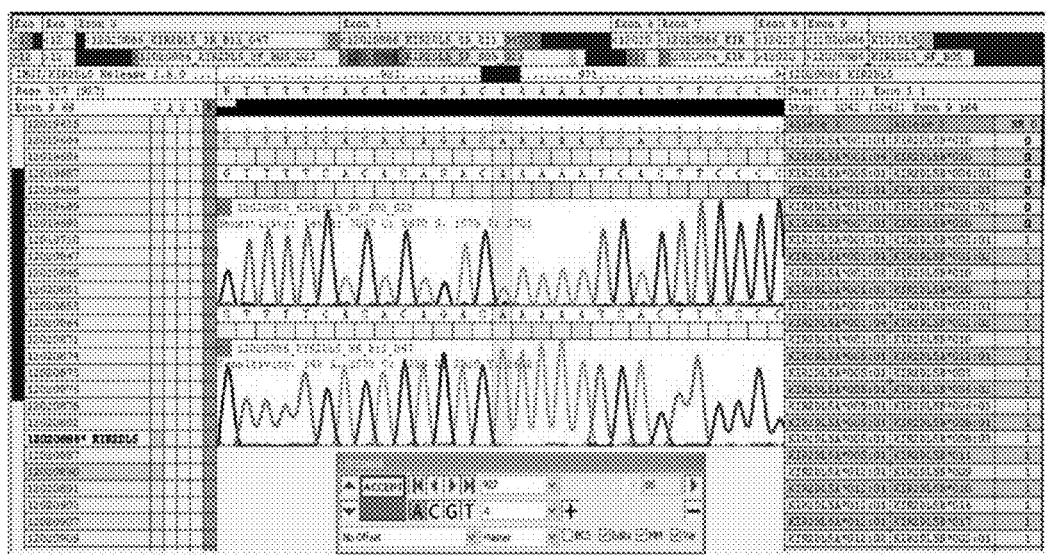
Figure 5F:
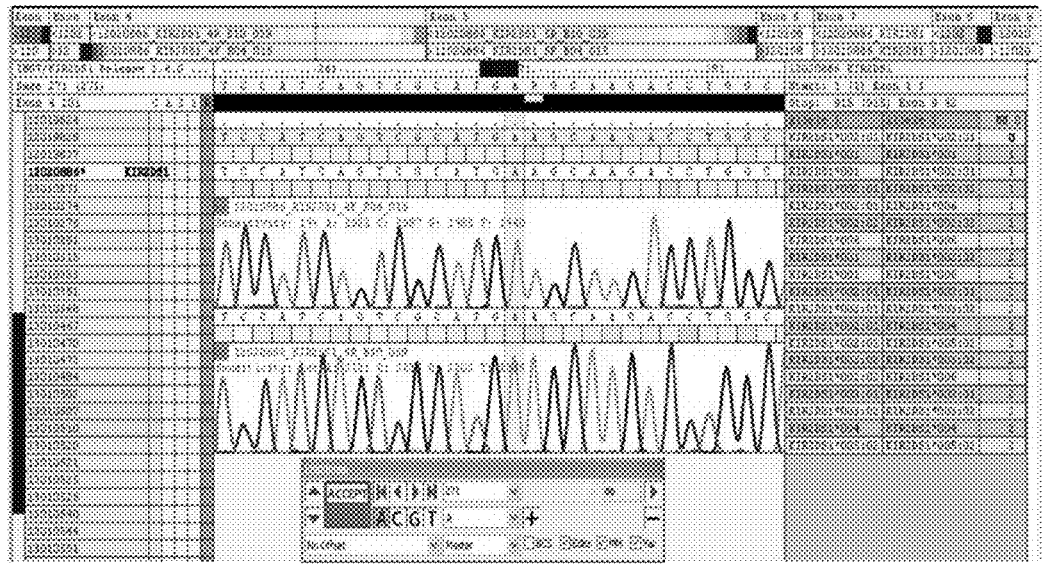
Figure 5G:
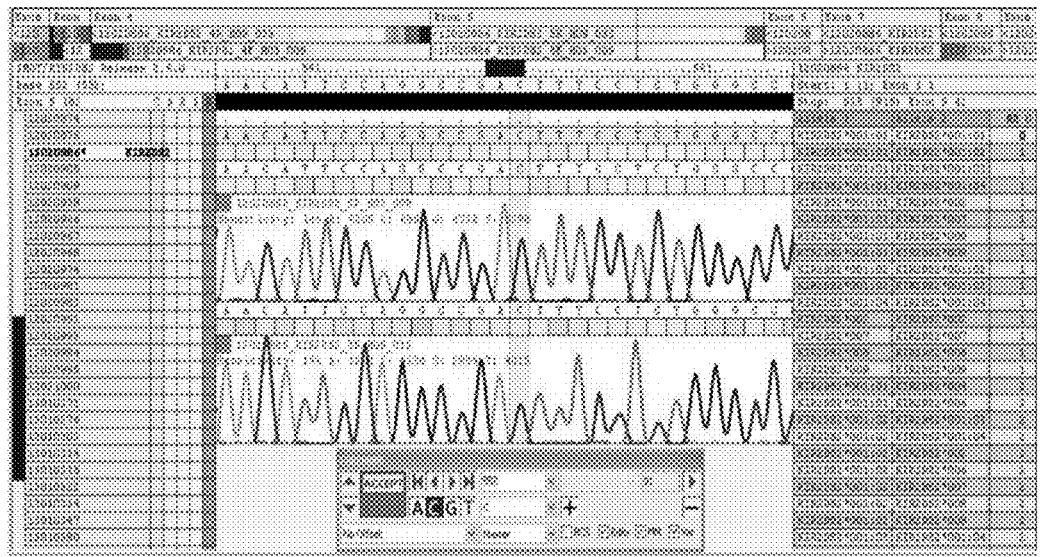
Figure 5H:
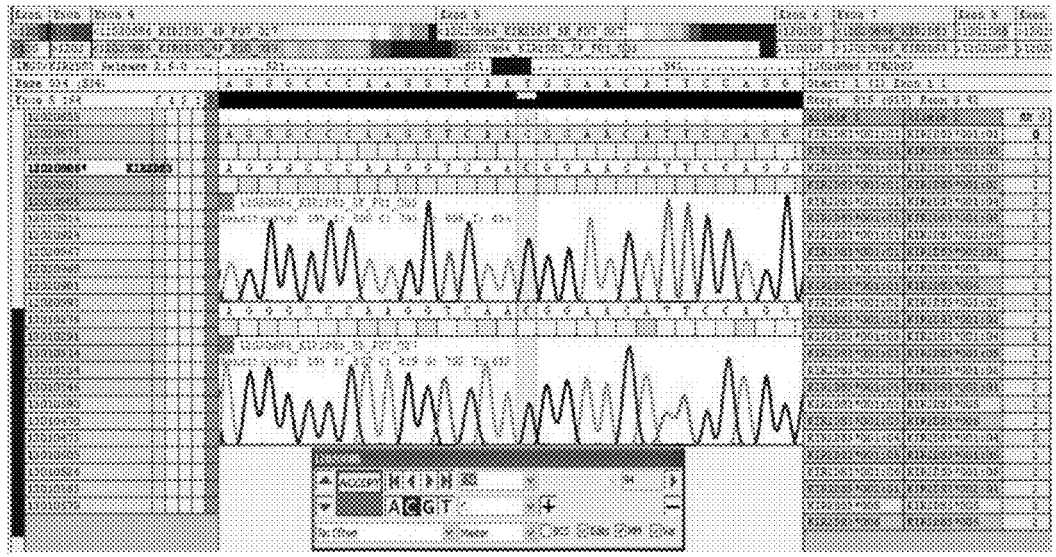
Figure 5I:
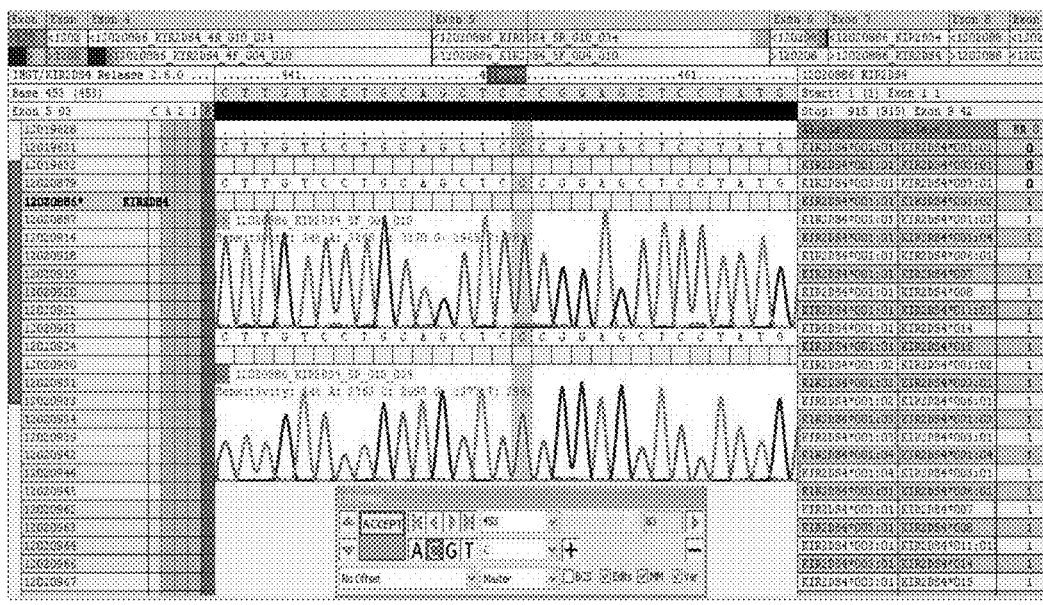
Figure 5J:
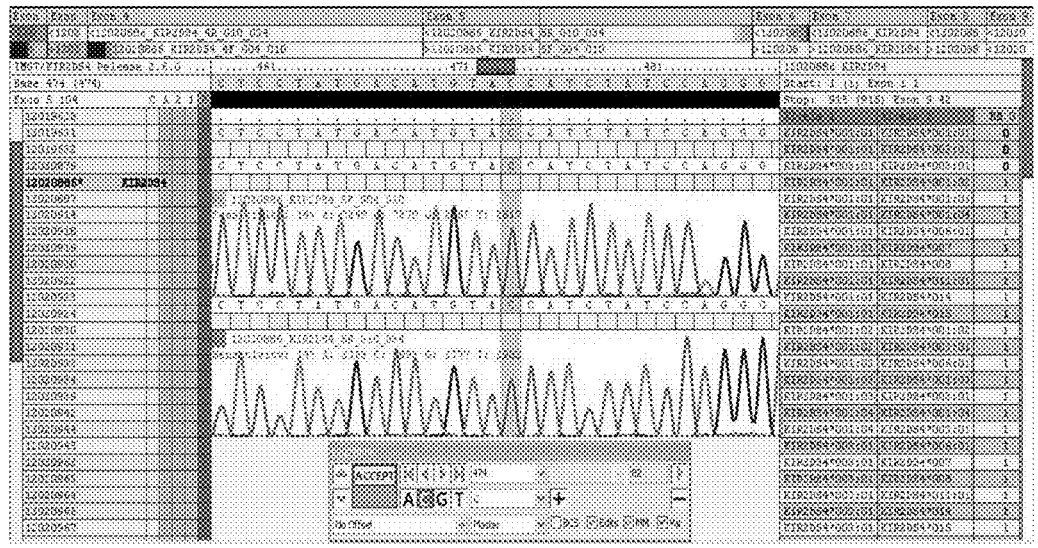
Figure 5K:
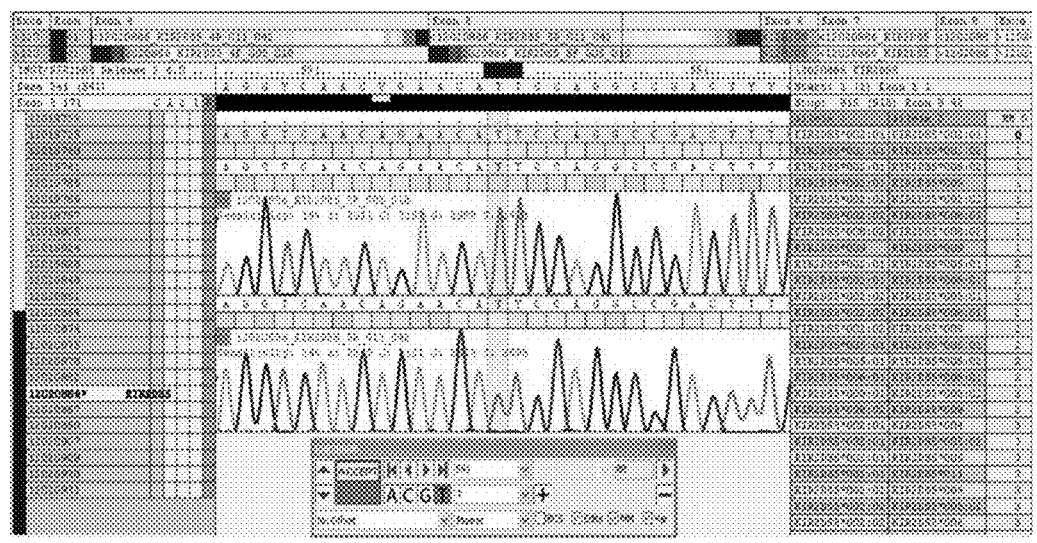
Figure 5L:
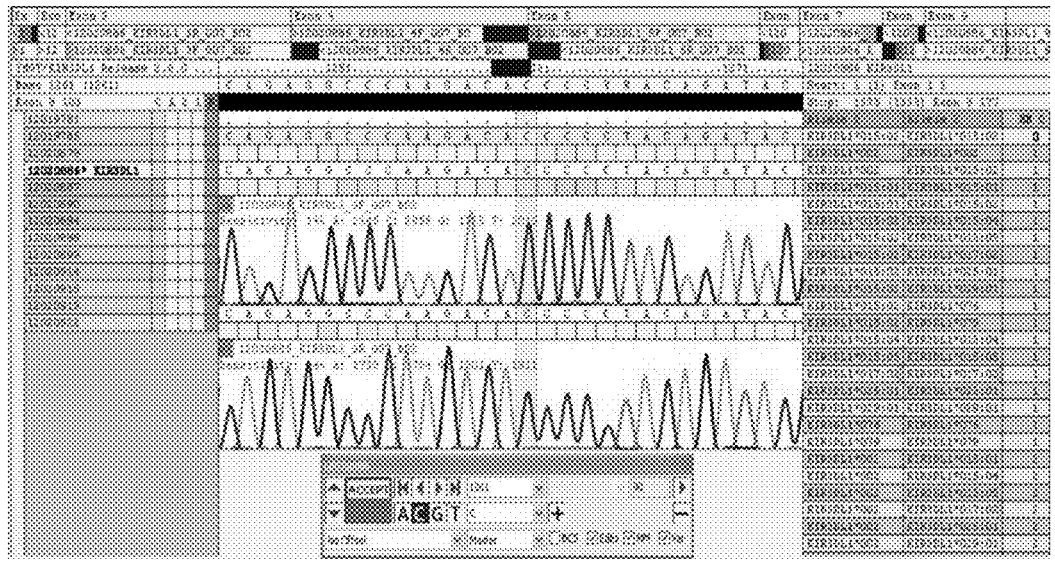
Figure 5M:
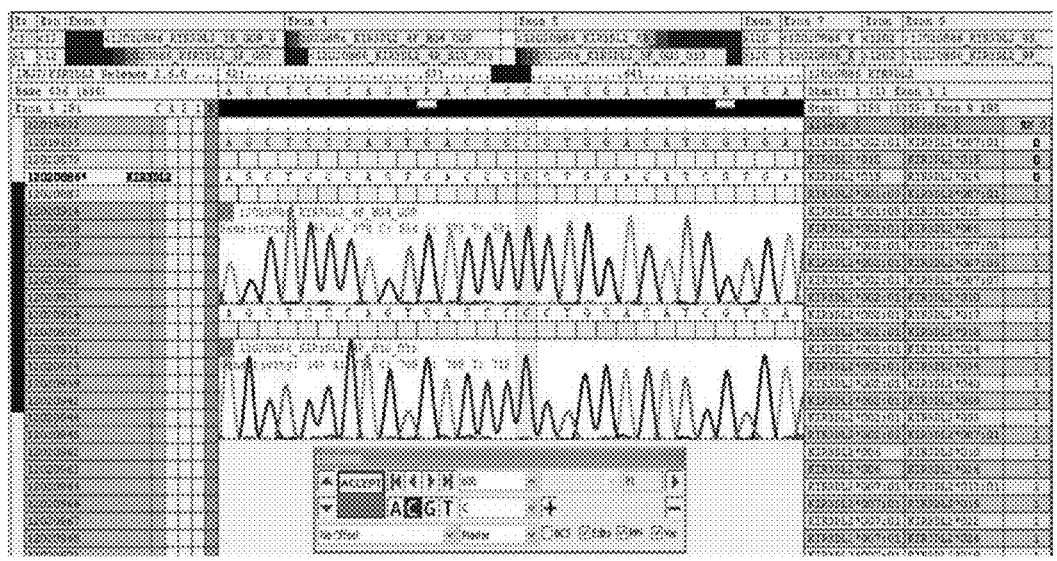
Figure 5N:
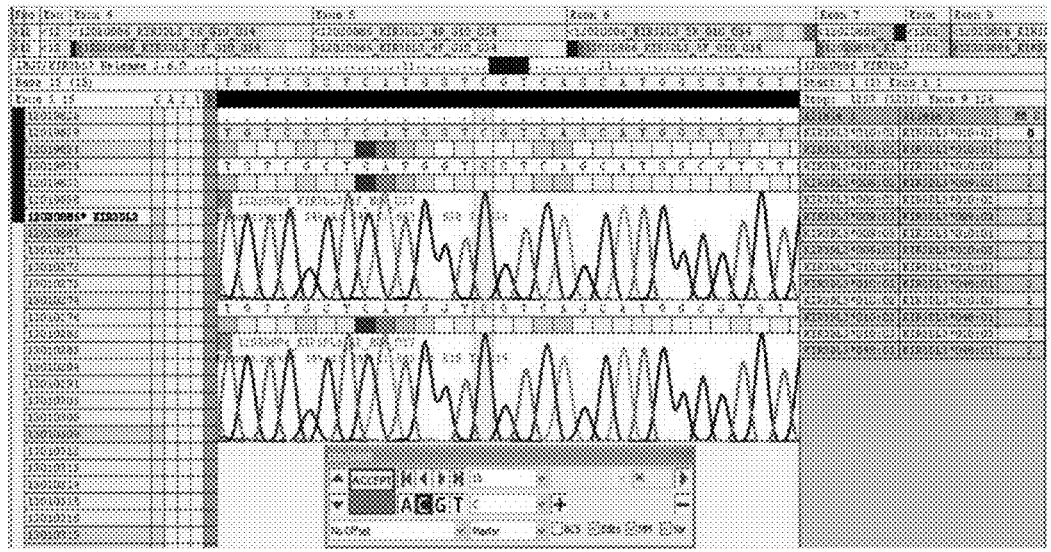
Figure 5O:
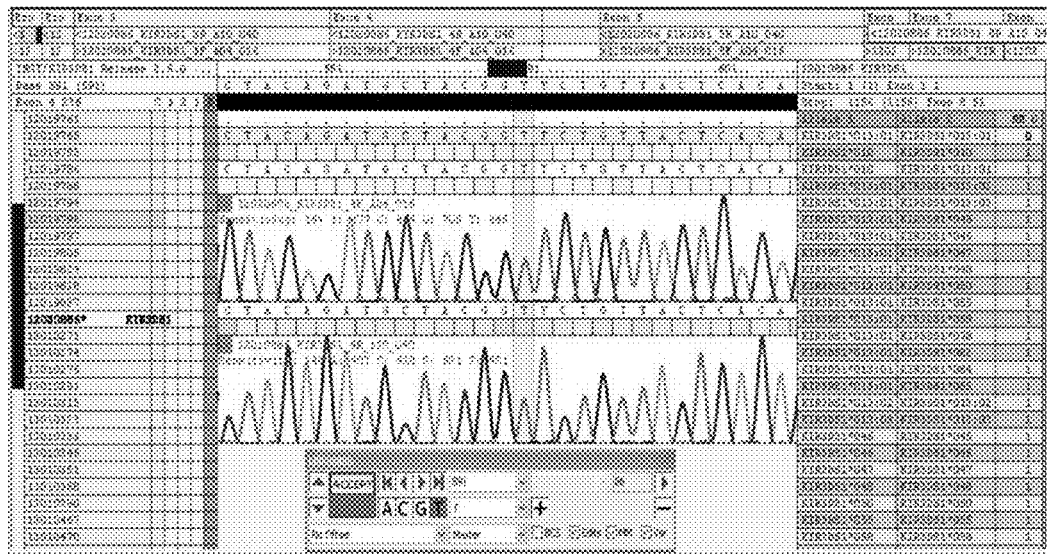

FIGS. 5A to 5O indicate the effect of KIR SBT and allele assignment for a DNA sample with KIRAB6 profile that carrys all 14 functional KIR genes. The obtained sequences covering all the exons of each above KIR gene are imported into Assign 3.5 or 4.7 software, the allele level genotype of the sample in the second embodiment is KIR2DL1*00302, 00401-2DL2*00301-2DL3*00101-2DL4*00102,00501-2DL5A*00101,B*010-2DS1*00201-2DS2*00101-2DS3*00101-2DS4*00101-2DS5*00201-3DL1*01502-3DL 2*00201,00701-3DL3*01002-3DS1*01301.

The foregoing objects, features and advantages of the present disclosure will be described in greater detail with reference to the accompanying drawings.

DETAILED DESCRIPTION OF THE EMBODIMENTS

Embodiment 1

In the present embodiment, a randomly selected DNA sample which had been previously identified as KIRAA1 profile using a commercial KIR-SSP kit was subjected to sequence-based typing according to the present disclosure with an aim to confirm the effect of this disclosure. Firstly, the complete coding region of each functional KIR gene was separately amplified using 3~5 pairs of KIR gene-specific PCR primers in an ABI 9700 PCR cycler. All the PCR amplifications were carried out in a volume of 10 μL containing:

| | |
|---|---|
| 10× PCR Buffer (without MgCl$_2$) | 1.0 μL |
| 2.5 mM dNTP | 0.8 μL, |
| 5.0 mM MgCl$_2$ | 3.0 μL, |
| 10 μM each PCR Primer | 0.4 μL, |
| 50~100 ng/μL Genomic DNA | 2.0 μL, |
| 5 U/μL Taq DNA Polymerase | 0.1 μL, |
| Add ddH$_2$O to | 10.0 μL. |

All the PCR amplifications were simultaneously amplified under the same thermocycling parameters described below:

| | |
|---|---|
| 95° C. | 3 min; |
| 95° C. | 15 Sec, |
| 68° C. | 15 Sec, |
| 72° C. | 3.5 min, 35 cycles; |
| 72° C. | 7 min; |
| 4° C. | Infinite. |

To confirm successful PCR amplification, 2 μL PCR products mixed with 1 μL nucleic acid dye as well as 3 μL 5×loading buffer were electrophoresed on a 2% agarose gel. The expected sizes of PCR products were in comparison with Takara DL2000 DNA markers. As a result, specific and clear PCR product bands for 7 KIR genes (KIR2DL1, 2DL3, 2DL4, 2DS4, 3DL1, 3DL2 and 3DL3) were observed on the gel, indicating the tested sample carried the above KIR genes. However, the remaining 7 functional KIR genes including KIR2DL2, 2DL5, 2DS1, 2DS2, 2DS3, 2DS5 and 3DS1 were absent since no specific PCR product band was observed on the gel. Thus, the PCR products amplified by using the PCR primers of this disclosure were subjected to agarose gel electrophoresis, the result was completely consistent with the known KIRAA1 profile. The electrophoresis images of the tested sample are shown in FIG. 2.

Now that the 7 functional KIR genes (KIR2DL1, 2DL3, 2DL4, 2DS4, 3DL1, 3DL2 and 3DL3) were present for the tested sample, the specific PCR products of these KIR genes were then purified using the same purification system described below:

| | |
|---|---|
| 1 U/μL Thermosensitive Alkaline Phosphatase | 1 μL, |
| 20 U/μL Exonuclease I | 0.25 μL, |
| 10× Reaction Buffer | 3 μL, |
| PCR Products | 10 μL. |

Purification of PCR products were carried out under the same thermocycling parameters described below:

| | |
|---|---|
| 37° C. | 45 min; |
| 85° C. | 15 min; |
| 4° C. | Infinite. |

Upon completion, dilute the purified product 1:3 with sterile deionized water. Mix gently by vortexing and centrifuge briefly.

The nucleotide sequences of each exon carried by purified PCR amplicons were determined in both directions. As for KIR2DL1, 2DL3, 2DL4, 2DS4 and 3DL3 genes, each KIR gene was sequenced using sixteen specific sequencing primers, respectively. For KIR3DL1 and 3DL2 genes, each KIR gene was sequenced using eighteen specific sequencing primers, respectively. All the sequencing reactions were carried out in a volume of 10 μL containing:

| | |
|---|---|
| 5× BigDye Sequencing Buffer | 2.075 μL, |
| BigDye Terminator 3.1 | 0.25 μL, |
| 10 μM Sequencing Primer | 0.32 μL, |
| Purified PCR Products | 2.0 μL, |
| Add ddH$_2$O to | 10.0 μL. |

The thermocycling parameters for all the sequencing reactions were carried out as follows:

| | |
|---|---|
| 95° C. | 1 min; |
| 95° C. | 10 Sec, |
| 50° C. | 5 Sec, |
| 60° C. | 4 min, 25 cycles; |
| 4° C. | Infinite. |

When the sequencing reaction was completed, purification of sequencing reaction products was carried out by ethanol/NaOAc/EDTA precipitation method, and finally added 15 μL of Hi-Di formamide solution to each well and then denatured at 95° C. for 2.5 min in a PCR cycler. The purified sequencing reaction products were detected by capillary electrophoresis in an ABI 3730 DNA sequencer. All the obtained sequences were then imported into Assign 3.5 or 4.7 software (Conexio Genomics, Western Australia) (see FIGS. 3A to 3H), the allele level KIR genotype was identified as "KIR2DL1*00302-KIR2DL3*00101-KIR2DL4*00102,011-KIR2DS4*00101,010-KIR3DL1*00501,01502-KIR3DL2*00201,010-KIR3DL3*00901,010".

Figure 3A:
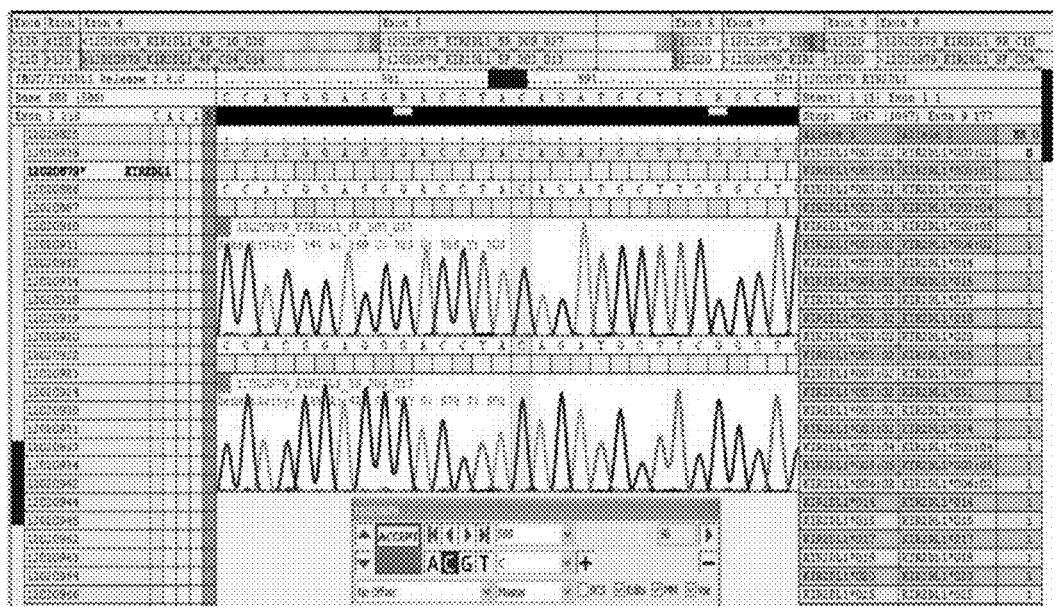
Figure 3B:
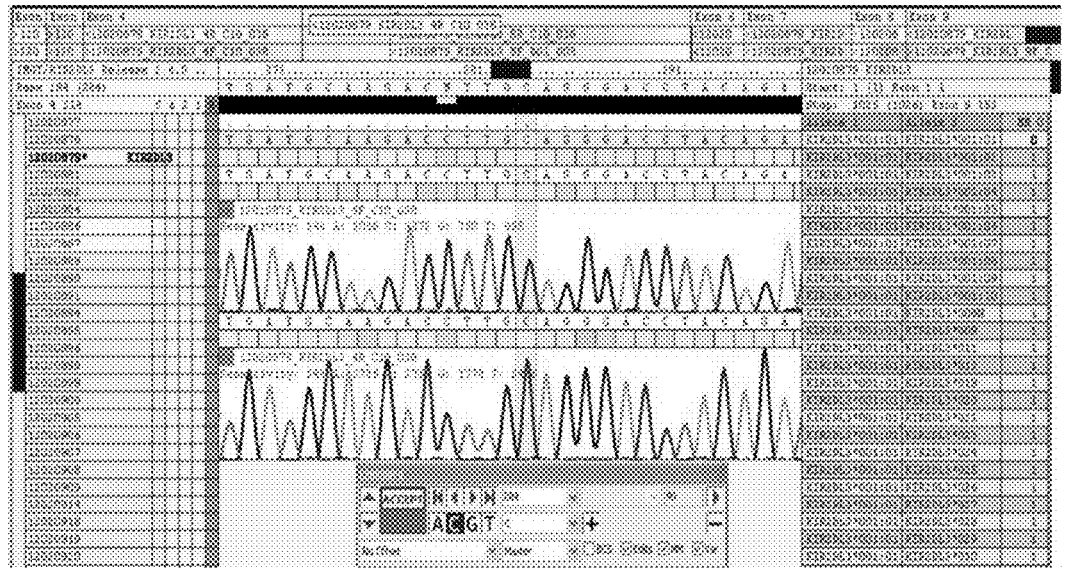
Figure 3C:
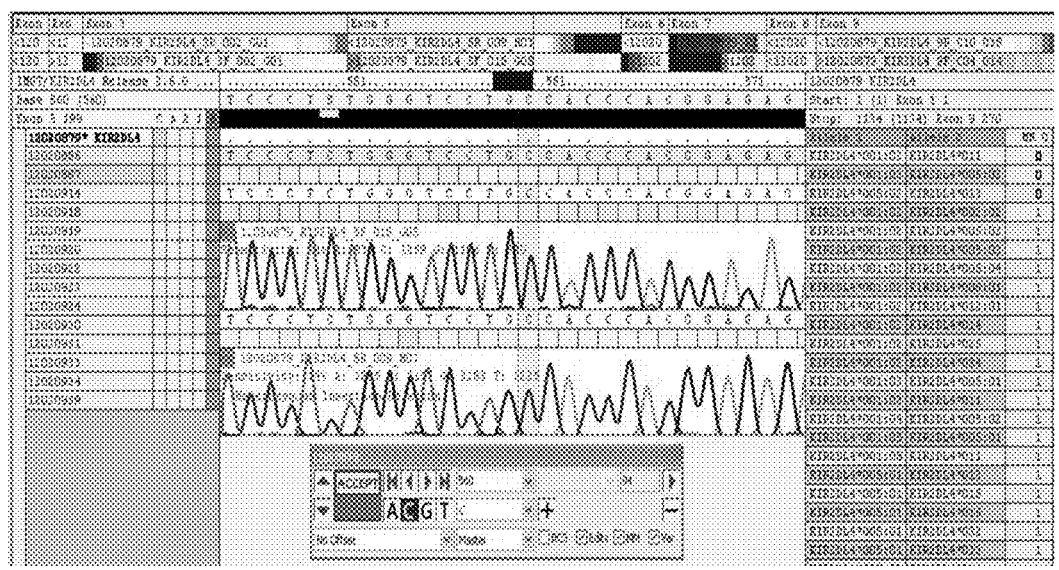
Figure 3D:
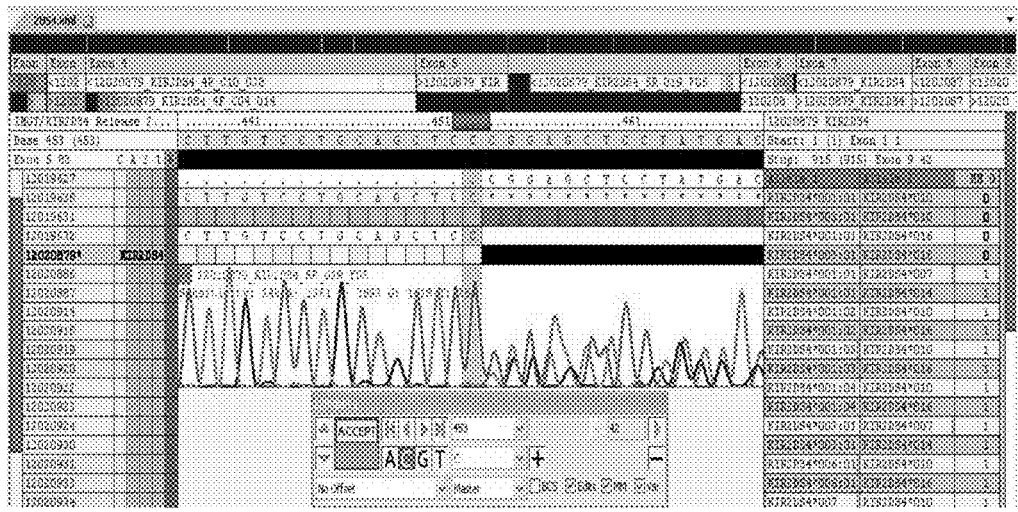
Figure 3E:
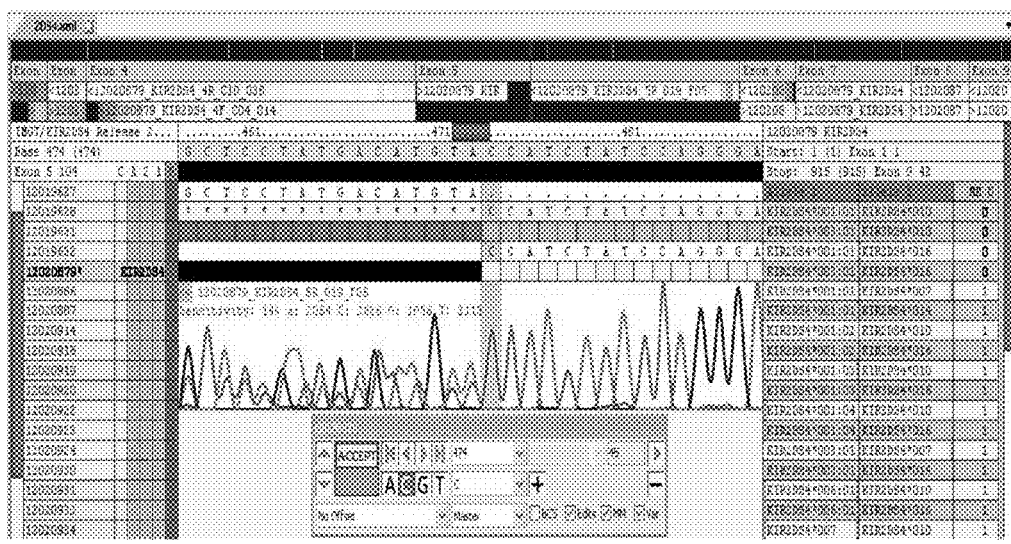
Figure 3F:
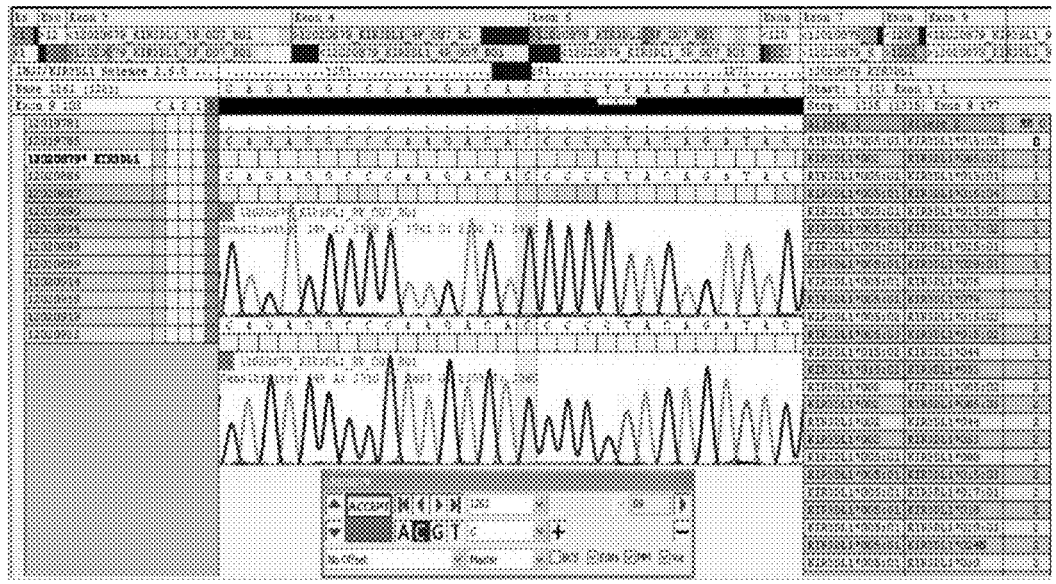
Figure 3G:
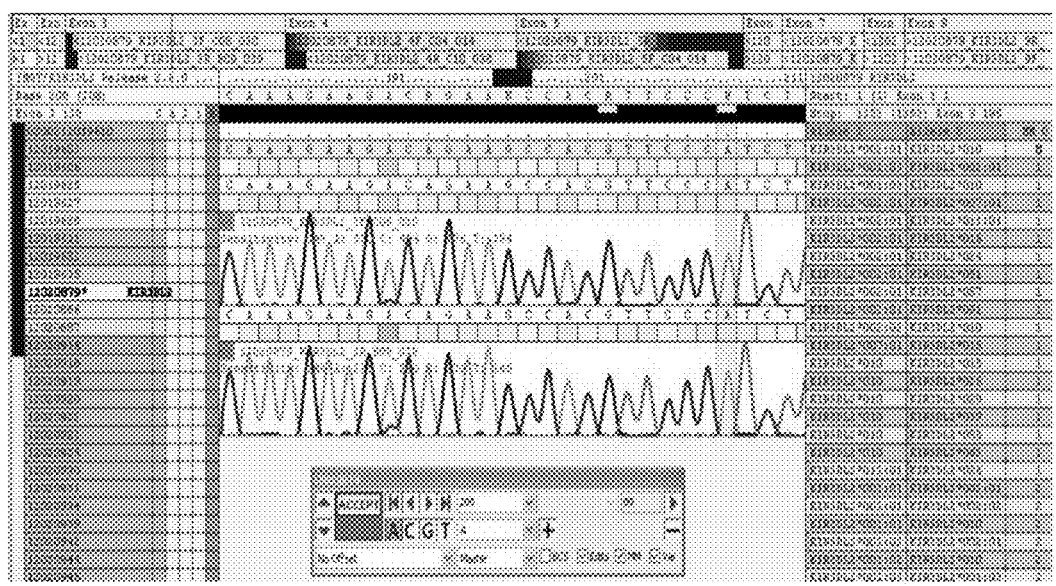
Figure 3H:
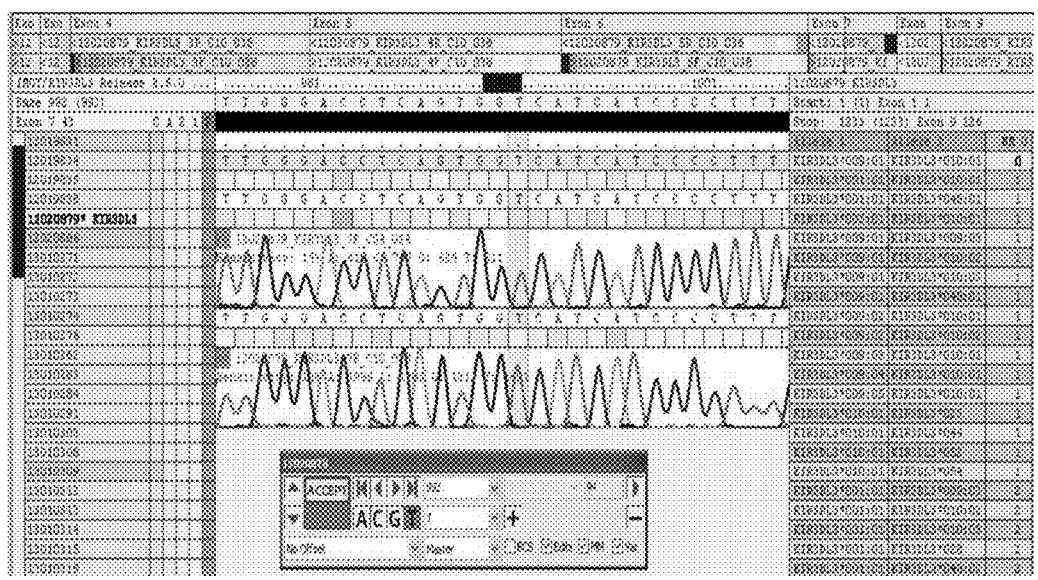

FIG. 3D and FIG. 3E showed 2DS4 SBT results with heterozygous genotype KIR2DS4*00101, 010. Since KIR2DS4*010 has a 22 bp deletion in exon 5, whereas KIR2DS4*00101 does not possess a 22 bp deletion, forward sequencing result of exon 5 showed that nucleotide misalignment occurred at the nucleotide position nt454 and the downstream region (see FIG. 3D), while reverse sequencing result of exon 5 showed that nucleotide misalignment occurred at nucleotide position nt475 and the upstream region (see FIG. 3E).

Embodiment 2

In the present embodiment, a randomly selected DNA sample which had been previously identified as KIRAB6 profile using a commercial KIR-SSP kit was subjected to sequence-based typing according to the present disclosure with an aim to confirm the effect of this disclosure. Firstly, the complete coding region of each functional KIR gene was separately amplified using 3~5 pairs of KIR gene-specific PCR primers in an ABI 9700 PCR cycler. All the PCR amplifications were carried out in a volume of 10 μL containing:

| | |
|---|---|
| 10× PCR Buffer (without MgCl$_2$) | 1.0 μL |
| 2.5 mM dNTP | 0.8 μL, |
| 5.0 mM MgCl$_2$ | 3.0 μL, |
| 10 μM each PCR Primer | 0.4 μL, |
| 50~100 ng/μL Genomic DNA | 2.0 μL, |
| 5 U/μL Taq DNA Polymerase | 0.1 μL, |
| Add ddH$_2$O to | 10.0 μL. |

All the PCR amplifications were simultaneously amplified under the same thermocycling parameters described below:

| | |
|---|---|
| 95° C. | 3 min; |
| 95° C. | 15 Sec, |
| 68° C. | 15 Sec, |
| 72° C. | 3.5 min, 35 cycles; |
| 72° C. | 7 min; |
| 4° C. | Infinite. |

To confirm successful PCR amplification, 2 μL PCR products mixed with 1 μL nucleic acid dye as well as 3 μL loading buffer were electrophoresed on a 2% agarose gel. The expected sizes of PCR products were in comparison with Takara DL2000 DNA markers. As a result, specific and clear PCR product bands for 14 KIR genes (KIR2DL1, 2DL2, 2DL3, 2DL4, 2DL5, 2DS1, 2DS2, 2DS3, 2DS4, 2DS5, 3DL1, 3DL2, 3DL3 and 3DS1) were observed on gel, indicating the tested sample carried the above KIR genes. Thus, the PCR products amplified by using the PCR primers of this disclosure subjected to agarose gel electrophoresis, the result is completely consistent with the known KIRAB6 profile. The electrophoresis images of the tested sample are shown in FIG. 4.

Now that the 14 functional KIR genes (KIR2DL1, 2DL2, 2DL3, 2DL4, 2DL5, 2DS1, 2DS2, 2DS3, 2DS4, 2DS5, 3DL1, 3DL2, 3DL3 and 3DS1) were present for this tested sample, the specific PCR products of these KIR genes were then purified using the same purification system described below:

| | |
|---|---|
| 1 U/μL Thermosensitive Alkaline Phosphatase | 1 μL, |
| 20 U/μL Exonuclease I | 0.25 μL, |
| 10× Reaction Buffer | 3 μL, |
| PCR Products | 10 μL. |

Purification of PCR products were carried out under the same thermocycling parameters described below:

| | |
|---|---|
| 37° C. | 45 min; |
| 85° C. | 15 min; |
| 4° C. | Infinite. |

Upon completion, diluted the purified PCR product 1:3 with sterile deionized water. Mixed gently by vortexing and centrifuge briefly.

The nucleotide sequences of each exon carried by the purified PCR amplicons were determined in both directions. As for KIR2DL1~5, 2DS1~5 and KIR3DL3 genes, each KIR gene was sequenced using sixteen specific sequencing primers, respectively. For KIR3DL1~2 and KIR3DS1 genes, each KIR gene was sequenced using eighteen specific sequencing primers, respectively. All the sequencing reactions were carried out in a volume of 10 μL containing:

| | |
|---|---|
| 5× BigDye Sequencing Buffer | 2.075 μL, |
| BigDye Terminator 3.1 | 0.25 μL, |
| 10 μM Sequencing Primer | 0.32 μL, |
| Purified PCR Products | 2.0 μL, |
| Add ddH₂O to | 10.0 μL. |

The thermocycling parameters for all the sequencing reactions were carried out as follows:

| | |
|---|---|
| 95° C. | 1 min; |
| 95° C. | 10 Sec, |
| 50° C. | 5 Sec, |
| 60° C. | 4 min, 25 cycles; |
| 4° C. | Infinite. |

When the sequencing reactions were completed, purification of sequencing reaction products was carried out by ethanol/NaOAc/EDTA precipitation method, and finally added 15 μL, of Hi-Di formamide solution to each well and then denatured at 95V for 2.5 min in a PCR cycler. The purified sequencing reaction products were detected by capillary electrophoresis in an ABI 3730 DNA sequencer. All the obtained sequences were then imported into Assign 3.5 or 4.7 software (Conexio Genomics, Western Australia) (FIGS. 5A~5O), the allele level KIR genotype was identified as "KIR2DL1*00302,00401-KIR2DL2*00301-KIR2DL3*00101-KIR2DL4*00102,00501-KIR2DL5A*00101,B*010-KIR2DS1*00201-KIR2DS2*00101-KIR2DS3*00101-KIR2DS4*00101-KIR2DS5*00201-KIR3DL1*01502-KIR3DL2*00201,00701-KIR3DL3*01002-KIR3DS1*01301".

FIG. 5I and FIG. 5J showed 2DS4 SBT results with homozygous KIR2DS4*00101, 00101. Since KIR2DS4*00101 does not possess a 22 bp deletion in exon 5, forward sequencing result of exon 5 showed that no nucleotide misalignment occurred at the nucleotide position nt454 and the downstream region (see FIG. 5I), reverse sequencing result of exon 5 showed that no nucleotide misalignment occurred at nucleotide position nt475 and the upstream region (see FIG. 5J).

Embodiment 3

In the present embodiment, a total number of 306 randomly selected DNA samples which had been previously detected using a commercial KIR-SSP kit were subjected to sequence-based typing according to the present disclosure with an aim to confirm the effect of this disclosure. Firstly, the complete coding region of each functional KIR gene was separately amplified using 3~5 pairs of KIR gene-specific PCR primers in an ABI 9700 PCR cycler. All the PCR amplifications were carried out in a volume of 10 μL containing:

| | |
|---|---|
| 10× PCR Buffer (without MgCl₂) | 1.0 μL |
| 2.5 mM dNTP | 0.8 μL, |
| 5.0 mM MgCl₂ | 3.0 μL, |
| 10 μM each PCR Primer | 0.4 μL, |
| 50~100 ng/μL Genomic DNA | 2.0 μL, |
| 5 U/μL Taq DNA Polymerase | 0.1 μL, |
| Add ddH₂O to | 10.0 μL. |

All the PCR amplifications were simultaneously amplified under the same thermocycling parameters described below:

| | |
|---|---|
| 95° C. | 3 min; |
| 95° C. | 15 Sec, |
| 68° C. | 15 Sec, |
| 72° C. | 3.5 min, 35 cycles; |
| 72° C. | 7 min; |
| 4° C. | Infinite. |

To confirm successful PCR amplification, 2 μL PCR products mixed with 1 μL nucleic acid dye as well as 3 μL loading buffer were electrophoresed on a 2% agarose gel. The expected sizes of PCR products were in comparison with Takara DL2000 DNA markers. As a result, the PCR products amplified by using the PCR primers of this disclosure were subjected to agarose gel electrophoresis, the results were completely consistent with the known KIR profiles for all the 306 DNA samples.

PCR products for KIR genes that were present in each tested DNA sample, were then purified using the same purification system described below:

| | |
|---|---|
| 1 U/μL Thermosensitive Alkaline Phosphatase | 1 μL, |
| 20 U/μL Exonuclease I | 0.25 μL, |
| 10× Reaction Buffer | 3 μL, |
| PCR Products | 10 μL. |

Purification of PCR products were carried out under the same thermocycling parameters described below:

| | |
|---|---|
| 37° C. | 45 min; |
| 85° C. | 15 min; |
| 4° C. | Infinite. |

Upon completion, dilute the purified PCR products 1:3 with sterile deionized water. Mix gently by vortexing and centrifuge briefly.

The nucleotide sequences of each exon carried by purified PCR amplicons were determined in both directions. As for KIR2DL1~5, 2DS1~5, and KIR3DL3 genes, each KIR gene was sequenced using sixteen specific sequencing primers, respectively. For KIR3DL1~2 and KIR3DS1 genes, each KIR gene was sequenced using eighteen specific sequencing primers, respectively. All the sequencing reactions were carried out in a volume of 10 μL containing:

| | |
|---|---|
| 5× BigDye Sequencing Buffer | 2.075 μL, |
| BigDye Terminator 3.1 | 0.25 μL, |
| 10 μM Sequencing Primer | 0.32 μL, |
| Purified PCR Product | 2.0 μL, |
| Add ddH₂O to | 10.0 μL. |

The thermocycling parameters for all the sequencing reactions were carried out as follows:

| | |
|---|---|
| 95° C. | 1 min; |
| 95° C. | 10 Sec, |
| 50° C. | 5 Sec, |
| 60° C. | 4 min, 25 cycles; |
| 4° C. | Infinite. |

When the sequencing reactions were completed, purification of sequencing reaction products was carried out by ethanol/NaOAc/EDTA precipitation method, and finally added 15 μL of Hi-Di formamide solution to each well and then denatured at 95° C. for 2.5 min in a PCR cycler. The purified sequencing reaction products were detected by capillary electrophoresis in an ABI 3730 DNA sequencer. All the obtained sequences were then imported into Assign 3.5 or 4.7 software (Conexio Genomics, Western Australia), the allele level KIR genotype for each sample was identified (see Table 6). The identified alleles and their frequencies of 14 functional KIR genes in southern Chinese Han population (n=306) were provided in Table 7.

TABLE 6

SBT Results of 14 Functional KIR Genes in Southern Chinese Han Population (n = 306)

| No. | 2DL1 | 2DL2/3 | 2DL4 | 2DL5A | 2DL5B | 2DS1 | 2DS2 |
|---|---|---|---|---|---|---|---|
| 1 | 00302 | 3*00101, 3*00109 | 00102, 00501 | 005 | | 00201 | |
| 2 | 00302 | 3*00101 | 011 | | | | |
| 3 | 00302 | 3*00101 | 00102, 00801 | | | | |
| 4 | 00302 | 3*00109, 3*023 | 006, 00801 | | | | |
| 5 | 00302 | 3*00101 | 00102, 011 | | | | |
| 6 | 00302 | 3*00101 | 00102 | | | | |
| 7 | 00302 | 3*00101 | 00102, 00501 | 005 | | 00201 | |
| 8 | 00302 | 3*00101 | 00102, 00501 | 001 | | 00201 | |
| 9 | 00302 | 3*00101, 3*028 | 00102, 00801 | | | | |
| 10 | 00201, 00302 | 3*00101, 3*00201 | 00501, 006 | 001 | | 00201 | |
| 11 | 00201, 00302 | 3*00101, 3*00201 | 00102, 011 | | | | |
| 12 | 00201 | 2*00301, 3*00201 | 00102, 00501 | 001 | 006 | 00201 | 00101 |
| 13 | 00302 | 3*00101, 3*029 | 00102 | | | | |
| 14 | 00302 | 3*00101 | 00102, 006 | | | | |
| 15 | 00302 | 3*00101 | 00102 | | | | |
| 16 | 00302 | 2*00301, 3*00101 | 00102 | | | | 00101 |
| 17 | 00302 | 3*00101 | 00102, 011 | | | | |
| 18 | 00201, 00302 | 3*00101, 3*00201 | 00501, 011 | 001 | | 00201 | |
| 19 | 00302 | 2*00301, 3*00101 | 00102, 006 | | | | 00101 |
| 20 | 00302 | 2*00301, 3*00101 | 00501 | 001 | 010 | 00201 | 00101 |
| 21 | 00302 | 2*00301, 3*00101 | 00102 | | 006 | 00201 | 00101 |
| 22 | 00302 | 3*00101 | 00102, 011 | | | | |
| 23 | 00302 | 3*00101 | 00102, 00801 | | | | |
| 24 | 00302 | 3*00101 | 00102 | | | | |
| 25 | 00302, 00401 | 2*00301, 3*00101 | 00102, 006 | | 010 | | 00101 |
| 26 | 00302, 00401 | 2*00101, 3*00101 | 00102, 00501 | 001 | 002 | 00201 | 00101 |
| 27 | 00302 | 2*00301, 3*00101 | 00102, 006 | | | | 00101 |
| 28 | 00201 | 3*00201 | 00102, 011 | | | | |
| 29 | 00201, 00302 | 3*00101, 3*00201 | 00102, 006 | | | | |
| 30 | 00302 | 2*00301, 3*00101 | 00103, 00501 | 001 | 006 | 00201 | 00101 |
| 31 | 00302, 00401 | 2*00301, 3*00101 | 00501 | 001, 005 | 006 | 00201 | 00101 |
| 32 | 00302 | 2*00301, 3*00101 | 00102 | | 006 | 00201 | 00101 |
| 33 | 00201 | 3*00201 | 00501, 011 | 012 | | 00201 | |
| 34 | 00201, 00302 | 3*00101, 3*00201 | 00102, 011 | | | | |
| 35 | 00302 | 2*00301, 3*00101 | 00102, 00501 | 001 | 006 | 00201 | 00101 |
| 36 | 00302, 00401 | 2*00101, 3*00101 | 00102 | | 002 | | 00101 |
| 37 | 00302 | 3*00101 | 00102, 00504 | 001 | | 00201 | |
| 38 | 00302 | 3*00101 | 00102 | | | | |
| 39 | 00302 | 3*00101 | 00102 | | | | |
| 40 | 00302 | 3*00101 | 00102 | | | | |
| 41 | 00302 | 3*00101 | 00102 | | | | |
| 42 | 00302 | 2*00301, 3*00101 | 00503 | 001, 012 | | 00201 | 00101 |
| 43 | 00302, 00401 | 2*00301, 3*00101 | 00102 | | 010 | | 00101 |
| 44 | 00302 | 2*00301, 3*00101 | 00102 | | | | 00101 |
| 45 | 00302 | 3*00101 | 00501, 006 | 005 | | 00201 | |
| 46 | 00302, 031 | 3*00101, 3*023 | 00102, 00501 | 001 | | 00201 | |
| 47 | 00302 | 3*00101 | 00801, 011 | | | | |
| 48 | 00302, 00401 | 2*00101, 3*00101 | 00102, 00501 | 005 | 002 | | 00101 |
| 49 | 00302 | 3*00101 | 00103, 011 | | | | |
| 50 | 00302, 00401 | 2*00101, 3*00101 | 00102 | | 002 | | 009 |
| 51 | 00201, 00302 | 3*00101, 3*00201 | 00501, 006 | 001 | | 00201 | |
| 52 | 00302 | 3*00101 | 00102, 011 | | | | |
| 53 | 00302 | 3*00101 | 00102, 011 | | | | |
| 54 | 001, 00201 | 2*00101, 3*00201 | 00501 | 001 | 002 | 00201 | 009 |
| 55 | 00201, 00302 | 3*00101, 3*00201 | 00102, 011 | | | | |
| 56 | 00302 | 3*00101 | 00102, 00501 | 022 | | 00201 | |
| 57 | 00201, 00302 | 3*00101, 3*00201 | 00102 | | | | |
| 58 | 00302 | 3*00101, 3*027 | 011 | | | | |
| 59 | 00302 | 3*00101, 3*023 | 00102 | | | | |
| 60 | 00302 | 3*00101 | 00102 | | | | |
| 61 | 00302 | 3*00101 | 00102, 011 | | | | |
| 62 | 00302 | 3*00101 | 00102, 00501 | 001 | | 00201 | |
| 63 | 00302 | 3*00101 | 00102, 011 | | | | |

TABLE 6-continued

SBT Results of 14 Functional KIR Genes in Southern Chinese Han Population (n = 306)

| # | | | | | | | |
|---|---|---|---|---|---|---|---|
| 64 | 00302 | 3*00101 | 00102, 006 | | | | |
| 65 | 00201, 00302 | 3*00101, 3*00201 | 00102, 006 | | | | |
| 66 | 00401 | 2*00101, 2*00301 | 00102, 00801 | | 002, 010 | | 00101, 009 |
| 67 | 00302 | 2*00301, 3*00101 | 006, 00801 | | | | 00101 |
| 68 | 00302 | 3*00101 | 00102 | | | | |
| 69 | 00201 | 2*00301, 3*00201 | 011 | | 008 | | 00101 |
| 70 | 00201, 00302 | 3*00101, 3*00201 | 00501, 011 | 001 | | 00201 | |
| 71 | 00302, 00401 | 2*00301, 3*023 | 00102, 00103 | | 010 | | 00101 |
| 72 | 030 | 3*00101 | 011 | | | | |
| 73 | 00302 | 3*00101 | 00102, 00501 | 001 | | 00201 | |
| 74 | 00302 | 3*00101 | 00102, 011 | | | | |
| 75 | 00201, 00302 | 3*00101, 3*00201 | 00102 | | | | |
| 76 | 00302 | 3*00101 | 00102, 00501 | 001 | | 00201 | |
| 77 | 00302 | 3*00101 | 00102 | | | | |
| 78 | 00302, 00401 | 2*00301, 3*00101 | 00102, 00501 | 001 | 010 | 00201 | 00101 |
| 79 | 00201, 00302 | 3*00101, 3*00201 | 00501, 011 | 001 | | 00201 | |
| 80 | 00201, 00302 | 3*00201, 3*023 | 00102 | | | | |
| 81 | 00302 | 3*00101 | 00102, 00501 | 001 | | 00201 | |
| 82 | 00302 | 3*00101 | 00501, 00801 | 005 | | 00201 | |
| 83 | 00201, 00302 | 3*00101, 3*00201 | 006, 00801 | | | | |
| 84 | 00302 | 3*00101 | 00102 | | | | |
| 85 | 00302 | 3*00101 | 00102, 011 | | | | |
| 86 | 00201, 00302 | 3*00101, 3*00201 | 00102 | | | | |
| 87 | 00302 | 3*00101 | 00102 | | | | |
| 88 | 00302 | 3*00101 | 00102 | | | | |
| 89 | 00302 | 3*00101 | 00102, 00103 | | | | |
| 90 | 00302 | 2*00301, 3*00101 | 00103, 00501 | 005 | 010 | 00201 | 00101 |
| 91 | 00302 | 2*00301, 3*00101 | 00501, 011 | 001 | 006 | 00201 | 00101 |
| 92 | 00302 | 3*00101 | 00102, 011 | | | | |
| 93 | 00302 | 3*00101, 3*023 | 00102, 00501 | 001 | | 00201 | |
| 94 | 00302 | 3*00101 | 00102, 011 | | | | |
| 95 | 00401 | 2*00301, 3*00101 | 00102, 00501 | 001 | 006 | 00201 | 00101 |
| 96 | 00302 | 3*00101, 3*023 | 00102 | | | | |
| 97 | 00302 | 3*00101 | 00102, 006 | | | | |
| 98 | 00201, 00302 | 3*00101, 3*00201 | 00501, 00801 | | | | |
| 99 | 00201, 00302 | 3*00101, 3*00201 | 00102, 011 | | | | |
| 100 | 00302 | 2*00301, 3*00101 | 00102, 00501 | 012 | 006 | 00201 | 00101 |
| 101 | 00201, 00302 | 3*00101, 3*00201 | 00102 | | | | |
| 102 | 00302 | 3*00101 | 00501 | 001, 005 | | 00201 | |
| 103 | 00401 | 2*00301 | 00102 | | 006, 010 | | 00101 |
| 104 | 00201, 00302 | 3*00101, 3*00201 | 00103, 00501 | 001 | | 00201 | |
| 105 | 00302 | 3*00101 | 00501, 00801 | 005 | | 00201 | |
| 106 | 00302 | 3*00101, 3*023 | 00102, 00801 | | | | |
| 107 | 00305 | 2*00301, 3*00101 | 00102, 006 | | | | 00101 |
| 108 | 00302 | 2*00101, 3*00101 | 00102 | | 002 | 00201 | 00101 |
| 109 | 00201, 00302 | 3*00101, 3*015 | 00102, 011 | | | | |
| 110 | 00302 | 2*00301, 3*00101 | 00503, 011 | 001 | 006 | 00201 | 00101 |
| 111 | 00302 | 3*00101, 3*019 | 00102, 011 | | | | |
| 112 | 00302, 00401 | 2*00101, 3*00101 | 00501, 011 | 005 | 002 | 00201 | 00101 |
| 113 | 00302 | 3*00101 | 00103, 00801 | | | | |
| 114 | 00302 | 3*00101 | 00102, 011 | | | | |
| 115 | 00302 | 3*00101 | 00102, 006 | | | | |
| 116 | 00302 | 3*00101, 3*025 | 00102, 011 | | | | |
| 117 | 00302 | 3*00101 | 00102, 00801 | | | | |
| 118 | 00201, 00302 | 3*00101, 3*00201 | 00102, 006 | | | | |
| 119 | 00302 | 2*00301, 3*00101 | 00501, 011 | 001 | 006 | 00201 | 00101 |
| 120 | 00302 | 3*00101 | 00501, 011 | | | | |
| 121 | 00201, 00302 | 3*00101, 3*00201 | 00501, 011 | 001 | | 00201 | |
| 122 | 00302 | 3*00101 | 00102, 011 | | | | |
| 123 | 00302 | 3*00101 | 00102, 00501 | | | | |
| 124 | | 2*00301 | 00501 | 001 | 006 | 00202 | 00101 |
| 125 | 00302 | 3*00101 | 00102, 00501 | 005 | | 00201 | |
| 126 | 00201, 00302 | 3*00101, 3*00201 | 00102, 006 | | | | |
| 127 | 00302 | 3*00101 | 00102, 00501 | 001 | | 00201 | |
| 128 | 00302 | 3*00101 | 00102 | | | | |
| 129 | 00302 | 3*00101 | 00102 | | | | |
| 130 | 00302 | 3*00101 | 00102, 00504 | 001 | | 00201 | |
| 131 | 00302 | 3*00101 | 00102, 00103 | | | | |
| 132 | | 2*00301 | 00102, 00501 | 012 | 006 | 00201 | 00101 |
| 133 | 00302 | 2*00301, 3*00101 | 006 | | | | 00101 |
| 134 | 00302 | 3*00101 | 00102, 00501 | 005 | | 00201 | |
| 135 | 00302 | 2*00301, 3*00101 | 00501, 006 | 001 | 006 | 00201 | 00101 |
| 136 | 00302 | 3*00101 | 00102, 00103 | | | | |
| 137 | 00302 | 3*00101 | 00102 | | | | |
| 138 | 00302 | 2*00301, 3*00101 | 00102, 011 | | | | 00101 |
| 139 | 00302 | 3*00101, 3*00109 | 00102, 00501 | 001 | | 00201 | |
| 140 | 00201, 00302 | 3*00101, 3*00201 | 00102, 00501 | 001 | | 00201 | |
| 141 | 00201 | 3*00201 | 00102, 00501 | 001 | | 00201 | |

TABLE 6-continued

SBT Results of 14 Functional KIR Genes in Southern Chinese Han Population (n = 306)

| | | | | | | | |
|---|---|---|---|---|---|---|---|
| 142 | 00302 | 3*00101 | 00102, 00801 | | | | |
| 143 | 00302 | 2*00301, 3*00101 | 00102, 00501 | 001 | 006 | 00201 | 00101 |
| 144 | 00201, 00302 | 3*00101, 3*00201 | 011 | | | | |
| 145 | 00201, 00302 | 3*00101, 3*00201 | 00102, 011 | | | | |
| 146 | 00201, 00302 | 3*00101, 3*00201 | 00801 | | | | |
| 147 | 00201, 00302 | 3*00101, 3*00201 | 00102, 00501 | 001 | | 00201 | |
| 148 | 00302 | 3*00101 | 00102, 011 | | | | |
| 149 | 00201, 00302 | 3*00101, 3*015 | 00501, 006 | 005 | | 00201 | |
| 150 | 00201 | 3*00201, 3*022 | 00102 | | | | |
| 151 | 00201, 00302 | 3*00101, 3*00201 | 00102, 00501 | 001 | | 00201 | |
| 152 | 00302 | 3*00101 | 00102 | | | | |
| 153 | 00201, 00302 | 3*00101, 3*00201 | 00103, 00801 | | | | |
| 154 | 00302 | 3*00101 | 00102 | | | | |
| 155 | 00302 | 3*00101 | 00102 | | | | |
| 156 | 00201, 00302 | 3*00101, 3*00201 | 00102, 00801 | | | | |
| 157 | 00201 | 2*00301, 3*00201 | 00102, 00801 | | | | 00101 |
| 158 | 00302 | 3*00101 | 00102, 00501 | 005 | | 00201 | |
| 159 | 00201, 00302 | 3*00101, 3*00201 | 00102 | | | | |
| 160 | 00201, 00302 | 3*00101, 3*00201 | 00102, 006 | | | | |
| 161 | 00302 | 3*00101 | 00102, 00801 | | | | |
| 162 | 00302 | 3*00101 | 00102 | | | | |
| 163 | 00201, 00302 | 3*00101, 3*00201 | 00102, 00501 | 001 | | 00201 | |
| 164 | 00302, 00401 | 2*00301, 3*00101 | 00102, 00103 | | 010 | | 00101 |
| 165 | 00201, 00302 | 3*00101, 3*00201 | 00102 | | | | |
| 166 | 00201 | 3*00201 | 00102, 00501 | 001 | | 00201 | |
| 167 | 00201, 00302 | 3*00101, 3*00201 | 00501, 006 | 001 | | 00201 | |
| 168 | 00302 | 3*00101 | 00102, 00801 | | | | |
| 169 | 00302 | 3*00101 | 00102, 011 | | | | |
| 170 | 00302 | 3*00101 | 00102 | | | | |
| 171 | 00201, 00302 | 3*00101, 3*00201 | 00501, 00801 | | | | |
| 172 | 00302 | 3*00101, 3*023 | 00102, 011 | | | | |
| 173 | 00302 | 3*00101 | 00102 | | | | |
| 174 | 00302 | 3*00101 | 00501, 00801 | 001 | | 00201 | |
| 175 | 00201, 00302 | 3*00101, 3*00201 | 00102, 00501 | 001 | | 00201 | |
| 176 | 00201, 00302 | 3*00101, 3*00201 | 00102, 00103 | | | | |
| 177 | 00302 | 3*00101, 3*00109 | 00501, 033 | 005 | | 00201 | |
| 178 | 00201, 00302 | 3*00101, 3*00201 | 00102, 00103 | | | | |
| 179 | 00302 | 3*00101 | 00102, 00103 | | | | |
| 180 | 00302 | 3*00101 | 00102, 00501 | 005 | | 00201 | |
| 181 | 00302 | 3*00101 | 00102, 00501 | 005 | | 00201 | |
| 182 | 00302 | 3*00101 | 00102, 00501 | 001 | | 00201 | |
| 183 | 00302 | 3*00101, 3*023 | 00102, 006 | | | | |
| 184 | 00302 | 2*00301, 013, 3*00101 | 00102, 006 | | | | 00101 |
| 185 | 00302 | 3*00101 | 00102 | | | | |
| 186 | 00302 | 3*00101 | 00102, 00501 | 001 | | 00201 | |
| 187 | 00302 | 2*00301, 3*00101 | 00102, 00501 | | | | 00101 |
| 188 | 00302 | 3*00101, 3*021 | 00102, 00103 | | | | |
| 189 | 00201, 00302 | 3*022, 3*023 | 00102 | | | | |
| 190 | 00302 | 2*00301, 3*00101 | 00501 | 001 | 006 | 00201, 006 | 00101 |
| 191 | 00302 | 3*00101 | 00102 | | | | |
| 192 | 00302 | 3*00101 | 00102, 011 | | | | |
| 193 | 00302 | 3*00101 | 00102, 00501 | 001 | | 00201 | |
| 194 | 00302 | 2*00301, 3*00101 | 00103, 00801 | | | | 00101 |
| 195 | 00302 | 3*00101 | 00102 | | | | |
| 196 | 00302 | 3*00101 | 00102, 00801 | | | | |
| 197 | 00302 | 3*00101 | 00102 | | | | |
| 198 | 00302 | 3*00101 | 00102, 00501 | 005 | | 00201 | |
| 199 | 00302 | 3*00101 | 00102 | | | | |
| 200 | 00302 | 3*00101 | 00102, 00801 | | | | |
| 201 | 00302 | 3*00101 | 006, 00801 | | | | |
| 202 | 00201, 00302 | 3*00101, 3*00201 | 00102 | | | | |
| 203 | 00302 | 3*00101 | 00102 | | | | |
| 204 | 00302 | 2*00301, 3*00101 | 00501, 011 | 001 | 006 | 00201 | 00101 |
| 205 | 00302, 00401 | 2*00301, 3*00101 | 00102 | | 010 | | 00101 |
| 206 | 00201, 00302 | 3*00101, 3*00201 | 011 | | | | |
| 207 | 00302 | 2*00301, 3*00101 | 00102 | | | | 00101 |
| 208 | 00302 | 3*00101, 3*00110 | 00102, 00501 | | | | |
| 209 | 00302 | 3*00101 | 00102 | | | | |
| 210 | 00302 | 3*00101 | 00102 | | | | |
| 211 | 00302 | 2*00301, 3*00101 | 00102, 011 | | | | 00101 |
| 212 | 00201, 00302 | 3*00101, 3*00201 | 00501, 006 | 001 | | 00201 | |
| 213 | 00302 | 3*00101 | 00501, 011 | 005 | | | |
| 214 | 00201 | 2*00301, 3*00201 | 00102, 00103 | | | | 00101 |
| 215 | 00302 | 3*00101 | 00102 | | | | |
| 216 | 00302, 00401 | 2*00301, 3*00101 | 00102, 006 | | 002 | | 00101 |
| 217 | 00302 | 3*00101 | 00102, 00501 | 001 | | 00201 | |
| 218 | 00302 | 3*00101 | 00102 | | | | |
| 219 | 00201, 00302 | 3*00101, 3*00201 | 00102, 00501 | 001 | | 00201 | |

TABLE 6-continued

SBT Results of 14 Functional KIR Genes in Southern Chinese Han Population (n = 306)

| | | | | | | | |
|---|---|---|---|---|---|---|---|
| 220 | 00201, 00302 | 3*00101, 3*00201 | 00102, 011 | | | | |
| 221 | 00302 | 2*00301, 3*00101 | 00102, 00501 | 005 | 010 | 00201 | 00101 |
| 222 | 00302 | 2*00301, 3*00101 | 00501 | 001 | 006 | 00201 | 00101 |
| 223 | 00302 | 3*00101 | 00102, 00801 | | | | |
| 224 | 00302 | 3*00101 | 00102 | | | | |
| 225 | 00302 | 3*00101 | 00102, 00501 | 005 | | 00201 | |
| 226 | 00302 | 3*00101 | 00102 | | | | |
| 227 | 00302 | 3*00101 | 00102, 00501 | 001 | | 00201 | |
| 228 | 00302 | 3*00101 | 00102 | | | | |
| 229 | 00401 | 2*00101, 2*00301 | 00102, 00501 | 005 | 010 | | 00101 |
| 230 | 00201, 00302 | 3*00101, 3*00201 | 00102, 011 | | | | |
| 231 | 00302 | 2*00301, 3*00101 | 00102, 00501 | 001 | 006 | 00201 | 00101 |
| 232 | 00302 | 3*00101 | 00102 | | | | |
| 233 | 00201, 00302 | 3*00101, 3*00201 | 00801, 011 | | | | |
| 234 | 00302 | 2*00301, 3*00101 | 00501, 00801 | 001 | 006 | | 00101 |
| 235 | 00302 | 3*00101 | 00102, 011 | | | | |
| 236 | 00302 | 3*00101 | 00102, 011 | | | | |
| 237 | 00201 | 3*00201 | 00501, 006 | 005 | | 00201 | |
| 238 | 00302 | 3*00101 | 00102, 00501 | 005 | | 00201 | |
| 239 | 00302 | 3*00101 | 00102, 006 | | | | |
| 240 | 00302 | 3*00101 | 00102, 00103 | | | | |
| 241 | 00302 | 3*00101 | 00102 | | | | |
| 242 | 00302 | 3*00101 | 00102 | | | | |
| 243 | 00201, 00302 | 3*00101, 3*00201 | 00102, 011 | | | | |
| 244 | 00302 | 3*00101 | 00102 | | | | |
| 245 | 00302 | 3*00101 | 00102, 00501 | 005 | | 00201 | |
| 246 | 00302 | 2*00301, 3*00101 | 006, 00801 | | | | 00101 |
| 247 | 00302 | 3*00101, 3*026 | 006 | | | | |
| 248 | 00302 | 3*00101 | 00102 | | | | |
| 249 | 00302 | 3*00101 | 00102 | | | | |
| 250 | 00302 | 3*00101 | 00501, 006 | 005 | | 00201 | |
| 251 | 00201, 00302 | 3*00101, 3*00201 | 00102, 011 | | | | |
| 252 | 00302 | 3*00101 | 00102 | | | | |
| 253 | 00302 | 2*00301, 3*00101 | 00102, 00501 | 001 | 006 | 00201 | 00101 |
| 254 | 00201, 00302 | 3*00101, 3*00201 | 00102, 011 | | | | |
| 255 | 00302 | 3*00101 | 00102, 00501 | 005 | | 00201 | |
| 256 | 00201, 00302 | 3*00201, 3*031 | 00102, 006 | | | | |
| 257 | 00201, 00302 | 3*00101, 3*00201 | 00102, 00501 | 001 | | 00201 | |
| 258 | 00302 | 3*00101 | 00102, 00501 | | | | |
| 259 | 00302 | 3*00101 | 00103, 011 | | | | |
| 260 | 00201, 00302 | 3*00101, 3*00201 | 00501, 011 | 001 | | 00201 | |
| 261 | 00201, 00302 | 3*00101, 3*00201 | 00102, 00103 | | | | |
| 262 | 00302 | 2*00301, 3*00101 | 00501, 011 | 005 | 010 | 00201 | 00101 |
| 263 | 00302 | 3*00101 | 00102, 011 | | | | |
| 264 | 00302 | 3*00101 | 00102, 034 | 001 | | 00201 | |
| 265 | 00302 | 3*00101 | 00501 | 001 | | 00201 | |
| 266 | 00302 | 3*00101 | 00102, 00501 | 001 | | 00202 | |
| 267 | 00201, 00302 | 3*00101, 3*00201 | 006, 011 | | | | |
| 268 | 00302 | 3*00101 | 00102, 032 | | | | |
| 269 | 00201, 00302 | 3*00101, 3*00201 | 00102, 006 | | | | |
| 270 | 00302 | 3*00101 | 00102, 00801 | | | | |
| 271 | 00201, 00302 | 3*00101, 3*00201 | 006, 011 | 001 | | 00201 | |
| 272 | 00302, 00401 | 2*00301, 3*00101 | 00102 | | 010 | | 00101 |
| 273 | 00201, 00302 | 3*00101, 3*00201 | 006, 011 | | | | |
| 274 | 00201, 00302 | 3*00101, 3*00201 | 006, 011 | | | | |
| 275 | 00302 | 2*00301, 3*00101 | 00102, 00501 | 001 | 006 | 00201 | 00101 |
| 276 | 00304 | 2*00301, 3*00101 | 00102, 011 | | | | 00101 |
| 277 | 00302 | 3*00101, 3*023 | 00102 | | | | |
| 278 | 00302 | 3*00101, 3*023 | 00102 | | | | |
| 279 | 00201, 00302 | 3*00101, 3*00201 | 00102, 00103 | | | | |
| 280 | 00201, 00302 | 3*00101, 3*00201 | 00102 | | | | |
| 281 | 00302 | 3*00101 | 00501, 011 | 005 | | 00201 | |
| 282 | 00302, 033 | 3*00101 | 00102 | | | | |
| 283 | 00302 | 3*00101 | 00501, 00801 | 001 | | 00201 | |
| 284 | 00302 | 3*00101 | 00102, 00501 | | | | |
| 285 | 00302 | 3*00101 | 00102, 00501 | 001 | | 00201 | |
| 286 | 00302, 00401 | 2*00101, 3*00101 | 00102, 00501 | 005 | 002 | | 00101 |
| 287 | 00302 | 3*00101 | 00102 | | | | |
| 288 | 00302 | 3*00101 | 00103, 006 | | | | |
| 289 | 00201, 00302 | 3*00101, 3*00201 | 006, 011 | | | | |
| 290 | 00302 | 3*00101 | 00102, 00501 | | | | |
| 291 | | 2*00301 | 00102, 00501 | 001 | 006 | 00201 | 00101 |
| 292 | 00302 | 3*00101 | 011 | | | | |
| 293 | 00302 | 3*00101 | 00102 | | | | |
| 294 | 00302 | 3*00101 | 00102 | | | | |
| 295 | 00302 | 3*00101 | 00102, 006 | | | | |
| 296 | 00302 | 3*00101 | 00102 | | | | |
| 297 | 00302 | 2*00301, 3*00101 | 00102 | | 006 | 00201 | 00101 |

TABLE 6-continued

SBT Results of 14 Functional KIR Genes in Southern Chinese Han Population (n = 306)

| | | | | | | |
|---|---|---|---|---|---|---|
| 298 | 00302 | 3*00101 | 00102, 00501 | 005 | 00201 | |
| 299 | 00302 | 3*00101 | 00102, 006 | | | |
| 300 | 00302 | 2*00301, 3*00101 | 00102, 00801 | | | 00101 |
| 301 | 00302 | 3*00101 | 00102, 00801 | | | |
| 302 | 00302 | 3*00101, 3*026 | 00103, 006 | | | |
| 303 | 00302 | 3*00101 | 00103, 00501 | 005 | 00201 | |
| 304 | 00201, 00302 | 3*00101, 3*00201 | 00103 | | | |
| 305 | 00302, 034 | 3*00101, 3*00201 | 00102 | | | |
| 306 | 00302 | 3*00101 | 00102 | | | |

| No. | 2DS3 | 2DS4 | 2DS5 | 3DL1/S1 | 3DL2 | 3DL3 |
|---|---|---|---|---|---|---|
| 1 | 00201 | 00101 | | L1*01502, S1*01301, S1*082 | 00701, 039 | 010 |
| 2 | | 010 | | L1*00501 | 010 | 010 |
| 3 | | 00101, 00301 | | L1*00101, L1*01502 | 001, 002 | 008, 009 |
| 4 | | 00301, 00401 | | L1*00101, L1*00701 | 008, 010 | 010 |
| 5 | | 00101, 010 | | L1*00501, L1*01502 | 002, 010 | 010 |
| 6 | | 00101 | | L1*01502 | 002 | 008 |
| 7 | 00201 | 00105 | | L1*01502, S1*01301 | 002, 00701 | 008, 010 |
| 8 | | 00101 | 00201 | L1*01502, S1*01301 | 002, 093 | 009, 010 |
| 9 | | 00101, 00301 | | L1*00101, L1*01502 | 001, 002 | 001, 008 |
| 10 | | 00401 | 00201 | L1*00701, S1*01301 | 002, 008 | 001, 009 |
| 11 | | 00101, 010 | | L1*00501, L1*01502 | 002, 010 | 008, 009 |
| 12 | | 00101 | 00201 | L1*01502, S1*01301 | 002 | 048 |
| 13 | | 00101 | | L1*01502 | 002 | 009, 010 |
| 14 | | 00101, 00401 | | L1*01502, L1*00701 | 002, 008 | 009, 010 |
| 15 | | 00101 | | L1*01502 | 002 | 008 |
| 16 | | 00101 | | L1*01502 | 002, 039 | 008, 028 |
| 17 | | 00101, 010 | | L1*00501, L1*01502 | 002, 010 | 009, 010 |
| 18 | | 018 | 00201 | L1*00501, S1*01301 | 001, 010 | 006, 010 |
| 19 | | 00101, 00401 | | L1*01502, L1*00701 | 002, 008 | 008, 009 |
| 20 | 00201 | | 00201 | S1*01301 | 00701 | 008, 010 |
| 21 | | 00101 | 00201 | L1*01502 | 00701, 039 | 008, 010 |
| 22 | | 00101, 010 | | L1*00501, L1*01502 | 002 | 010 |
| 23 | | 00101, 00301 | | L1*00101, L1*01502 | 001, 002 | 008, 010 |
| 24 | | 00101 | | L1*01502, L1*02901 | 002 | 009, 010 |
| 25 | 001 | 00101, 00401 | | L1*01502, L1*00701 | 002, 010 | 008, 009 |
| 26 | 001 | 00101 | 00201 | L1*01502, S1*01301 | 002, 015 | 010, 028 |
| 27 | | 00101, 00401 | | L1*01502, L1*00701 | 002, 008 | 008, 010 |
| 28 | | | | | | |
| 29 | | 00101, 00401 | | L1*01502, L1*00701 | 002, 008 | 009, 048 |
| 30 | | 00101 | 00201 | L1*020, S1*01301 | 002, 009 | 010, 028 |
| 31 | 001, 00201 | | 00201 | S1*01301 | 002, 00701 | 004, 015 |
| 32 | | 00101 | 00201 | L1*01502 | 002, 00701 | 008, 010 |
| 33 | | 010 | 00201 | L1*00501, S1*01301, S1*084 | 002, 00701 | 001, 04802 |
| 34 | | 00101, 010 | | L1*00501, L1*01502 | 002, 010 | 001, 002 |
| 35 | | 00101 | 00201 | L1*01502, S1*01301 | 002 | 008, 015 |
| 36 | 001 | 00101 | | L1*01502, L1*02901 | 002 | 010 |
| 37 | | 00101 | 00201 | L1*01502, S1*01301 | 002, 093 | 008, 010 |
| 38 | | 00101 | | L1*01502 | 002 | 010, 015 |
| 39 | | 00101 | | L1*01502 | 002 | 009 |
| 40 | | 00101 | | L1*01502 | 002 | 009 |
| 41 | | 00101 | | L1*01502 | 002 | 008, 010 |
| 42 | | | 00201 | S1*01301 | 00701 | 008, 010 |
| 43 | 001 | 00101 | | L1*01502 | 002 | 008, 010 |
| 44 | | 00101 | | L1*01502 | 002 | 008, 010 |
| 45 | 00201 | 00401 | | L1*00701, S1*01301 | 00701, 008 | 008, 010 |
| 46 | | 00101 | 00201 | L1*01502, S1*01301 | 002 | 009, 010 |
| 47 | | 00301, 010 | | L1*00101, L1*00501 | 001, 010 | 010 |
| 48 | 001 | 00101 | | L1*01502, S1*01301, S1*082 | 002 | 009 |
| 49 | | 00301, 010 | | L1*00501, L1*008 | 009, 010 | 009, 010 |
| 50 | 001 | 00101 | | L1*01502 | 002, 039 | 010, 028 |
| 51 | | 00401 | 00201 | L1*00701, S1*01301 | 00701, 008 | 001, 010 |
| 52 | | 00101, 010 | | L1*00501, L1*01502 | 002, 010 | 009 |
| 53 | | 00101, 010 | | L1*00501, L1*01502 | 002, 010 | 008, 010 |
| 54 | 001 | | 00201 | S1*01301 | 00701 | 001, 048 |
| 55 | | 00101, 010 | | L1*00501, L1*01502 | 002, 010 | 010, 04802 |
| 56 | 00201 | 00101 | | L1*01502, S1*01301 | 002, 00707 | 009, 010 |
| 57 | | 00101 | | L1*01502 | 002 | 006, 010 |
| 58 | | 010 | | L1*00501 | 010 | 009, 010 |
| 59 | | 00101 | | L1*01502 | 002 | 010 |
| 60 | | 00101 | | L1*01502 | 002 | 009, 010 |
| 61 | | 00101 | | L1*00501, L1*01502 | 002, 039 | 010 |
| 62 | | 00101 | 00201 | L1*01502, S1*01301, S1*083 | 001, 015 | 008 |

TABLE 6-continued

SBT Results of 14 Functional KIR Genes in Southern Chinese Han Population (n = 306)

| | | | | | | |
|---|---|---|---|---|---|---|
| 63 | | 00101, 010 | | L1*00501, L1*01502 | 002, 010 | 002, 010 |
| 64 | | 00101, 00401 | | L1*01502, L1*00701 | 002, 021 | 010 |
| 65 | | 00101, 00401 | | L1*01502, L1*00701 | 008, 010 | 006, 010 |
| 66 | 001 | 00101, 00301 | | L1*00101, L1*01502 | 001, 002 | 003, 004 |
| 67 | | 00301, 00401 | | L1*00101, L1*00701 | 001, 008 | 010 |
| 68 | | 00101 | | L1*01502 | 002 | 010 |
| 69 | | 010 | 00201 | L1*00501 | 002, 00701 | 02602 |
| 70 | | 010 | 00201 | L1*00501, S1*01301, S1*078 | 001, 00701 | 006, 010 |
| 71 | 001 | 00101 | | L1*01502, L1*020 | 002, 009 | 010 |
| 72 | | 010 | | L1*00501 | 010 | 010 |
| 73 | | 00101 | 00201 | L1*01502, S1*01301 | 002, 00701 | 008, 010 |
| 74 | | 00101, 010 | | L1*00501, L1*01502 | 002, 010 | 009, 010 |
| 75 | | 00101 | | L1*01502 | 002 | 010, 02602 |
| 76 | | 00101 | 00201 | L1*01502, S1*01301 | 002, 093 | 010 |
| 77 | | 00101 | | L1*01502 | 002 | 008, 009 |
| 78 | 001 | 00101 | 00201 | L1*01502, S1*01301 | 002, 00701 | 010 |
| 79 | | 010 | 00201 | L1*00501, S1*01301 | 002 | 006, 009 |
| 80 | | 00101 | | L1*01502 | 002 | 006, 010 |
| 81 | | 00101 | 00201 | L1*01502, S1*01301 | 002, 00701 | 009 |
| 82 | 00201 | 00301 | | L1*00101, S1*01301 | 001, 00707 | 010 |
| 83 | | 00301, 00401 | | L1*00701, L1*070 | 001, 008 | 006, 010 |
| 84 | | 00101 | | L1*01502 | 002 | 008, 010 |
| 85 | | 00101, 010 | | L1*00501, L1*01502 | 002, 010 | 010 |
| 86 | | 00101 | | L1*01502 | 002 | 001, 010 |
| 87 | | 00101 | | L1*01502 | 002 | 008, 010 |
| 88 | | 00101 | | L1*01502 | 002 | 010, 015 |
| 89 | | 00101 | | L1*01502, L1*020 | 001, 002 | 010 |
| 90 | 00201 | 00101 | | L1*020, S1*01301 | 00701, 009 | 008, 010 |
| 91 | | 010 | 00201 | L1*00501, S1*01301 | 00701, 010 | 010 |
| 92 | | 00101, 010 | | L1*01502, L1*01502 | 002, 010 | 008, 010 |
| 93 | | 00101 | 00201 | L1*01502, S1*01301 | 002, 00701 | 009, 015 |
| 94 | | 00101, 010 | | L1*00501, L1*01502 | 002, 010 | 008, 010 |
| 95 | | 00101 | 00201 | L1*01502, S1*01301 | 002 | 009, 01003 |
| 96 | | 00101 | | L1*01502 | 002 | 010 |
| 97 | | 00101, 00401 | | L1*01502, L1*00701 | 002, 009 | 009 |
| 98 | | 00401, 010 | | L1*00501, L1*00701 | 008, 010 | 006, 010 |
| 99 | | 00101, 010 | | L1*00501, L1*01502 | 002, 010 | 008, 04802 |
| 100 | | 00101 | 00201 | L1*02901, S1*01301 | 002, 00701 | 010 |
| 101 | | 00101 | | L1*01502 | 002 | 001, 010 |
| 102 | 00201 | | 00201 | S1*01301 | 00701, 027 | 010 |
| 103 | 001 | 00101 | 00201 | L1*01502 | 002, 00701 | 004, 028 |
| 104 | | 00101 | 00201 | L1*020, S1*01301 | 002, 009 | 010, 064 |
| 105 | 00201 | 00101, 010 | | L1*00101, S1*01301 | 001, 00701 | 009, 010 |
| 106 | | 00101, 00301 | | L1*00101, L1*01502 | 001, 002 | 010 |
| 107 | | 00101, 00401 | | L1*01502, L1*00701 | 002, 021 | 010 |
| 108 | 00201 | 00101 | | L1*01502 | 002, 00701 | 010 |
| 109 | | 00101, 010 | | L1*00501, L1*01502 | 002 | 010, 04802 |
| 110 | | 010 | 00201 | L1*00501, S1*01301 | 00701, 010 | 008, 009 |
| 111 | | 00101, 010 | | L1*00501, L1*01502 | 002 | 009, 010 |
| 112 | 001, 00201 | 010 | | L1*00501, S1*01301 | 00701, 010 | 010 |
| 113 | | 00101, 00301 | | L1*00101, L1*020 | 002, 009 | 009, 015 |
| 114 | | 00101, 010 | | L1*00501, L1*01502 | 002, 010 | 010, 015 |
| 115 | | 00101, 00401 | | L1*01502, L1*00701 | 002, 008 | 008 |
| 116 | | 00101, 010 | | L1*00501, L1*01502 | 002, 010 | 008, 009 |
| 117 | | 00101, 00301 | | L1*00101, L1*01502 | 001, 002 | 010 |
| 118 | | 00101, 00401 | | L1*01502, L1*00701 | 039, 083 | 006, 010 |
| 119 | | 010 | 00201 | L1*00501, S1*01301 | 002 | 008 |
| 120 | | 010 | | L1*00501, L1*00502 | 010, 021 | 010 |
| 121 | | 010 | 00201 | L1*00501, S1*01301 | 002, 010 | 006, 009 |
| 122 | | 00101, 010 | | L1*00501, L1*01502 | 002, 010 | 010 |
| 123 | | 00101 | | L1*01502, S1*01301 | 002 | 010 |
| 124 | | | 00201 | S1*01301 | 00701 | 028 |
| 125 | 00201 | 00101 | | L1*01502, S1*01301 | 002, 00701 | 010, 015 |
| 126 | | 00101, 00401 | | L1*01502, L1*00701 | 002, 016 | 008, 048 |
| 127 | | 00101 | 00201 | L1*01502, S1*01301 | 039, 093 | 008, 010 |
| 128 | | 00101 | | L1*01502 | 002 | 009 |
| 129 | | 00101 | | L1*01502 | 002 | 008, 010 |
| 130 | | 00101 | 00201 | L1*01502, S1*01301 | 039, 093 | 010 |
| 131 | | 00101 | | L1*01502, L1*020 | 002, 009 | 010 |
| 132 | | 00101 | 00201 | L1*01502, S1*01301 | 002, 00701 | 004, 028 |
| 133 | | 00401 | | L1*00701 | 008 | 008, 015 |
| 134 | 00201 | 00101 | | L1*01502, S1*01301 | 002, 00701 | 009, 015 |
| 135 | | 00401 | 00201 | L1*00701, S1*01301 | 002, 008 | 009, 010 |
| 136 | | 00101 | | L1*01502, L1*020 | 010, 039 | 008, 010 |
| 137 | | 00101 | | L1*01502, L1*02901 | 002, 010 | 010 |
| 138 | | 00101, 010 | | L1*00501, L1*01502 | 002, 010 | 008 |
| 139 | | 00101 | 00201 | L1*01502, S1*01301 | 002, 00701 | 009, 010 |

TABLE 6-continued

SBT Results of 14 Functional KIR Genes in Southern Chinese Han Population (n = 306)

| # | | | | | | |
|---|---|---|---|---|---|---|
| 140 | | 00101 | 00201 | L1*01502, S1*01301 | 002, 015 | 006, 009 |
| 141 | | 00101 | 00201 | L1*01502, S1*01301 | 002 | 001, 006 |
| 142 | | 00101, 00301 | | L1*00101, L1*01502 | 002, 010 | 010, 015 |
| 143 | | 00101 | 00201 | L1*01502, S1*01301 | 002, 00701 | 010 |
| 144 | | 010 | | L1*00501 | 002, 010 | 001, 010 |
| 145 | | 00101, 010 | | L1*00501, L1*01502 | 002, 010 | 006, 010 |
| 146 | | 00301, 00401 | | L1*00101, L1*00701 | 008, 016 | 008, 064 |
| 147 | | 00101 | 00201 | L1*01502, S1*01301 | 002 | 010, 013 |
| 148 | | 00101, 010 | | L1*00501, L1*01502 | 002, 010 | 008, 010 |
| 149 | 00201 | 00401 | | L1*00701, S1*01301 | 00701, 008 | 010, 04802 |
| 150 | | 00101 | | L1*01502 | 002 | 001, 063 |
| 151 | | 00101 | 00201 | L1*01502, S1*01301 | 002, 00701 | 006, 009 |
| 152 | | 00101 | | L1*01502 | 002 | 010 |
| 153 | | 00101, 00301 | | L1*00101, L1*020 | 001, 009 | 001, 010 |
| 154 | | 00101 | | L1*01502 | 002 | 008, 010 |
| 155 | | 00101 | | L1*01502 | 002 | 008 |
| 156 | | 00101, 00301 | | L1*00101, L1*01502 | 002, 010 | 010, 02602 |
| 157 | | 00101, 010 | | L1*00501, L1*01502 | 002, 010 | 006, 02602 |
| 158 | 00201 | 00101 | | L1*01502, S1*01301 | 002, 00701 | 008, 010 |
| 159 | | 00101 | | L1*01502 | 002 | 001, 008 |
| 160 | | 00101, 00401 | | L1*01502, L1*00701 | 002, 008 | 010, 065 |
| 161 | | 00101, 00301 | | L1*00101, L1*01502 | 001, 002 | 008 |
| 162 | | 00101 | 00201 | L1*01502 | 002 | 008, 009 |
| 163 | | 00101 | | L1*01502 | 002 | 010 |
| | | | 00201 | L1*02901, S1*01301 | 002, 00701 | 001, 010 |
| 164 | 001 | 00101 | | L1*01502, L1*020 | 002 | 008, 010 |
| 165 | | 00101 | | L1*01502 | 002, 039 | 010, 062 |
| 166 | | 00101 | 00201 | L1*01502, S1*01301 | 002, 010 | 001 |
| 167 | | 00401 | 00201 | L1*00701, S1*01301 | 00701, 008 | 001, 010 |
| 168 | | 00101, 00301 | | L1*00101, L1*01502 | 001, 093 | 010 |
| 169 | | 00101, 010 | | L1*00501, L1*01502 | 002, 010 | 008, 009 |
| 170 | | 00101 | | L1*01502 | 002 | 010 |
| 171 | | 00401, 010 | | L1*00501, L1*00701 | 008, 010 | 001, 008 |
| 172 | | 00101, 010 | | L1*00501, L1*01502 | 002 | 009, 010 |
| 173 | | 00101 | | L1*01502 | 002 | 008, 010 |
| 174 | | 00301 | 00201 | L1*00101, S1*01301 | 001, 00701 | 008, 010 |
| 175 | | 00101 | 00201 | L1*01502, S1*01301 | 002 | 006, 008 |
| 176 | | 00101 | | L1*01502, L1*020 | 002, 009 | 010, 062 |
| 177 | 00201 | 00101 | | L1*01502, S1*01301 | 002, 00701 | 010 |
| 178 | | 00101 | | L1*01502, L1*020 | 002, 009 | 009, 048 |
| 179 | | 00101 | | L1*01502, L1*020 | 009, 021 | 010 |
| 180 | 00201 | 00101 | | L1*01502, S1*01301 | 002, 00701 | 010 |
| 181 | 00201 | 00101 | | L1*01502, S1*01301 | 002, 00701 | 010 |
| 182 | | 00101 | 00201 | L1*01502, S1*01301 | 002, 00701 | 008, 010 |
| 183 | | 00101, 00401 | | L1*01502, L1*00701 | 002, 008 | 009, 010 |
| 184 | | 00101, 00401 | | L1*01502, L1*00701 | 002, 021 | 008, 010 |
| 185 | | 00101 | | L1*01502, L1*01505 | 002 | 010 |
| 186 | | 00101 | 00201 | L1*01502, S1*01301 | 00701, 010 | 010 |
| 187 | | 00101 | | L1*01502, L1*020 | 002, 009 | 010, 015 |
| 188 | | 00101, 00401 | | L1*01502, L1*00701 | 002, 008 | 009, 010 |
| 189 | | 00101 | | L1*01502 | 002, 039 | 010, 04802 |
| 190 | | | 00201 | S1*01301 | 002, 00701 | 001, 048 |
| 191 | | 00101 | | L1*01502 | 002 | 009, 010 |
| 192 | | 00101, 010 | | L1*00501, L1*01502 | 002 | 010 |
| 193 | | 00101 | 00201 | L1*01502, S1*01301 | 002, 00701 | 009 |
| 194 | | 00101, 00301 | | L1*00101, L1*020 | 009, 010 | 003, 010 |
| 195 | | 00101 | | L1*01502 | 002 | 009, 010 |
| 196 | | 00101, 00301 | | L1*00101, L1*01502 | 001, 002 | 010, 015 |
| 197 | | 00101 | | L1*01502 | 002, 010 | 008 |
| 198 | 00201 | 00101 | | L1*01502, S1*01301 | 002, 00701 | 009 |
| 199 | | 00101 | | L1*01502 | 001, 002 | 009, 010 |
| 200 | | 00101, 00301 | | L1*00101, L1*01502 | 001, 002 | 008, 010 |
| 201 | | 00301, 00401 | | L1*00101, L1*00701 | 001, 009 | 009, 010 |
| 202 | | 00101 | | L1*01502 | 002, 039 | 006, 010 |
| 203 | | 00101 | | L1*01502 | 002, 039 | 008 |
| 204 | | 010 | 00201 | L1*00501, S1*01301 | 002, 091 | 010, 028 |
| 205 | 001 | 00101 | | L1*01502 | 002 | 010 |
| 206 | | 010 | | L1*00501 | 010 | 006, 010 |
| 207 | | 00101 | | L1*01502 | 002 | 009, 010 |
| 208 | | 00101 | | L1*01502, S1*01301 | 002 | 009, 010 |
| 209 | | 00101 | | L1*01502 | 002 | 008, 010 |
| 210 | | 00101 | | L1*01502 | 002 | 008, 010 |
| 211 | | 00101, 010 | | L1*00501, L1*01502 | 010, 039 | 008, 009 |
| 212 | | 00401 | 00201 | L1*00701, S1*01301 | 00701, 008 | 008, 04802 |
| 213 | 00201 | 010 | | L1*00501, S1*01301 | 00706, 010 | 009, 015 |
| 214 | | 00101 | | L1*020, L1*02901 | 002, 009 | 02602, 04802 |
| 215 | | 00101 | | L1*01502 | 002 | 009 |
| 216 | 001 | 00101, 00401 | | L1*01502, L1*00701 | 002, 008 | 008, 009 |
| 217 | | 00101 | 00201 | L1*01502, S1*01301 | 002 | 010 |

TABLE 6-continued

SBT Results of 14 Functional KIR Genes in Southern Chinese Han Population (n = 306)

| | | | | | |
|---|---|---|---|---|---|
| 218 | | 00101 | | L1*01502 | 002 | 009, 010 |
| 219 | | 00101 | 00201 | L1*01502, S1*01301 | 002 | 006, 010 |
| 220 | | 00101, 010 | | L1*00501, L1*01502 | 002, 021 | 010, 02602 |
| 221 | 00201 | 00101 | | L1*01502, S1*01301 | 001, 010 | 008 |
| 222 | | | 00201 | S1*01301 | 00701, 015 | 010 |
| 223 | | 00101, 00301 | | L1*00101, L1*01502 | 002, 010 | 008, 010 |
| 224 | | 00101 | | L1*01502 | 002 | 010, 015 |
| 225 | 00201 | 00101 | | L1*01502, S1*01301 | 002, 015 | 009, 010 |
| 226 | | 00101 | | L1*01502 | 002 | 010 |
| 227 | | 00101 | 00201 | L1*01502, S1*01301 | 002 | 002, 010 |
| 228 | | 00101 | | L1*01502 | 002 | 008, 009 |
| 229 | 001 | 010 | | L1*01502, L1*00501, S1*01301 | 002, 010 | 003, 028 |
| 230 | | 00101, 010 | | L1*00501, L1*01502 | 002, 010 | 010, 065 |
| 231 | | 00101 | 00201 | L1*01502, S1*01301 | 002, 00701 | 008, 010 |
| 232 | | 00101 | | L1*01502 | 002 | 009, 010 |
| 233 | | 00301, 010 | | L1*00101, L1*00501 | 001, 002 | 001, 009 |
| 234 | | 00301 | 00201 | L1*00101, S1*01301 | 001, 002 | 010 |
| 235 | | 00101, 010 | | L1*00501, L1*01502 | 002 | 010 |
| 236 | | 00101, 010 | | L1*00501, L1*01502 | 002, 010 | 008, 009 |
| 237 | 00201 | 00401 | | L1*00701, S1*01301 | 00701, 008 | 001, 006 |
| 238 | 00201 | 00101 | | L1*01502, S1*01301 | 002, 027 | 008, 010 |
| 239 | | 00101, 00401 | | L1*01502, L1*00701 | 002, 008 | 009, 010 |
| 240 | | 00101 | | L1*01502, L1*020 | 002, 084 | 008, 015 |
| 241 | | 00101 | | L1*01502 | 002, 039 | 009, 010 |
| 242 | | 00101 | | L1*01502, L1*02901 | 002 | 008, 010 |
| 243 | | 00101, 010 | | L1*00501, L1*01502 | 002, 010 | 010, 04802 |
| 244 | | 00101 | | L1*01502 | 002 | 008, 010 |
| 245 | 00201 | 00101 | | L1*01502, S1*01301 | 002, 00701 | 008, 010 |
| 246 | | 00301, 00401 | | L1*00101, L1*00701 | 001, 008 | 008, 010 |
| 247 | | 00101, 00401 | | L1*01502, L1*00701 | 002, 008 | 010, 015 |
| 248 | | 00101 | | L1*01502 | 002, 00701 | 009, 010 |
| 249 | | 00101 | | L1*01502 | 002, 010 | 009, 010 |
| 250 | 00201 | 00401 | | L1*00701, S1*01301, S1*085 | 00701, 008 | 010 |
| 251 | | 00101, 010 | | L1*00501, L1*01502 | 002, 010 | 001, 015 |
| 252 | | 00101 | | L1*01502 | 002 | 009, 010 |
| 253 | | 017 | 00201 | L1*01502, S1*01301 | 002 | 008, 009 |
| 254 | | 00101, 010 | | L1*00501, L1*01502 | 002, 091 | 006, 009 |
| 255 | 00201 | 00101 | | L1*01502, L1*079, S1*01301 | 00701, 039 | 008, 010 |
| 256 | | 00101, 00401 | | L1*01502, L1*00701 | 002, 008 | 010, 064 |
| 257 | | 00101 | 00201 | L1*01502, S1*01301 | 002, 039 | 006, 008 |
| 258 | | 00101, 010 | | L1*00501, L1*01502 | 00701, 010 | 008, 009 |
| 259 | | 00101, 010 | | L1*00501, L1*020 | 009, 010 | 010 |
| 260 | | 018 | 00201 | L1*00501, S1*01301 | 001, 010 | 006, 009 |
| 261 | | 00101 | | L1*01502, L1*020 | 002, 009 | 010, 063 |
| 262 | 00201 | 010 | | L1*00501, S1*01301 | 00706, 010 | 008 |
| 263 | | 00101, 010 | | L1*00501, L1*01502 | 001, 002 | 008, 010 |
| 264 | | 00101 | 00201 | L1*01502, S1*01301 | 002, 00701 | 010 |
| 265 | | | 00201 | S1*01301 | 002 | 009, 010 |
| 266 | | 00101 | 00201 | L1*01502, S1*01301 | 002, 00701 | 008, 010 |
| 267 | | 00401, 010 | | L1*00501, L1*00701 | 001, 002 | 010, 04802 |
| 268 | | 00101 | | L1*01502 | 002 | 009, 010 |
| 269 | | 00101, 00401 | | L1*01502, L1*00701 | 008, 039 | 008, 04802 |
| 270 | | 00101, 00301 | | L1*01502, L1*070 | 001, 002 | 009, 010 |
| 271 | | 00401 | 00201 | L1*00701, S1*01301 | 002, 008 | 006, 010 |
| 272 | 001 | 00101 | | L1*01502, L1*02901 | 002 | 008, 015 |
| 273 | | 00401, 010 | | L1*00501, L1*00701 | 002, 010 | 010, 04802 |
| 274 | | 00401, 010 | | L1*00501, L1*00701 | 008, 010 | 006, 010 |
| 275 | | 00101 | 00201 | L1*01502, S1*01301 | 002 | 010 |
| 276 | | 00101, 010 | | L1*00501, L1*01502 | 002, 091 | 010 |
| 277 | | 00101 | | L1*01502 | 002 | 008, 010 |
| 278 | | 00101 | | L1*01502 | 002, 099 | 010 |
| 279 | | 00101 | | L1*020, L1*02901 | 002, 009 | 006, 008 |
| 280 | | 00101 | | L1*01502 | 002 | 001, 010 |
| 281 | 00201 | 010 | | L1*00501, S1*01301 | 010, 015 | 010 |
| 282 | | 00101 | | L1*01502 | 002 | 009, 010 |
| 283 | | 00301 | 00201 | L1*00101, S1*01301 | 001, 00701 | 008, 010 |
| 284 | | 00101, 010 | | L1*00501, L1*02901 | 001, 002 | 009, 010 |
| 285 | | 00101 | 00201 | L1*01502, S1*01301 | 002, 00701 | 009, 010 |
| 286 | 001 | 00101, 00401 | | L1*01502, L1*00701, S1*01301 | 002, 008 | 010 |
| 287 | | 00101 | | L1*01502 | 002 | 008, 009 |
| 288 | | 00101, 00401 | | L1*00701, L1*020 | 008, 009 | 010, 015 |
| 289 | | 00401, 010 | | L1*00501, L1*00701 | 010, 016 | 001, 010 |
| 290 | | 00101 | | L1*01502, L1*020, S1*01301 | 002, 009 | 008, 009 |

TABLE 6-continued

SBT Results of 14 Functional KIR Genes in Southern Chinese Han Population (n = 306)

| 291 | | 00101 | 00201 | L1*01502, S1*01301 | 002 | 004, 028 |
|---|---|---|---|---|---|---|
| 292 | | 010 | | L1*00501 | 010 | 008, 010 |
| 293 | | 00101 | | L1*01502 | 002 | 008, 010 |
| 294 | | 00101 | | L1*01502 | 002 | 008, 010 |
| 295 | | 00101, 00401 | | L1*01502, L1*00701 | 002, 008 | 010 |
| 296 | | 00101 | | L1*01502 | 002 | 010 |
| 297 | | 00101 | 00201 | L1*01502 | 002, 00701 | 008, 009 |
| 298 | 00201 | 00101 | | L1*01502, S1*01301 | 002, 00701 | 009, 010 |
| 299 | | 00101, 00401 | | L1*01502, L1*00701 | 002, 008 | 008, 009 |
| 300 | | 00101, 00301 | | L1*00101, L1*01502 | 002, 010 | 009, 010 |
| 301 | | 00101, 00301 | | L1*00101, L1*01502 | 001, 002 | 008, 009 |
| 302 | | 00401 | | L1*00701 | 008 | 001, 010 |
| 303 | 00201 | 00101 | | L1*020, S1*01301, S1*085 | 002, 00701 | 008, 010 |
| 304 | | 00101 | | L1*020 | 002, 009 | 006, 010 |
| 305 | | 00101 | | L1*01502 | 002, 039 | 008, 062 |
| 306 | | 00101 | | L1*01502 | 001, 010 | 010 |

TABLE 7

Alleles and their Frequencies of 14 Functional KIR Genes in Southern Chinese Han Population (n = 306)

| | N | Freq. |
|---|---|---|
| Cen | | |
| KIR3DL3 | | |
| *001 | 24 | 0.078 |
| *002 | 3 | 0.010 |
| *003 | 3 | 0.010 |
| *004 | 5 | 0.016 |
| *006 | 28 | 0.092 |
| *008 | 98 | 0.320 |
| *009 | 85 | 0.278 |
| *010 | 212 | 0.693 |
| *01003 | 1 | 0.003 |
| *013 | 1 | 0.003 |
| *015 | 20 | 0.065 |
| *02602 | 6 | 0.020 |
| *028 | 10 | 0.033 |
| *048 | 6 | 0.020 |
| *04802 | 12 | 0.039 |
| *062 | 3 | 0.010 |
| *063 | 2 | 0.007 |
| *064 | 3 | 0.010 |
| *065 | 2 | 0.007 |
| KIR2DS2 | | |
| *00101 | 65 | 0.212 |
| *009 | 3 | 0.010 |
| neg | 239 | 0.781 |
| KIR2DL5B | | |
| *002 | 10 | 0.033 |
| *006 | 24 | 0.078 |
| *008 | 1 | 0.003 |
| *010 | 14 | 0.046 |
| neg | 259 | 0.846 |
| KIR2DS3 | | |
| *001 | 19 | 0.062 |
| *00201 | 32 | 0.105 |
| neg | 257 | 0.840 |
| KIR2DS5 | | |
| *00201 | 76 | 0.248 |
| neg | 230 | 0.752 |
| KIR2DL2/3 | | |
| 2*00101 | 11 | 0.036 |
| 2*00301 | 58 | 0.190 |
| 2*013 | 1 | 0.003 |
| 3*00101 | 284 | 0.928 |
| 3*00109 | 4 | 0.013 |
| 3*00110 | 1 | 0.003 |
| 3*00201 | 74 | 0.242 |
| 3*015 | 2 | 0.007 |
| 3*019 | 1 | 0.003 |
| 3*021 | 1 | 0.003 |
| 3*022 | 2 | 0.007 |
| 3*023 | 13 | 0.042 |
| 3*025 | 1 | 0.003 |
| 3*026 | 2 | 0.007 |
| 3*027 | 1 | 0.003 |
| 3*028 | 1 | 0.003 |
| 3*029 | 1 | 0.003 |
| 3*031 | 1 | 0.003 |
| KIR2DL1 | | |
| *001 | 1 | 0.003 |
| *00201 | 76 | 0.248 |
| *00302 | 285 | 0.931 |
| *00304 | 1 | 0.003 |
| *00305 | 1 | 0.003 |
| *00401 | 19 | 0.062 |
| *030 | 1 | 0.003 |
| *031 | 1 | 0.003 |
| *033 | 1 | 0.003 |
| *034 | 1 | 0.003 |
| neg | 3 | 0.010 |
| Tel | | |
| KIR2DL4 | | |
| *00102 | 231 | 0.755 |
| *00103 | 25 | 0.082 |
| *00501 | 104 | 0.340 |
| *00503 | 2 | 0.007 |
| *00504 | 2 | 0.007 |
| *006 | 44 | 0.144 |
| *00801 | 35 | 0.114 |
| *011 | 68 | 0.222 |
| *032 | 1 | 0.003 |
| *033 | 1 | 0.003 |
| *034 | 1 | 0.003 |
| KIR3DL1/S1 | | |
| L1*00101 | 30 | 0.098 |
| L1*00501 | 73 | 0.239 |
| L1*00502 | 1 | 0.003 |
| L1*00701 | 49 | 0.160 |
| L1*008 | 1 | 0.003 |
| L1*01502 | 228 | 0.745 |
| L1*01505 | 1 | 0.003 |
| L1*020 | 24 | 0.078 |

TABLE 7-continued

Alleles and their Frequencies of 14 Functional KIR Genes in Southern Chinese Han Population (n = 306)

| | N | Freq. |
|---|---|---|
| L1*02901 | 10 | 0.033 |
| L1*070 | 2 | 0.007 |
| **L1*079** | 1 | 0.003 |
| S1*01301 | 104 | 0.340 |
| S1*078 | 1 | 0.003 |
| **S1*082** | 2 | 0.007 |
| **S1*083** | 1 | 0.003 |
| **S1*084** | 1 | 0.003 |
| **S1*085** | 2 | 0.007 |
| KIR2DL5A | | |
| *001 | 67 | 0.219 |
| *005 | 32 | 0.105 |
| *012 | 4 | 0.013 |
| *022 | 1 | 0.003 |
| neg | 205 | 0.670 |
| KIR2DS4 | | |
| *00101 | 241 | 0.788 |
| *00105 | 1 | 0.003 |
| *00301 | 32 | 0.105 |
| *00401 | 49 | 0.160 |
| *010 | 71 | 0.232 |
| *017 | 1 | 0.003 |
| *018 | 2 | 0.007 |
| neg | 9 | 0.029 |
| KIR2DS1 | | |
| *00201 | 196 | 0.641 |
| *00202 | 2 | 0.007 |
| *006 | 98 | 0.320 |
| neg | 205 | 0.670 |
| KIR3DL2 | | |
| *001 | 35 | 0.114 |
| *002 | 238 | 0.778 |
| *00701 | 62 | 0.203 |
| *00706 | 2 | 0.007 |
| *00707 | 2 | 0.007 |
| *008 | 39 | 0.127 |
| *009 | 22 | 0.072 |
| *010 | 68 | 0.222 |
| *015 | 6 | 0.020 |
| *016 | 3 | 0.010 |
| *021 | 6 | 0.020 |
| *027 | 2 | 0.007 |
| *039 | 19 | 0.062 |
| *083 | 1 | 0.003 |
| *084 | 1 | 0.003 |
| *091 | 3 | 0.010 |
| *093 | 6 | 0.020 |
| *099 | 1 | 0.003 |

Note:
The bold one indicates that the KIR allele is a novel allele.
"neg" means negative.

The foregoing description merely depicts some exemplary embodiments of the present disclosure and therefore is not intended as limiting the scope of the present disclosure. Any equivalent structural transformations made to the disclosure, or any direct or indirect applications of the disclosure on any other related fields based on concepts of the present disclosure, shall all fall in the scope of the present disclosure.

REFERENCES

[1] Vierra-Green C, Roe D, Hou L, et al. Allele-Level Haplotype Frequencies and Pairwise Linkage Disequilibrium for 14 KIR Loci in 506 European-American Individuals. PLoS One, 2012, 7(11): e47491.

[2] Robinson J, Mistry K, McWilliam H, Lopez R, Marsh S G E. IPD—the immuno polymorphism database. Nucleic Acids Res. 2010, 38: D863-869.

[3] McErlean C, Gonzalez A A, Cunningham R, et al. Differential RNA expression of KIR alleles. Immunogenetics, 2010, 62(7): 431-440.

[4] Yawata M, Yawata N, Draghi M, et al. Roles for HLA and KIR polymorphisms in natural killer cell repertoire selection and modulation of effector function. J Exp Med, 2006, 203(3): 633-645.

[5] Pando M J, Gardiner C M, Gleimer M, et al. The protein made from a common allele of KIR3DL1 (3DL1*004) is poorly expressed at cell surfaces due to substitution at positions 86 in Ig domain 0 and 182 in Ig domain 1 J Immunol, 2003, 171(12): 6640-6649.

[6] Bao X, Hou L, Sun A, et al. Distribution of killer cell immunoglobulin-like receptor genes and 2DS4 alleles in the Chinese Han population. Hum Immunol, 2010, 71(3): 289-292.

[7] Lebedeva T V, Ohashi M, Zannelli G, et al. Comprehensive approach to high-resolution KIR typing. Hum Immunol, 2007, 68(9):789-796.

[8] Yan L X, Zhu F M, Jiang K, et al. Diversity of the killer cell immunoglobulin-like receptor gene KIR2DS4 in the Chinese population. Tissue Antigens, 2007, 69(2): 133-138.

[9] Buhler S, Di Cristofaro J, Frassati C, et al. High levels of molecular polymorphism at the KIR2DL4 locus in French and Congolese populations: impact for anthropology and clinical studies. Hum Immunol. 2009, 70(11): 953-959.

[10] Belle L, Hou L, Chen M, et al. Investigation of killer cell immunogloublin-like receptor gene diversity in KIR3DL1 and KIR3DS1 in a transplant population, Tissue Antigens. 2008, 71(5): 434-439.

[11] Hou L, Chen M, Steiner N, et al. Killer cell immunoglobulin-like receptors (KIR) typing by DNA sequencing. Methods Mol Biol, 2012, 882: 431-468.

[12] Meenagh A, Gonzalez A, Sleator C, et al. Investigation of killer cell immunoglobulin-like receptor gene diversity, KIR2DL1 and KIR2DS1. Tissue Antigens. 2008, 72(4): 383-391.

[13] Zhen J, Yu Q. Progress in research on genetic polymorphisms and sequence-based typing of KIR genes. Zhonghua Yi Xue Yi Chuan Xue Za Zhi. 2016, 33(6): 867-870.

What is claimed is:

1. A method for simultaneous sequence-based typing of 14 functional killer cell immunoglobulin-like receptor (KIR) genes comprising:
(i) simultaneously amplifying the complete coding sequence of each functional KIR genes, wherein the KIR3DL3 functional KIR gene is amplified using 3 KIR3DL3 gene-specific primer pairs, the KIR2DL1 functional KIR gene is amplified using 5 KIR2DL1 gene-specific primer pairs, and each of the 12 remaining functional KIR genes are amplified with 4 gene-specific primer pairs, wherein the primers for simultaneously amplifying the complete coding sequence of the 14 KIR genes are SEQ ID NOS: 1-112, wherein all of the primers have the same annealing temperature;

(ii) performing bidirectional sequencing using a plurality of KIR gene-specific specific forward and reverse sequencing primers and determining the nucleotide sequences of exons within each PCR amplicon generated in step (i).

2. The method according to claim 1, wherein each of the PCR amplifications is carried out in a volume of 10 μL containing:

| | |
|---|---|
| 10× PCR Buffer (without MgCl$_2$) | 1.0 μL |
| 2.5 mM dNTP | 0.8 μL, |
| 5.0 mM MgCl$_2$ | 3.0 μL, |
| 10 μM each PCR primer | 0.4 μL, |
| 50 ng/μL to 100 ng/μL genomic DNA | 2.0 μL, |
| 5 U/μL Taq DNA polymerase | 0.1 μL, |
| Add ddH$_2$O to | 10.0 μL. |

3. The method according to claim 1, wherein PCR amplifications are conducted simultaneously under the same thermocycling parameters, and the thermocycling parameters are described below:

| | |
|---|---|
| 95° C. | 3 min; |
| 95° C. | 15 Sec, |
| 68° C. | 15 Sec, |
| 72° C. | 3.5 min, 35 cycles, wherein, each cycle consists of 95° C. (15 Sec), 68° C. (15 Sec) and 72° C. (3.5 Min); |
| 72° C. | 7 min; |
| 4° C. | Hold. |

4. The method according to claim 1, wherein a purification of PCR amplicon is carried out using the purification system described below:

| | |
|---|---|
| 1 U/μL Thermosensitive Alkaline Phosphatase | 1 μL, |
| 20 U/μL Exonuclease I | 0.25 μL, |
| 10× Reaction Buffer | 3 μL, |
| PCR Amplicon | 10 μL. |

5. The method according to claim 1, wherein a purification of PCR amplicon is carried out under the same thermocycling parameters, and the thermocycling parameters are described below:

| | |
|---|---|
| 37° C. | 45 min; |
| 85° C. | 15 min; |
| 4° C. | Hold. |

6. The method according to claim 1, wherein the KIR gene-specific forward and reverse sequencing primers of SEQ ID NOS: 113-342 are provided for bidirectional sequencing of purified PCR amplicons and the nucleotide sequences of each exon of the PCR amplicons are determined.

7. The method according to claim 6, wherein each of the sequencing reactions is carried out in a volume of 10 μL containing:

| | |
|---|---|
| 5× Sequencing Buffer | 2.075 μL, |
| Terminator 3.1 | 0.25 μL, |
| 10 μM Sequencing Primer | 0.32 μL, |
| Purified PCR Amplicon Diluted 1:3 with ddH$_2$O | 2.0 μL, |
| Add ddH$_2$O to | 10.0 μL. |

\* \* \* \* \*

SEQUENCE LISTING

```
<160> NUMBER OF SEQ ID NOS: 342

<210> SEQ ID NO 1
<211> LENGTH: 19
<212> TYPE: DNA
<213> ORGANISM: Artificial sequence
<220> FEATURE:
```

<223> OTHER INFORMATION: Synthetic

<400> SEQUENCE: 1
gttcgggagg ttggatctc                                                    19

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
cacactgcag cccctaccg                                                    19

<210> SEQ ID NO 3
<211> LENGTH: 23
<212> TYPE: DNA
<213> ORGANISM: Artificial sequence
<220> FEATURE:
<223> OTHER INFORMATION: Synthetic

<400> SEQUENCE: 3
tgattctcct gagtctccag agg                                               23

<210> SEQ ID NO 4
<211> LENGTH: 23
<212> TYPE: DNA
<213> ORGANISM: Artificial sequence
<220> FEATURE:
<223> OTHER INFORMATION: Synthetic

<400> SEQUENCE: 4
tggaaggaga agaggcagtt tcc                                               23

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
ctggcaggga cctacagatg c                                                 21

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
ggacagccat gggctttcct c                                                 21

<210> SEQ ID NO 7
<211> LENGTH: 23
<212> TYPE: DNA
<213> ORGANISM: Artificial sequence
<220> FEATURE:
<223> OTHER INFORMATION: Synthetic

<400> SEQUENCE: 7
tcctgattgt gagttcttgg cat                                               23

```
<210> SEQ ID NO 8
<211> LENGTH: 23
<212> TYPE: DNA
<213> ORGANISM: Artificial sequence
<220> FEATURE:
<223> OTHER INFORMATION: Synthetic

<400> SEQUENCE: 8
tgagtcagts agtcgaartg tgc                                               23

<210> SEQ ID NO 9
<211> LENGTH: 23
<212> TYPE: DNA
<213> ORGANISM: Artificial sequence
<220> FEATURE:
<223> OTHER INFORMATION: Synthetic

<400> SEQUENCE: 9
cctcagcacg ttctatggtt act                                               23

<210> SEQ ID NO 10
<211> LENGTH: 23
<212> TYPE: DNA
<213> ORGANISM: Artificial sequence
<220> FEATURE:
<223> OTHER INFORMATION: Synthetic

<400> SEQUENCE: 10
tgtgattgca gcctcaagta gac                                               23

<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
agaggttgga tctgagacgt c                                                 21

<210> SEQ ID NO 12
<211> LENGTH: 21
<212> TYPE: DNA
<213> ORGANISM: Artificial sequence
<220> FEATURE:
<223> OTHER INFORMATION: Synthetic

<400> SEQUENCE: 12
ggaccgatgg agaagttggc t                                                 21

<210> SEQ ID NO 13
<211> LENGTH: 23
<212> TYPE: DNA
<213> ORGANISM: Artificial sequence
<220> FEATURE:
<223> OTHER INFORMATION: Synthetic

<400> SEQUENCE: 13
gaggctacta gagacagagg gac                                               23

<210> SEQ ID NO 14
<211> LENGTH: 21
<212> TYPE: DNA
<213> ORGANISM: Artificial sequence
<220> FEATURE:
<223> OTHER INFORMATION: Synthetic
```

```
<400> SEQUENCE: 14
cccaagcttc gtcttctctc t                                              21

<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
catgccaaca tcatgctgtc                                                20

<210> SEQ ID NO 16
<211> LENGTH: 21
<212> TYPE: DNA
<213> ORGANISM: Artificial sequence
<220> FEATURE:
<223> OTHER INFORMATION: Synthetic

<400> SEQUENCE: 16
tccctgtcct agcctccata c                                              21

<210> SEQ ID NO 17
<211> LENGTH: 23
<212> TYPE: DNA
<213> ORGANISM: Artificial sequence
<220> FEATURE:
<223> OTHER INFORMATION: Synthetic

<400> SEQUENCE: 17
gaagttccac ttgccaagga atg                                            23

<210> SEQ ID NO 18
<211> LENGTH: 21
<212> TYPE: DNA
<213> ORGANISM: Artificial sequence
<220> FEATURE:
<223> OTHER INFORMATION: Synthetic

<400> SEQUENCE: 18
cagctgctgg tacatgggag c                                              21

<210> SEQ ID NO 19
<211> LENGTH: 19
<212> TYPE: DNA
<213> ORGANISM: Artificial sequence
<220> FEATURE:
<223> OTHER INFORMATION: Synthetic

<400> SEQUENCE: 19
ggcygmctgt ctgcacaga                                                 19

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20
ggtttcctgt tgctgctgta g                                              21

<210> SEQ ID NO 21
<211> LENGTH: 23
```

```
<212> TYPE: DNA
<213> ORGANISM: Artificial sequence
<220> FEATURE:
<223> OTHER INFORMATION: Synthetic

<400> SEQUENCE: 21
agagaagagg gagggagaca gat                                              23

<210> SEQ ID NO 22
<211> LENGTH: 19
<212> TYPE: DNA
<213> ORGANISM: Artificial sequence
<220> FEATURE:
<223> OTHER INFORMATION: Synthetic

<400> SEQUENCE: 22
gccatcctgt gccctgatc                                                   19

<210> SEQ ID NO 23
<211> LENGTH: 21
<212> TYPE: DNA
<213> ORGANISM: Artificial sequence
<220> FEATURE:
<223> OTHER INFORMATION: Synthetic

<400> SEQUENCE: 23
cccacctcag gctctcaaag g                                                21

<210> SEQ ID NO 24
<211> LENGTH: 21
<212> TYPE: DNA
<213> ORGANISM: Artificial sequence
<220> FEATURE:
<223> OTHER INFORMATION: Synthetic

<400> SEQUENCE: 24
ggcgtacaat gtcagagctg c                                                21

<210> SEQ ID NO 25
<211> LENGTH: 23
<212> TYPE: DNA
<213> ORGANISM: Artificial sequence
<220> FEATURE:
<223> OTHER INFORMATION: Synthetic

<400> SEQUENCE: 25
actgagaaag caggagaaag ctg                                              23

<210> SEQ ID NO 26
<211> LENGTH: 21
<212> TYPE: DNA
<213> ORGANISM: Artificial sequence
<220> FEATURE:
<223> OTHER INFORMATION: Synthetic

<400> SEQUENCE: 26
ccttcagatt ccagctgctg g                                                21

<210> SEQ ID NO 27
<211> LENGTH: 23
<212> TYPE: DNA
<213> ORGANISM: Artificial sequence
<220> FEATURE:
<223> OTHER INFORMATION: Synthetic

<400> SEQUENCE: 27
```
gtggtcaatg tgtcaactgc acg                                              23

<210> SEQ ID NO 28
<211> LENGTH: 23
<212> TYPE: DNA
<213> ORGANISM: Artificial sequence
<220> FEATURE:
<223> OTHER INFORMATION: Synthetic

<400> SEQUENCE: 28
cacaggctcc aaggattaca atg                                              23

<210> SEQ ID NO 29
<211> LENGTH: 23
<212> TYPE: DNA
<213> ORGANISM: Artificial sequence
<220> FEATURE:
<223> OTHER INFORMATION: Synthetic

<400> SEQUENCE: 29
ctttcttccc catggctgag ttg                                              23

<210> SEQ ID NO 30
<211> LENGTH: 23
<212> TYPE: DNA
<213> ORGANISM: Artificial sequence
<220> FEATURE:
<223> OTHER INFORMATION: Synthetic

<400> SEQUENCE: 30
cttgggcaac aagagtgaaa cgc                                              23

<210> SEQ ID NO 31
<211> LENGTH: 23
<212> TYPE: DNA
<213> ORGANISM: Artificial sequence
<220> FEATURE:
<223> OTHER INFORMATION: Synthetic

<400> SEQUENCE: 31
aacctctacc tccaggattc aag                                              23

<210> SEQ ID NO 32
<211> LENGTH: 23
<212> TYPE: DNA
<213> ORGANISM: Artificial sequence
<220> FEATURE:
<223> OTHER INFORMATION: Synthetic

<400> SEQUENCE: 32
gtaagtggaa gtgtcatgtg cac                                              23

<210> SEQ ID NO 33
<211> LENGTH: 23
<212> TYPE: DNA
<213> ORGANISM: Artificial sequence
<220> FEATURE:
<223> OTHER INFORMATION: Synthetic

<400> SEQUENCE: 33
ccaagaaatg agagacaatc cac                                              23

<210> SEQ ID NO 34
<211> LENGTH: 21
<212> TYPE: DNA
<213> ORGANISM: Artificial sequence

```
<220> FEATURE:
<223> OTHER INFORMATION: Synthetic

<400> SEQUENCE: 34
aggcaccaga tttgtggtgt g                                              21

<210> SEQ ID NO 35
<211> LENGTH: 23
<212> TYPE: DNA
<213> ORGANISM: Artificial sequence
<220> FEATURE:
<223> OTHER INFORMATION: Synthetic

<400> SEQUENCE: 35
tcatagtgaa ggacgygagg tgc                                            23

<210> SEQ ID NO 36
<211> LENGTH: 23
<212> TYPE: DNA
<213> ORGANISM: Artificial sequence
<220> FEATURE:
<223> OTHER INFORMATION: Synthetic

<400> SEQUENCE: 36
agccaatgtg tgaaccacaa tac                                            23

<210> SEQ ID NO 37
<211> LENGTH: 21
<212> TYPE: DNA
<213> ORGANISM: Artificial sequence
<220> FEATURE:
<223> OTHER INFORMATION: Synthetic

<400> SEQUENCE: 37
caggacaagc ccttgctgtc t                                              21

<210> SEQ ID NO 38
<211> LENGTH: 23
<212> TYPE: DNA
<213> ORGANISM: Artificial sequence
<220> FEATURE:
<223> OTHER INFORMATION: Synthetic

<400> SEQUENCE: 38
gacagaaaca agcagtgggt cac                                            23

<210> SEQ ID NO 39
<211> LENGTH: 25
<212> TYPE: DNA
<213> ORGANISM: Artificial sequence
<220> FEATURE:
<223> OTHER INFORMATION: Synthetic

<400> SEQUENCE: 39
catttcctca cctctctcct gtcct                                          25

<210> SEQ ID NO 40
<211> LENGTH: 23
<212> TYPE: DNA
<213> ORGANISM: Artificial sequence
<220> FEATURE:
<223> OTHER INFORMATION: Synthetic

<400> SEQUENCE: 40
aagagcagag gccaaatgca tcg                                            23
```

<210> SEQ ID NO 41
<211> LENGTH: 23
<212> TYPE: DNA
<213> ORGANISM: Artificial sequence
<220> FEATURE:
<223> OTHER INFORMATION: Synthetic

<400> SEQUENCE: 41
cagatgttgt atgtgcttag ctg                                           23

<210> SEQ ID NO 42
<211> LENGTH: 23
<212> TYPE: DNA
<213> ORGANISM: Artificial sequence
<220> FEATURE:
<223> OTHER INFORMATION: Synthetic

<400> SEQUENCE: 42
ggttttgaga cagggctgtt gtc                                           23

<210> SEQ ID NO 43
<211> LENGTH: 23
<212> TYPE: DNA
<213> ORGANISM: Artificial sequence
<220> FEATURE:
<223> OTHER INFORMATION: Synthetic

<400> SEQUENCE: 43
catagtgaag gacgctaggt gta                                           23

<210> SEQ ID NO 44
<211> LENGTH: 21
<212> TYPE: DNA
<213> ORGANISM: Artificial sequence
<220> FEATURE:
<223> OTHER INFORMATION: Synthetic

<400> SEQUENCE: 44
gagccctctg acctgtgacc g                                             21

<210> SEQ ID NO 45
<211> LENGTH: 21
<212> TYPE: DNA
<213> ORGANISM: Artificial sequence
<220> FEATURE:
<223> OTHER INFORMATION: Synthetic

<400> SEQUENCE: 45
gttcctcttc cacccccaca c                                             21

<210> SEQ ID NO 46
<211> LENGTH: 23
<212> TYPE: DNA
<213> ORGANISM: Artificial sequence
<220> FEATURE:
<223> OTHER INFORMATION: Synthetic

<400> SEQUENCE: 46
gagggtttgg aggtgccctg tcg                                           23

<210> SEQ ID NO 47
<211> LENGTH: 23
<212> TYPE: DNA
<213> ORGANISM: Artificial sequence
<220> FEATURE:
<223> OTHER INFORMATION: Synthetic

<400> SEQUENCE: 47
tcctgattgt gagttcttgg cat	23

<210> SEQ ID NO 48
<211> LENGTH: 23
<212> TYPE: DNA
<213> ORGANISM: Artificial sequence
<220> FEATURE:
<223> OTHER INFORMATION: Synthetic

<400> SEQUENCE: 48
gtctcctaga ttccagttac gcc	23

<210> SEQ ID NO 49
<211> LENGTH: 21
<212> TYPE: DNA
<213> ORGANISM: Artificial sequence
<220> FEATURE:
<223> OTHER INFORMATION: Synthetic

<400> SEQUENCE: 49
cgtggaaaag gcaattcccg a	21

<210> SEQ ID NO 50
<211> LENGTH: 21
<212> TYPE: DNA
<213> ORGANISM: Artificial sequence
<220> FEATURE:
<223> OTHER INFORMATION: Synthetic

<400> SEQUENCE: 50
ggaggtggaa cagcacgtgt c	21

<210> SEQ ID NO 51
<211> LENGTH: 23
<212> TYPE: DNA
<213> ORGANISM: Artificial sequence
<220> FEATURE:
<223> OTHER INFORMATION: Synthetic

<400> SEQUENCE: 51
tgagaggttg gatctgagac gtc	23

<210> SEQ ID NO 52
<211> LENGTH: 23
<212> TYPE: DNA
<213> ORGANISM: Artificial sequence
<220> FEATURE:
<223> OTHER INFORMATION: Synthetic

<400> SEQUENCE: 52
acatccaggc tcttatcagc ctt	23

<210> SEQ ID NO 53
<211> LENGTH: 24
<212> TYPE: DNA
<213> ORGANISM: Artificial sequence
<220> FEATURE:
<223> OTHER INFORMATION: Synthetic

<400> SEQUENCE: 53
gcttccatgc ttctgataat tttg	24

<210> SEQ ID NO 54

<211> LENGTH: 21
<212> TYPE: DNA
<213> ORGANISM: Artificial sequence
<220> FEATURE:
<223> OTHER INFORMATION: Synthetic

<400> SEQUENCE: 54
ctctgggtct ctcctgaccg t                                            21

<210> SEQ ID NO 55
<211> LENGTH: 24
<212> TYPE: DNA
<213> ORGANISM: Artificial sequence
<220> FEATURE:
<223> OTHER INFORMATION: Synthetic

<400> SEQUENCE: 55
cattctgctc cgttgttcta tgtc                                         24

<210> SEQ ID NO 56
<211> LENGTH: 23
<212> TYPE: DNA
<213> ORGANISM: Artificial sequence
<220> FEATURE:
<223> OTHER INFORMATION: Synthetic

<400> SEQUENCE: 56
gccagggttg cttcatgacc tat                                          23

<210> SEQ ID NO 57
<211> LENGTH: 23
<212> TYPE: DNA
<213> ORGANISM: Artificial sequence
<220> FEATURE:
<223> OTHER INFORMATION: Synthetic

<400> SEQUENCE: 57
gataggccat ggggaggtaa att                                          23

<210> SEQ ID NO 58
<211> LENGTH: 24
<212> TYPE: DNA
<213> ORGANISM: Artificial sequence
<220> FEATURE:
<223> OTHER INFORMATION: Synthetic

<400> SEQUENCE: 58
gggcagacat gtttatttga aggc                                         24

<210> SEQ ID NO 59
<211> LENGTH: 21
<212> TYPE: DNA
<213> ORGANISM: Artificial sequence
<220> FEATURE:
<223> OTHER INFORMATION: Synthetic

<400> SEQUENCE: 59
tgtaaactgc atgggcaggg a                                            21

<210> SEQ ID NO 60
<211> LENGTH: 23
<212> TYPE: DNA
<213> ORGANISM: Artificial sequence
<220> FEATURE:
<223> OTHER INFORMATION: Synthetic

<400> SEQUENCE: 60
ctctgacctg tgaccatgat cag                                              23

<210> SEQ ID NO 61
<211> LENGTH: 19
<212> TYPE: DNA
<213> ORGANISM: Artificial sequence
<220> FEATURE:
<223> OTHER INFORMATION: Synthetic

<400> SEQUENCE: 61
ctgagcccag cggcaaggc                                                   19

<210> SEQ ID NO 62
<211> LENGTH: 21
<212> TYPE: DNA
<213> ORGANISM: Artificial sequence
<220> FEATURE:
<223> OTHER INFORMATION: Synthetic

<400> SEQUENCE: 62
atccctccct cacaccgagg a                                                21

<210> SEQ ID NO 63
<211> LENGTH: 23
<212> TYPE: DNA
<213> ORGANISM: Artificial sequence
<220> FEATURE:
<223> OTHER INFORMATION: Synthetic

<400> SEQUENCE: 63
taccagggtt ctcctttctc tag                                              23

<210> SEQ ID NO 64
<211> LENGTH: 19
<212> TYPE: DNA
<213> ORGANISM: Artificial sequence
<220> FEATURE:
<223> OTHER INFORMATION: Synthetic

<400> SEQUENCE: 64
aggaagggga ccaggagcg                                                   19

<210> SEQ ID NO 65
<211> LENGTH: 23
<212> TYPE: DNA
<213> ORGANISM: Artificial sequence
<220> FEATURE:
<223> OTHER INFORMATION: Synthetic

<400> SEQUENCE: 65
tgatgttgaa ggaagaggct ctt                                              23

<210> SEQ ID NO 66
<211> LENGTH: 24
<212> TYPE: DNA
<213> ORGANISM: Artificial sequence
<220> FEATURE:
<223> OTHER INFORMATION: Synthetic

<400> SEQUENCE: 66
gatagtctga ggggaggtgg aact                                             24

<210> SEQ ID NO 67
<211> LENGTH: 23
<212> TYPE: DNA

<213> ORGANISM: Artificial sequence
<220> FEATURE:
<223> OTHER INFORMATION: Synthetic

<400> SEQUENCE: 67
accatgtcgc tcatggtcat cat                                           23

<210> SEQ ID NO 68
<211> LENGTH: 21
<212> TYPE: DNA
<213> ORGANISM: Artificial sequence
<220> FEATURE:
<223> OTHER INFORMATION: Synthetic

<400> SEQUENCE: 68
ttgtcctgac caccttgggg t                                             21

<210> SEQ ID NO 69
<211> LENGTH: 23
<212> TYPE: DNA
<213> ORGANISM: Artificial sequence
<220> FEATURE:
<223> OTHER INFORMATION: Synthetic

<400> SEQUENCE: 69
tcagttcata cctcctgcca agg                                           23

<210> SEQ ID NO 70
<211> LENGTH: 21
<212> TYPE: DNA
<213> ORGANISM: Artificial sequence
<220> FEATURE:
<223> OTHER INFORMATION: Synthetic

<400> SEQUENCE: 70
cgtggtcagg agttccagag c                                             21

<210> SEQ ID NO 71
<211> LENGTH: 21
<212> TYPE: DNA
<213> ORGANISM: Artificial sequence
<220> FEATURE:
<223> OTHER INFORMATION: Synthetic

<400> SEQUENCE: 71
ctggactccc agggcccaat g                                             21

<210> SEQ ID NO 72
<211> LENGTH: 21
<212> TYPE: DNA
<213> ORGANISM: Artificial sequence
<220> FEATURE:
<223> OTHER INFORMATION: Synthetic

<400> SEQUENCE: 72
aaggtttcca cctccccagg g                                             21

<210> SEQ ID NO 73
<211> LENGTH: 19
<212> TYPE: DNA
<213> ORGANISM: Artificial sequence
<220> FEATURE:
<223> OTHER INFORMATION: Synthetic

<400> SEQUENCE: 73
gaaagcccgc tgaatcctc                                                19

<210> SEQ ID NO 74
<211> LENGTH: 23
<212> TYPE: DNA
<213> ORGANISM: Artificial sequence
<220> FEATURE:
<223> OTHER INFORMATION: Synthetic

<400> SEQUENCE: 74
gcagaaggct gaaagatagt ctg                                              23

<210> SEQ ID NO 75
<211> LENGTH: 23
<212> TYPE: DNA
<213> ORGANISM: Artificial sequence
<220> FEATURE:
<223> OTHER INFORMATION: Synthetic

<400> SEQUENCE: 75
tgagaacaat ttccaggaag ccg                                              23

<210> SEQ ID NO 76
<211> LENGTH: 21
<212> TYPE: DNA
<213> ORGANISM: Artificial sequence
<220> FEATURE:
<223> OTHER INFORMATION: Synthetic

<400> SEQUENCE: 76
cctttcctgt ggacacttgt c                                                21

<210> SEQ ID NO 77
<211> LENGTH: 23
<212> TYPE: DNA
<213> ORGANISM: Artificial sequence
<220> FEATURE:
<223> OTHER INFORMATION: Synthetic

<400> SEQUENCE: 77
tcctgccaag gattccaatt cga                                              23

<210> SEQ ID NO 78
<211> LENGTH: 23
<212> TYPE: DNA
<213> ORGANISM: Artificial sequence
<220> FEATURE:
<223> OTHER INFORMATION: Synthetic

<400> SEQUENCE: 78
tctgtccatg cttctctcca tcc                                              23

<210> SEQ ID NO 79
<211> LENGTH: 23
<212> TYPE: DNA
<213> ORGANISM: Artificial sequence
<220> FEATURE:
<223> OTHER INFORMATION: Synthetic

<400> SEQUENCE: 79
cttgaagtct caagacagtg ggt                                              23

<210> SEQ ID NO 80
<211> LENGTH: 23
<212> TYPE: DNA
<213> ORGANISM: Artificial sequence
<220> FEATURE:

```
<223> OTHER INFORMATION: Synthetic

<400> SEQUENCE: 80
atgcacttca tactttgagc tag                                              23

<210> SEQ ID NO 81
<211> LENGTH: 23
<212> TYPE: DNA
<213> ORGANISM: Artificial sequence
<220> FEATURE:
<223> OTHER INFORMATION: Synthetic

<400> SEQUENCE: 81
tgatgtkgaa ggaagaggct ctg                                              23

<210> SEQ ID NO 82
<211> LENGTH: 23
<212> TYPE: DNA
<213> ORGANISM: Artificial sequence
<220> FEATURE:
<223> OTHER INFORMATION: Synthetic

<400> SEQUENCE: 82
aggggaggtg gaactgcatg aga                                              23

<210> SEQ ID NO 83
<211> LENGTH: 23
<212> TYPE: DNA
<213> ORGANISM: Artificial sequence
<220> FEATURE:
<223> OTHER INFORMATION: Synthetic

<400> SEQUENCE: 83
cgaggtgtca attctagtga gag                                              23

<210> SEQ ID NO 84
<211> LENGTH: 19
<212> TYPE: DNA
<213> ORGANISM: Artificial sequence
<220> FEATURE:
<223> OTHER INFORMATION: Synthetic

<400> SEQUENCE: 84
taccacaaac atggcagcg                                                   19

<210> SEQ ID NO 85
<211> LENGTH: 21
<212> TYPE: DNA
<213> ORGANISM: Artificial sequence
<220> FEATURE:
<223> OTHER INFORMATION: Synthetic

<400> SEQUENCE: 85
cacccaggtg tggtaggagc c                                                21

<210> SEQ ID NO 86
<211> LENGTH: 23
<212> TYPE: DNA
<213> ORGANISM: Artificial sequence
<220> FEATURE:
<223> OTHER INFORMATION: Synthetic

<400> SEQUENCE: 86
ctctgtgtgg gtgagaggcc atg                                              23
```

```
<210> SEQ ID NO 87
<211> LENGTH: 23
<212> TYPE: DNA
<213> ORGANISM: Artificial sequence
<220> FEATURE:
<223> OTHER INFORMATION: Synthetic

<400> SEQUENCE: 87
gcctgtaata ccactactcg ggt                                           23

<210> SEQ ID NO 88
<211> LENGTH: 21
<212> TYPE: DNA
<213> ORGANISM: Artificial sequence
<220> FEATURE:
<223> OTHER INFORMATION: Synthetic

<400> SEQUENCE: 88
ctaaaacacc tcgccctcat c                                             21

<210> SEQ ID NO 89
<211> LENGTH: 23
<212> TYPE: DNA
<213> ORGANISM: Artificial sequence
<220> FEATURE:
<223> OTHER INFORMATION: Synthetic

<400> SEQUENCE: 89
gctataactg agaaagcagg agg                                           23

<210> SEQ ID NO 90
<211> LENGTH: 23
<212> TYPE: DNA
<213> ORGANISM: Artificial sequence
<220> FEATURE:
<223> OTHER INFORMATION: Synthetic

<400> SEQUENCE: 90
ctggaaaata gtccgaagaa agg                                           23

<210> SEQ ID NO 91
<211> LENGTH: 23
<212> TYPE: DNA
<213> ORGANISM: Artificial sequence
<220> FEATURE:
<223> OTHER INFORMATION: Synthetic

<400> SEQUENCE: 91
tgcaaggtgg caattgtagt cac                                           23

<210> SEQ ID NO 92
<211> LENGTH: 23
<212> TYPE: DNA
<213> ORGANISM: Artificial sequence
<220> FEATURE:
<223> OTHER INFORMATION: Synthetic

<400> SEQUENCE: 92
cgacgatagt gacactgaag agc                                           23

<210> SEQ ID NO 93
<211> LENGTH: 23
<212> TYPE: DNA
<213> ORGANISM: Artificial sequence
<220> FEATURE:
<223> OTHER INFORMATION: Synthetic
```

<400> SEQUENCE: 93
cctcctctct aaggcagtgc ctc                                              23

<210> SEQ ID NO 94
<211> LENGTH: 23
<212> TYPE: DNA
<213> ORGANISM: Artificial sequence
<220> FEATURE:
<223> OTHER INFORMATION: Synthetic

<400> SEQUENCE: 94 cgggtttttcc tcacctgtga cag                                             23

<210> SEQ ID NO 95
<211> LENGTH: 23
<212> TYPE: DNA
<213> ORGANISM: Artificial sequence
<220> FEATURE:
<223> OTHER INFORMATION: Synthetic

<400> SEQUENCE: 95
gacagggcac ctccaaaccc tct                                              23

<210> SEQ ID NO 96
<211> LENGTH: 23
<212> TYPE: DNA
<213> ORGANISM: Artificial sequence
<220> FEATURE:
<223> OTHER INFORMATION: Synthetic

<400> SEQUENCE: 96
attttagccc agtgacatgc acg                                              23

<210> SEQ ID NO 97
<211> LENGTH: 21
<212> TYPE: DNA
<213> ORGANISM: Artificial sequence
<220> FEATURE:
<223> OTHER INFORMATION: Synthetic

<400> SEQUENCE: 97
gcaggagaaa gctgggtctc c                                                21

<210> SEQ ID NO 98
<211> LENGTH: 23
<212> TYPE: DNA
<213> ORGANISM: Artificial sequence
<220> FEATURE:
<223> OTHER INFORMATION: Synthetic

<400> SEQUENCE: 98
ctggttttga gacagggctg ttg                                              23

<210> SEQ ID NO 99
<211> LENGTH: 23
<212> TYPE: DNA
<213> ORGANISM: Artificial sequence
<220> FEATURE:
<223> OTHER INFORMATION: Synthetic

<400> SEQUENCE: 99
acaacatcct gtgtgctgct gaa                                              23

<210> SEQ ID NO 100
<211> LENGTH: 21

```
<212> TYPE: DNA
<213> ORGANISM: Artificial sequence
<220> FEATURE:
<223> OTHER INFORMATION: Synthetic

<400> SEQUENCE: 100 gtcaacccccc tgtgtcgcct g                                             21

<210> SEQ ID NO 101
<211> LENGTH: 23
<212> TYPE: DNA
<213> ORGANISM: Artificial sequence
<220> FEATURE:
<223> OTHER INFORMATION: Synthetic

<400> SEQUENCE: 101
ggaaccacag tcatgaccct gac                                            23

<210> SEQ ID NO 102
<211> LENGTH: 21
<212> TYPE: DNA
<213> ORGANISM: Artificial sequence
<220> FEATURE:
<223> OTHER INFORMATION: Synthetic

<400> SEQUENCE: 102
aaagggtgta ggcgttgctg g                                              21

<210> SEQ ID NO 103
<211> LENGTH: 21
<212> TYPE: DNA
<213> ORGANISM: Artificial sequence
<220> FEATURE:
<223> OTHER INFORMATION: Synthetic

<400> SEQUENCE: 103
tgagccagtc cctcaaggct c                                              21

<210> SEQ ID NO 104
<211> LENGTH: 23
<212> TYPE: DNA
<213> ORGANISM: Artificial sequence
<220> FEATURE:
<223> OTHER INFORMATION: Synthetic

<400> SEQUENCE: 104
gttttactgc tgacagaagg ctg                                            23

<210> SEQ ID NO 105
<211> LENGTH: 23
<212> TYPE: DNA
<213> ORGANISM: Artificial sequence
<220> FEATURE:
<223> OTHER INFORMATION: Synthetic

<400> SEQUENCE: 105
cgaggtgtca attctagtga gag                                            23

<210> SEQ ID NO 106
<211> LENGTH: 20
<212> TYPE: DNA
<213> ORGANISM: Artificial sequence
<220> FEATURE:
<223> OTHER INFORMATION: Synthetic

<400> SEQUENCE: 106
```
cctgtgacca tgatcaccat                                              20

<210> SEQ ID NO 107
<211> LENGTH: 23
<212> TYPE: DNA
<213> ORGANISM: Artificial sequence
<220> FEATURE:
<223> OTHER INFORMATION: Synthetic

<400> SEQUENCE: 107
cagctgacac ttgttgtagg gag                                          23

<210> SEQ ID NO 108
<211> LENGTH: 21
<212> TYPE: DNA
<213> ORGANISM: Artificial sequence
<220> FEATURE:
<223> OTHER INFORMATION: Synthetic

<400> SEQUENCE: 108
agtggcatga tctcggctca g                                            21

<210> SEQ ID NO 109
<211> LENGTH: 19
<212> TYPE: DNA
<213> ORGANISM: Artificial sequence
<220> FEATURE:
<223> OTHER INFORMATION: Synthetic

<400> SEQUENCE: 109
tgatccgccc acctccgct                                               19

<210> SEQ ID NO 110
<211> LENGTH: 21
<212> TYPE: DNA
<213> ORGANISM: Artificial sequence
<220> FEATURE:
<223> OTHER INFORMATION: Synthetic

<400> SEQUENCE: 110
gctgggaggt ttgagccaac g                                            21

<210> SEQ ID NO 111
<211> LENGTH: 23
<212> TYPE: DNA
<213> ORGANISM: Artificial sequence
<220> FEATURE:
<223> OTHER INFORMATION: Synthetic

<400> SEQUENCE: 111
gctataactg agaaagcagg agg                                          23

<210> SEQ ID NO 112
<211> LENGTH: 23
<212> TYPE: DNA
<213> ORGANISM: Artificial sequence
<220> FEATURE:
<223> OTHER INFORMATION: Synthetic

<400> SEQUENCE: 112
gaaggctgaa agctagtctg agg                                          23

<210> SEQ ID NO 113
<211> LENGTH: 19
<212> TYPE: DNA
<213> ORGANISM: Artificial sequence

```
<220> FEATURE:
<223> OTHER INFORMATION: Synthetic

<400> SEQUENCE: 113
cgtgttccgc tcttgagcg                                                19

<210> SEQ ID NO 114
<211> LENGTH: 18
<212> TYPE: DNA
<213> ORGANISM: Artificial sequence
<220> FEATURE:
<223> OTHER INFORMATION: Synthetic

<400> SEQUENCE: 114
cactccctcc ctctattg                                                 18

<210> SEQ ID NO 115
<211> LENGTH: 19
<212> TYPE: DNA
<213> ORGANISM: Artificial sequence
<220> FEATURE:
<223> OTHER INFORMATION: Synthetic

<400> SEQUENCE: 115
ttcttgggtg caggtaggc                                                19

<210> SEQ ID NO 116
<211> LENGTH: 19
<212> TYPE: DNA
<213> ORGANISM: Artificial sequence
<220> FEATURE:
<223> OTHER INFORMATION: Synthetic

<400> SEQUENCE: 116
accctggtcc ccacagaac                                                19

<210> SEQ ID NO 117
<211> LENGTH: 19
<212> TYPE: DNA
<213> ORGANISM: Artificial sequence
<220> FEATURE:
<223> OTHER INFORMATION: Synthetic

<400> SEQUENCE: 117
aaggggaagc ctgactcaa                                                19

<210> SEQ ID NO 118
<211> LENGTH: 20
<212> TYPE: DNA
<213> ORGANISM: Artificial sequence
<220> FEATURE:
<223> OTHER INFORMATION: Synthetic

<400> SEQUENCE: 118
ccaattcctg gatcattcac                                               20

<210> SEQ ID NO 119
<211> LENGTH: 19
<212> TYPE: DNA
<213> ORGANISM: Artificial sequence
<220> FEATURE:
<223> OTHER INFORMATION: Synthetic

<400> SEQUENCE: 119
gttctcagct caggtgaag                                                19
```

<210> SEQ ID NO 120
<211> LENGTH: 23
<212> TYPE: DNA
<213> ORGANISM: Artificial sequence
<220> FEATURE:
<223> OTHER INFORMATION: Synthetic

<400> SEQUENCE: 120
aaacaagcag tgggtcactt gac                                           23

<210> SEQ ID NO 121
<211> LENGTH: 19
<212> TYPE: DNA
<213> ORGANISM: Artificial sequence
<220> FEATURE:
<223> OTHER INFORMATION: Synthetic

<400> SEQUENCE: 121
tttccactga gtggaggac                                                19

<210> SEQ ID NO 122
<211> LENGTH: 19
<212> TYPE: DNA
<213> ORGANISM: Artificial sequence
<220> FEATURE:
<223> OTHER INFORMATION: Synthetic

<400> SEQUENCE: 122
tggagttcgg agatggtgg                                                19

<210> SEQ ID NO 123
<211> LENGTH: 19
<212> TYPE: DNA
<213> ORGANISM: Artificial sequence
<220> FEATURE:
<223> OTHER INFORMATION: Synthetic

<400> SEQUENCE: 123
atgtggttac ctgtcaatc                                                19

<210> SEQ ID NO 124
<211> LENGTH: 18
<212> TYPE: DNA
<213> ORGANISM: Artificial sequence
<220> FEATURE:
<223> OTHER INFORMATION: Synthetic

<400> SEQUENCE: 124
cctgcttccc cacatggc                                                 18

<210> SEQ ID NO 125
<211> LENGTH: 19
<212> TYPE: DNA
<213> ORGANISM: Artificial sequence
<220> FEATURE:
<223> OTHER INFORMATION: Synthetic

<400> SEQUENCE: 125
ctcagccacc tatggtctc                                                19

<210> SEQ ID NO 126
<211> LENGTH: 19
<212> TYPE: DNA
<213> ORGANISM: Artificial sequence
<220> FEATURE:
<223> OTHER INFORMATION: Synthetic

```
<400> SEQUENCE: 126
tctctgtgtg aaaacgcag                                                19

<210> SEQ ID NO 127
<211> LENGTH: 19
<212> TYPE: DNA
<213> ORGANISM: Artificial sequence
<220> FEATURE:
<223> OTHER INFORMATION: Synthetic

<400> SEQUENCE: 127
acagaacagc gaatagcga                                                19

<210> SEQ ID NO 128
<211> LENGTH: 19
<212> TYPE: DNA
<213> ORGANISM: Artificial sequence
<220> FEATURE:
<223> OTHER INFORMATION: Synthetic

<400> SEQUENCE: 128
taagatgcag actcatgcc                                                19

<210> SEQ ID NO 129
<211> LENGTH: 21
<212> TYPE: DNA
<213> ORGANISM: Artificial sequence
<220> FEATURE:
<223> OTHER INFORMATION: Synthetic

<400> SEQUENCE: 129
agaggttgga tctgagacgt c                                             21

<210> SEQ ID NO 130
<211> LENGTH: 19
<212> TYPE: DNA
<213> ORGANISM: Artificial sequence
<220> FEATURE:
<223> OTHER INFORMATION: Synthetic

<400> SEQUENCE: 130
tctccaactc tgggccccg                                                19

<210> SEQ ID NO 131
<211> LENGTH: 19
<212> TYPE: DNA
<213> ORGANISM: Artificial sequence
<220> FEATURE:
<223> OTHER INFORMATION: Synthetic

<400> SEQUENCE: 131
ttcttgggtg caggtaggc                                                19

<210> SEQ ID NO 132
<211> LENGTH: 19
<212> TYPE: DNA
<213> ORGANISM: Artificial sequence
<220> FEATURE:
<223> OTHER INFORMATION: Synthetic

<400> SEQUENCE: 132
cccagtctaa ccctggtcc                                                19

<210> SEQ ID NO 133
```

<210> SEQ ID NO 133
<211> LENGTH: 19
<212> TYPE: DNA
<213> ORGANISM: Artificial sequence
<220> FEATURE:
<223> OTHER INFORMATION: Synthetic

<400> SEQUENCE: 133 aagggaagc ctcactcat                                              19

<210> SEQ ID NO 134
<211> LENGTH: 19
<212> TYPE: DNA
<213> ORGANISM: Artificial sequence
<220> FEATURE:
<223> OTHER INFORMATION: Synthetic

<400> SEQUENCE: 134
ggcccctgtg tctgtcctc                                             19

<210> SEQ ID NO 135
<211> LENGTH: 19
<212> TYPE: DNA
<213> ORGANISM: Artificial sequence
<220> FEATURE:
<223> OTHER INFORMATION: Synthetic

<400> SEQUENCE: 135
gctgtgacaa ggaagatcc                                             19

<210> SEQ ID NO 136
<211> LENGTH: 19
<212> TYPE: DNA
<213> ORGANISM: Artificial sequence
<220> FEATURE:
<223> OTHER INFORMATION: Synthetic

<400> SEQUENCE: 136
aagctcctca gctaaggct                                             19

<210> SEQ ID NO 137
<211> LENGTH: 19
<212> TYPE: DNA
<213> ORGANISM: Artificial sequence
<220> FEATURE:
<223> OTHER INFORMATION: Synthetic

<400> SEQUENCE: 137
atcccaggac tcccagggc                                             19

<210> SEQ ID NO 138
<211> LENGTH: 21
<212> TYPE: DNA
<213> ORGANISM: Artificial sequence
<220> FEATURE:
<223> OTHER INFORMATION: Synthetic

<400> SEQUENCE: 138
ggcgtacaat gtcagagctg c                                          21

<210> SEQ ID NO 139
<211> LENGTH: 19
<212> TYPE: DNA
<213> ORGANISM: Artificial sequence
<220> FEATURE:
<223> OTHER INFORMATION: Synthetic

<400> SEQUENCE: 139
atctgggtgc ttgtcctaa                                              19

<210> SEQ ID NO 140
<211> LENGTH: 21
<212> TYPE: DNA
<213> ORGANISM: Artificial sequence
<220> FEATURE:
<223> OTHER INFORMATION: Synthetic

<400> SEQUENCE: 140
cctctgcttc gtgagactta c                                           21

<210> SEQ ID NO 141
<211> LENGTH: 19
<212> TYPE: DNA
<213> ORGANISM: Artificial sequence
<220> FEATURE:
<223> OTHER INFORMATION: Synthetic

<400> SEQUENCE: 141
cccagaagtg ccctccgag                                              19

<210> SEQ ID NO 142
<211> LENGTH: 19
<212> TYPE: DNA
<213> ORGANISM: Artificial sequence
<220> FEATURE:
<223> OTHER INFORMATION: Synthetic

<400> SEQUENCE: 142
tctctgtgtg aaaacgcag                                              19

<210> SEQ ID NO 143
<211> LENGTH: 19
<212> TYPE: DNA
<213> ORGANISM: Artificial sequence
<220> FEATURE:
<223> OTHER INFORMATION: Synthetic

<400> SEQUENCE: 143
acagaacagc gaatagcga                                              19

<210> SEQ ID NO 144
<211> LENGTH: 23
<212> TYPE: DNA
<213> ORGANISM: Artificial sequence
<220> FEATURE:
<223> OTHER INFORMATION: Synthetic

<400> SEQUENCE: 144
ggctgttgtc tccctagaag acg                                         23

<210> SEQ ID NO 145
<211> LENGTH: 17
<212> TYPE: DNA
<213> ORGANISM: Artificial sequence
<220> FEATURE:
<223> OTHER INFORMATION: Synthetic

<400> SEQUENCE: 145
cygmctgtct gcacaga                                                17

<210> SEQ ID NO 146
<211> LENGTH: 19
<212> TYPE: DNA

```
<213> ORGANISM: Artificial sequence
<220> FEATURE:
<223> OTHER INFORMATION: Synthetic

<400> SEQUENCE: 146
tctccaactc tgggccccg                                                        19

<210> SEQ ID NO 147
<211> LENGTH: 19
<212> TYPE: DNA
<213> ORGANISM: Artificial sequence
<220> FEATURE:
<223> OTHER INFORMATION: Synthetic

<400> SEQUENCE: 147
ttcttgggtg caggtaggc                                                        19

<210> SEQ ID NO 148
<211> LENGTH: 19
<212> TYPE: DNA
<213> ORGANISM: Artificial sequence
<220> FEATURE:
<223> OTHER INFORMATION: Synthetic

<400> SEQUENCE: 148
accctggtcc ccacagaac                                                        19

<210> SEQ ID NO 149
<211> LENGTH: 18
<212> TYPE: DNA
<213> ORGANISM: Artificial sequence
<220> FEATURE:
<223> OTHER INFORMATION: Synthetic

<400> SEQUENCE: 149
cagcaagggg aagcctca                                                         18

<210> SEQ ID NO 150
<211> LENGTH: 19
<212> TYPE: DNA
<213> ORGANISM: Artificial sequence
<220> FEATURE:
<223> OTHER INFORMATION: Synthetic

<400> SEQUENCE: 150
ggcccctgtg tctgtcctc                                                        19

<210> SEQ ID NO 151
<211> LENGTH: 19
<212> TYPE: DNA
<213> ORGANISM: Artificial sequence
<220> FEATURE:
<223> OTHER INFORMATION: Synthetic

<400> SEQUENCE: 151
gagcattagg tcatagagc                                                        19

<210> SEQ ID NO 152
<211> LENGTH: 23
<212> TYPE: DNA
<213> ORGANISM: Artificial sequence
<220> FEATURE:
<223> OTHER INFORMATION: Synthetic

<400> SEQUENCE: 152
ctctctgcat ctgtccatgc ttc                                                   23
```

<210> SEQ ID NO 153
<211> LENGTH: 19
<212> TYPE: DNA
<213> ORGANISM: Artificial sequence
<220> FEATURE:
<223> OTHER INFORMATION: Synthetic

<400> SEQUENCE: 153
tactcaggag tttgaggcc                                               19

<210> SEQ ID NO 154
<211> LENGTH: 21
<212> TYPE: DNA
<213> ORGANISM: Artificial sequence
<220> FEATURE:
<223> OTHER INFORMATION: Synthetic

<400> SEQUENCE: 154
ggcgtacaat gtcagagctg c                                            21

<210> SEQ ID NO 155
<211> LENGTH: 21
<212> TYPE: DNA
<213> ORGANISM: Artificial sequence
<220> FEATURE:
<223> OTHER INFORMATION: Synthetic

<400> SEQUENCE: 155
tctgggtgct tgtcctaaag g                                            21

<210> SEQ ID NO 156
<211> LENGTH: 19
<212> TYPE: DNA
<213> ORGANISM: Artificial sequence
<220> FEATURE:
<223> OTHER INFORMATION: Synthetic

<400> SEQUENCE: 156
caggcaatgg tctgtgagc                                               19

<210> SEQ ID NO 157
<211> LENGTH: 17
<212> TYPE: DNA
<213> ORGANISM: Artificial sequence
<220> FEATURE:
<223> OTHER INFORMATION: Synthetic

<400> SEQUENCE: 157
cttcatcgct ggtgctg                                                 17

<210> SEQ ID NO 158
<211> LENGTH: 19
<212> TYPE: DNA
<213> ORGANISM: Artificial sequence
<220> FEATURE:
<223> OTHER INFORMATION: Synthetic

<400> SEQUENCE: 158
gctgagtgag ggagggtgc                                               19

<210> SEQ ID NO 159
<211> LENGTH: 17
<212> TYPE: DNA
<213> ORGANISM: Artificial sequence
<220> FEATURE:

<223> OTHER INFORMATION: Synthetic

<400> SEQUENCE: 159
cccagcctcg tggctag                                          17

<210> SEQ ID NO 160
<211> LENGTH: 22
<212> TYPE: DNA
<213> ORGANISM: Artificial sequence
<220> FEATURE:
<223> OTHER INFORMATION: Synthetic

<400> SEQUENCE: 160
ggcaggagac aactttggat cw                                    22

<210> SEQ ID NO 161
<211> LENGTH: 23
<212> TYPE: DNA
<213> ORGANISM: Artificial sequence
<220> FEATURE:
<223> OTHER INFORMATION: Synthetic

<400> SEQUENCE: 161
gtggtcaatg tgtcaactgc acg                                   23

<210> SEQ ID NO 162
<211> LENGTH: 19
<212> TYPE: DNA
<213> ORGANISM: Artificial sequence
<220> FEATURE:
<223> OTHER INFORMATION: Synthetic

<400> SEQUENCE: 162
cctgagccac tgggcgcca                                        19

<210> SEQ ID NO 163
<211> LENGTH: 21
<212> TYPE: DNA
<213> ORGANISM: Artificial sequence
<220> FEATURE:
<223> OTHER INFORMATION: Synthetic

<400> SEQUENCE: 163
gagccatgtt ctgaagcaag t                                     21

<210> SEQ ID NO 164
<211> LENGTH: 19
<212> TYPE: DNA
<213> ORGANISM: Artificial sequence
<220> FEATURE:
<223> OTHER INFORMATION: Synthetic

<400> SEQUENCE: 164
caccctctgt gctgcctcc                                        19

<210> SEQ ID NO 165
<211> LENGTH: 19
<212> TYPE: DNA
<213> ORGANISM: Artificial sequence
<220> FEATURE:
<223> OTHER INFORMATION: Synthetic

<400> SEQUENCE: 165
tactcctctc tgaggcggc                                        19

```
<210> SEQ ID NO 166
<211> LENGTH: 19
<212> TYPE: DNA
<213> ORGANISM: Artificial sequence
<220> FEATURE:
<223> OTHER INFORMATION: Synthetic

<400> SEQUENCE: 166
ccagaagctc tgggactca                                                19

<210> SEQ ID NO 167
<211> LENGTH: 19
<212> TYPE: DNA
<213> ORGANISM: Artificial sequence
<220> FEATURE:
<223> OTHER INFORMATION: Synthetic

<400> SEQUENCE: 167
gggaggggag ctgtgacaa                                                19

<210> SEQ ID NO 168
<211> LENGTH: 19
<212> TYPE: DNA
<213> ORGANISM: Artificial sequence
<220> FEATURE:
<223> OTHER INFORMATION: Synthetic

<400> SEQUENCE: 168
gcttctctcc atcatcagc                                                19

<210> SEQ ID NO 169
<211> LENGTH: 19
<212> TYPE: DNA
<213> ORGANISM: Artificial sequence
<220> FEATURE:
<223> OTHER INFORMATION: Synthetic

<400> SEQUENCE: 169
caggcatcct cattgccac                                                19

<210> SEQ ID NO 170
<211> LENGTH: 19
<212> TYPE: DNA
<213> ORGANISM: Artificial sequence
<220> FEATURE:
<223> OTHER INFORMATION: Synthetic

<400> SEQUENCE: 170
tggcaggtgc tgagccaac                                                19

<210> SEQ ID NO 171
<211> LENGTH: 19
<212> TYPE: DNA
<213> ORGANISM: Artificial sequence
<220> FEATURE:
<223> OTHER INFORMATION: Synthetic

<400> SEQUENCE: 171
tcgccagaca cctgcatgc                                                19

<210> SEQ ID NO 172
<211> LENGTH: 14
<212> TYPE: DNA
<213> ORGANISM: Artificial sequence
<220> FEATURE:
<223> OTHER INFORMATION: Synthetic
```

```
<400> SEQUENCE: 172
tttggagcac cagc                                                    14

<210> SEQ ID NO 173
<211> LENGTH: 19
<212> TYPE: DNA
<213> ORGANISM: Artificial sequence
<220> FEATURE:
<223> OTHER INFORMATION: Synthetic

<400> SEQUENCE: 173
gaggacccag aagtgccct                                               19

<210> SEQ ID NO 174
<211> LENGTH: 19
<212> TYPE: DNA
<213> ORGANISM: Artificial sequence
<220> FEATURE:
<223> OTHER INFORMATION: Synthetic

<400> SEQUENCE: 174
ctggagagag ggaaatcct                                               19

<210> SEQ ID NO 175
<211> LENGTH: 21
<212> TYPE: DNA
<213> ORGANISM: Artificial sequence
<220> FEATURE:
<223> OTHER INFORMATION: Synthetic

<400> SEQUENCE: 175
ccagcctcat ggatacagtc t                                            21

<210> SEQ ID NO 176
<211> LENGTH: 23
<212> TYPE: DNA
<213> ORGANISM: Artificial sequence
<220> FEATURE:
<223> OTHER INFORMATION: Synthetic

<400> SEQUENCE: 176
ggaagagtga tgctctaaga tgg                                          23

<210> SEQ ID NO 177
<211> LENGTH: 21
<212> TYPE: DNA
<213> ORGANISM: Artificial sequence
<220> FEATURE:
<223> OTHER INFORMATION: Synthetic

<400> SEQUENCE: 177
ccaaataaca tcctgtgcgc t                                            21

<210> SEQ ID NO 178
<211> LENGTH: 19
<212> TYPE: DNA
<213> ORGANISM: Artificial sequence
<220> FEATURE:
<223> OTHER INFORMATION: Synthetic

<400> SEQUENCE: 178
agatctccat ccccgcact                                               19

<210> SEQ ID NO 179
<211> LENGTH: 19
```

```
<212> TYPE: DNA
<213> ORGANISM: Artificial sequence
<220> FEATURE:
<223> OTHER INFORMATION: Synthetic

<400> SEQUENCE: 179
cagcaagggc ctggctacc                                                19

<210> SEQ ID NO 180
<211> LENGTH: 19
<212> TYPE: DNA
<213> ORGANISM: Artificial sequence
<220> FEATURE:
<223> OTHER INFORMATION: Synthetic

<400> SEQUENCE: 180
gaaaatcccc caccgggct                                                19

<210> SEQ ID NO 181
<211> LENGTH: 21
<212> TYPE: DNA
<213> ORGANISM: Artificial sequence
<220> FEATURE:
<223> OTHER INFORMATION: Synthetic

<400> SEQUENCE: 181
acaagccctt gctgtctgcc t                                             21

<210> SEQ ID NO 182
<211> LENGTH: 19
<212> TYPE: DNA
<213> ORGANISM: Artificial sequence
<220> FEATURE:
<223> OTHER INFORMATION: Synthetic

<400> SEQUENCE: 182
cagatgctct gggattcag                                                19

<210> SEQ ID NO 183
<211> LENGTH: 19
<212> TYPE: DNA
<213> ORGANISM: Artificial sequence
<220> FEATURE:
<223> OTHER INFORMATION: Synthetic

<400> SEQUENCE: 183
caggtgtgag gggagctgt                                                19

<210> SEQ ID NO 184
<211> LENGTH: 22
<212> TYPE: DNA
<213> ORGANISM: Artificial sequence
<220> FEATURE:
<223> OTHER INFORMATION: Synthetic

<400> SEQUENCE: 184
cgggtctgac cactcatagg gt                                            22

<210> SEQ ID NO 185
<211> LENGTH: 22
<212> TYPE: DNA
<213> ORGANISM: Artificial sequence
<220> FEATURE:
<223> OTHER INFORMATION: Synthetic

<400> SEQUENCE: 185
```

```
tcacctctct cctgtcctgt gt                                        22

<210> SEQ ID NO 186
<211> LENGTH: 23
<212> TYPE: DNA
<213> ORGANISM: Artificial sequence
<220> FEATURE:
<223> OTHER INFORMATION: Synthetic

<400> SEQUENCE: 186
tgagccaatg cttgaatcca aga                                       23

<210> SEQ ID NO 187
<211> LENGTH: 23
<212> TYPE: DNA
<213> ORGANISM: Artificial sequence
<220> FEATURE:
<223> OTHER INFORMATION: Synthetic

<400> SEQUENCE: 187
atccataaag aggaactgct ata                                       23

<210> SEQ ID NO 188
<211> LENGTH: 19
<212> TYPE: DNA
<213> ORGANISM: Artificial sequence
<220> FEATURE:
<223> OTHER INFORMATION: Synthetic

<400> SEQUENCE: 188
ccttggtcca gggaccatc                                            19

<210> SEQ ID NO 189
<211> LENGTH: 19
<212> TYPE: DNA
<213> ORGANISM: Artificial sequence
<220> FEATURE:
<223> OTHER INFORMATION: Synthetic

<400> SEQUENCE: 189
cacctacggc ctcccgctg                                            19

<210> SEQ ID NO 190
<211> LENGTH: 21
<212> TYPE: DNA
<213> ORGANISM: Artificial sequence
<220> FEATURE:
<223> OTHER INFORMATION: Synthetic

<400> SEQUENCE: 190
gagggtgctc acattcttca a                                         21

<210> SEQ ID NO 191
<211> LENGTH: 19
<212> TYPE: DNA
<213> ORGANISM: Artificial sequence
<220> FEATURE:
<223> OTHER INFORMATION: Synthetic

<400> SEQUENCE: 191
tgccggggac agaacagtg                                            19

<210> SEQ ID NO 192
<211> LENGTH: 23
<212> TYPE: DNA
<213> ORGANISM: Artificial sequence
```

```
<220> FEATURE:
<223> OTHER INFORMATION: Synthetic

<400> SEQUENCE: 192
ctcaaggcct gactgtggtg ctt                                           23

<210> SEQ ID NO 193
<211> LENGTH: 19
<212> TYPE: DNA
<213> ORGANISM: Artificial sequence
<220> FEATURE:
<223> OTHER INFORMATION: Synthetic

<400> SEQUENCE: 193
ctcccatgat gtggtcaac                                                19

<210> SEQ ID NO 194
<211> LENGTH: 18
<212> TYPE: DNA
<213> ORGANISM: Artificial sequence
<220> FEATURE:
<223> OTHER INFORMATION: Synthetic

<400> SEQUENCE: 194
ctccaacccc acactccc                                                 18

<210> SEQ ID NO 195
<211> LENGTH: 18
<212> TYPE: DNA
<213> ORGANISM: Artificial sequence
<220> FEATURE:
<223> OTHER INFORMATION: Synthetic

<400> SEQUENCE: 195
tcttgggtgc aggtaggc                                                 18

<210> SEQ ID NO 196
<211> LENGTH: 19
<212> TYPE: DNA
<213> ORGANISM: Artificial sequence
<220> FEATURE:
<223> OTHER INFORMATION: Synthetic

<400> SEQUENCE: 196
ctgccaaggg aatgaaagg                                                19

<210> SEQ ID NO 197
<211> LENGTH: 18
<212> TYPE: DNA
<213> ORGANISM: Artificial sequence
<220> FEATURE:
<223> OTHER INFORMATION: Synthetic

<400> SEQUENCE: 197
gtgccatgga tgggatga                                                 18

<210> SEQ ID NO 198
<211> LENGTH: 19
<212> TYPE: DNA
<213> ORGANISM: Artificial sequence
<220> FEATURE:
<223> OTHER INFORMATION: Synthetic

<400> SEQUENCE: 198
caagtcctgg atcattcac                                                19
```

```
<210> SEQ ID NO 199
<211> LENGTH: 19
<212> TYPE: DNA
<213> ORGANISM: Artificial sequence
<220> FEATURE:
<223> OTHER INFORMATION: Synthetic

<400> SEQUENCE: 199
agagcagggg agtgagttc                                                   19

<210> SEQ ID NO 200
<211> LENGTH: 19
<212> TYPE: DNA
<213> ORGANISM: Artificial sequence
<220> FEATURE:
<223> OTHER INFORMATION: Synthetic

<400> SEQUENCE: 200
ggctctagga tcataggac                                                   19

<210> SEQ ID NO 201
<211> LENGTH: 23
<212> TYPE: DNA
<213> ORGANISM: Artificial sequence
<220> FEATURE:
<223> OTHER INFORMATION: Synthetic

<400> SEQUENCE: 201
tcctcaaaga tttccactga gtg                                              23

<210> SEQ ID NO 202
<211> LENGTH: 20
<212> TYPE: DNA
<213> ORGANISM: Artificial sequence
<220> FEATURE:
<223> OTHER INFORMATION: Synthetic

<400> SEQUENCE: 202
gtgagatgct gagtcaacgc                                                  20

<210> SEQ ID NO 203
<211> LENGTH: 20
<212> TYPE: DNA
<213> ORGANISM: Artificial sequence
<220> FEATURE:
<223> OTHER INFORMATION: Synthetic

<400> SEQUENCE: 203
gtggttacct gccaatcaag                                                  20

<210> SEQ ID NO 204
<211> LENGTH: 20
<212> TYPE: DNA
<213> ORGANISM: Artificial sequence
<220> FEATURE:
<223> OTHER INFORMATION: Synthetic

<400> SEQUENCE: 204
tgaggaacac acatccgcgt                                                  20

<210> SEQ ID NO 205
<211> LENGTH: 19
<212> TYPE: DNA
<213> ORGANISM: Artificial sequence
<220> FEATURE:
<223> OTHER INFORMATION: Synthetic
```

<400> SEQUENCE: 205
atggcctccc cctgtttgt                                                          19

<210> SEQ ID NO 206
<211> LENGTH: 19
<212> TYPE: DNA
<213> ORGANISM: Artificial sequence
<220> FEATURE:
<223> OTHER INFORMATION: Synthetic

<400> SEQUENCE: 206
gggaataaga ctagccacg                                                          19

<210> SEQ ID NO 207
<211> LENGTH: 19
<212> TYPE: DNA
<213> ORGANISM: Artificial sequence
<220> FEATURE:
<223> OTHER INFORMATION: Synthetic

<400> SEQUENCE: 207
ctcctcggcc cagcctcgt                                                          19

<210> SEQ ID NO 208
<211> LENGTH: 19
<212> TYPE: DNA
<213> ORGANISM: Artificial sequence
<220> FEATURE:
<223> OTHER INFORMATION: Synthetic

<400> SEQUENCE: 208
tcccctcaag gcctgactg                                                          19

<210> SEQ ID NO 209
<211> LENGTH: 19
<212> TYPE: DNA
<213> ORGANISM: Artificial sequence
<220> FEATURE:
<223> OTHER INFORMATION: Synthetic

<400> SEQUENCE: 209
ataacatcct gtgcgctgc                                                          19

<210> SEQ ID NO 210
<211> LENGTH: 18
<212> TYPE: DNA
<213> ORGANISM: Artificial sequence
<220> FEATURE:
<223> OTHER INFORMATION: Synthetic

<400> SEQUENCE: 210
caactctggg ccccgatc                                                           18

<210> SEQ ID NO 211
<211> LENGTH: 19
<212> TYPE: DNA
<213> ORGANISM: Artificial sequence
<220> FEATURE:
<223> OTHER INFORMATION: Synthetic

<400> SEQUENCE: 211
aagggagtcc tggtttgcc                                                          19

<210> SEQ ID NO 212

```
<211> LENGTH: 19
<212> TYPE: DNA
<213> ORGANISM: Artificial sequence
<220> FEATURE:
<223> OTHER INFORMATION: Synthetic

<400> SEQUENCE: 212
gtcagaaatg tgggccgag                                                  19

<210> SEQ ID NO 213
<211> LENGTH: 19
<212> TYPE: DNA
<213> ORGANISM: Artificial sequence
<220> FEATURE:
<223> OTHER INFORMATION: Synthetic

<400> SEQUENCE: 213
accttctaaa ctcacaacc                                                  19

<210> SEQ ID NO 214
<211> LENGTH: 19
<212> TYPE: DNA
<213> ORGANISM: Artificial sequence
<220> FEATURE:
<223> OTHER INFORMATION: Synthetic

<400> SEQUENCE: 214
cactctgcag cccaatgac                                                  19

<210> SEQ ID NO 215
<211> LENGTH: 19
<212> TYPE: DNA
<213> ORGANISM: Artificial sequence
<220> FEATURE:
<223> OTHER INFORMATION: Synthetic

<400> SEQUENCE: 215
agagcagggg agtgagttc                                                  19

<210> SEQ ID NO 216
<211> LENGTH: 19
<212> TYPE: DNA
<213> ORGANISM: Artificial sequence
<220> FEATURE:
<223> OTHER INFORMATION: Synthetic

<400> SEQUENCE: 216
gaagctcctc agctaaggc                                                  19

<210> SEQ ID NO 217
<211> LENGTH: 19
<212> TYPE: DNA
<213> ORGANISM: Artificial sequence
<220> FEATURE:
<223> OTHER INFORMATION: Synthetic

<400> SEQUENCE: 217
ccagggccca atattagat                                                  19

<210> SEQ ID NO 218
<211> LENGTH: 19
<212> TYPE: DNA
<213> ORGANISM: Artificial sequence
<220> FEATURE:
<223> OTHER INFORMATION: Synthetic

<400> SEQUENCE: 218
```
tgagtcaacg cctgaatcc                                                19

<210> SEQ ID NO 219
<211> LENGTH: 19
<212> TYPE: DNA
<213> ORGANISM: Artificial sequence
<220> FEATURE:
<223> OTHER INFORMATION: Synthetic

<400> SEQUENCE: 219
gccaatcaag aaatgcgag                                                19

<210> SEQ ID NO 220
<211> LENGTH: 19
<212> TYPE: DNA
<213> ORGANISM: Artificial sequence
<220> FEATURE:
<223> OTHER INFORMATION: Synthetic

<400> SEQUENCE: 220
gtcctgcctc tgtggctcc                                                19

<210> SEQ ID NO 221
<211> LENGTH: 19
<212> TYPE: DNA
<213> ORGANISM: Artificial sequence
<220> FEATURE:
<223> OTHER INFORMATION: Synthetic

<400> SEQUENCE: 221
atgaggaccc agaagtgcc                                                19

<210> SEQ ID NO 222
<211> LENGTH: 19
<212> TYPE: DNA
<213> ORGANISM: Artificial sequence
<220> FEATURE:
<223> OTHER INFORMATION: Synthetic

<400> SEQUENCE: 222
cctcctgatg gtcttgttc                                                19

<210> SEQ ID NO 223
<211> LENGTH: 19
<212> TYPE: DNA
<213> ORGANISM: Artificial sequence
<220> FEATURE:
<223> OTHER INFORMATION: Synthetic

<400> SEQUENCE: 223
aggtaggtgc tcctcggcc                                                19

<210> SEQ ID NO 224
<211> LENGTH: 19
<212> TYPE: DNA
<213> ORGANISM: Artificial sequence
<220> FEATURE:
<223> OTHER INFORMATION: Synthetic

<400> SEQUENCE: 224
agaagatccc ctcaaggcc                                                19

<210> SEQ ID NO 225
<211> LENGTH: 19
<212> TYPE: DNA

```
<213> ORGANISM: Artificial sequence
<220> FEATURE:
<223> OTHER INFORMATION: Synthetic

<400> SEQUENCE: 225
cagggagcca aataacatc                                                19

<210> SEQ ID NO 226
<211> LENGTH: 19
<212> TYPE: DNA
<213> ORGANISM: Artificial sequence
<220> FEATURE:
<223> OTHER INFORMATION: Synthetic

<400> SEQUENCE: 226
cgctccctcc ctctattcc                                                19

<210> SEQ ID NO 227
<211> LENGTH: 19
<212> TYPE: DNA
<213> ORGANISM: Artificial sequence
<220> FEATURE:
<223> OTHER INFORMATION: Synthetic

<400> SEQUENCE: 227
gccgagagcc ctgttcttg                                                19

<210> SEQ ID NO 228
<211> LENGTH: 19
<212> TYPE: DNA
<213> ORGANISM: Artificial sequence
<220> FEATURE:
<223> OTHER INFORMATION: Synthetic

<400> SEQUENCE: 228
acaggacttc cctcccgtt                                                19

<210> SEQ ID NO 229
<211> LENGTH: 19
<212> TYPE: DNA
<213> ORGANISM: Artificial sequence
<220> FEATURE:
<223> OTHER INFORMATION: Synthetic

<400> SEQUENCE: 229
agagagacac cttctaaat                                                19

<210> SEQ ID NO 230
<211> LENGTH: 19
<212> TYPE: DNA
<213> ORGANISM: Artificial sequence
<220> FEATURE:
<223> OTHER INFORMATION: Synthetic

<400> SEQUENCE: 230
atcattcact ctgtgtccg                                                19

<210> SEQ ID NO 231
<211> LENGTH: 19
<212> TYPE: DNA
<213> ORGANISM: Artificial sequence
<220> FEATURE:
<223> OTHER INFORMATION: Synthetic

<400> SEQUENCE: 231
aggaagatcc tccataagg                                                19
```

<210> SEQ ID NO 232
<211> LENGTH: 19
<212> TYPE: DNA
<213> ORGANISM: Artificial sequence
<220> FEATURE:
<223> OTHER INFORMATION: Synthetic

<400> SEQUENCE: 232
ggctctagga tcataggac                                                19

<210> SEQ ID NO 233
<211> LENGTH: 19
<212> TYPE: DNA
<213> ORGANISM: Artificial sequence
<220> FEATURE:
<223> OTHER INFORMATION: Synthetic

<400> SEQUENCE: 233
tcccagggcc caatattag                                                19

<210> SEQ ID NO 234
<211> LENGTH: 19
<212> TYPE: DNA
<213> ORGANISM: Artificial sequence
<220> FEATURE:
<223> OTHER INFORMATION: Synthetic

<400> SEQUENCE: 234
cactgagccc tgtgttggg                                                19

<210> SEQ ID NO 235
<211> LENGTH: 21
<212> TYPE: DNA
<213> ORGANISM: Artificial sequence
<220> FEATURE:
<223> OTHER INFORMATION: Synthetic

<400> SEQUENCE: 235
gtgcttgtcc taaagagacg t                                             21

<210> SEQ ID NO 236
<211> LENGTH: 19
<212> TYPE: DNA
<213> ORGANISM: Artificial sequence
<220> FEATURE:
<223> OTHER INFORMATION: Synthetic

<400> SEQUENCE: 236
tgagtggctg cagggacg                                                 19

<210> SEQ ID NO 237
<211> LENGTH: 19
<212> TYPE: DNA
<213> ORGANISM: Artificial sequence
<220> FEATURE:
<223> OTHER INFORMATION: Synthetic

<400> SEQUENCE: 237
gacctcaggc acctatggc                                                19

<210> SEQ ID NO 238
<211> LENGTH: 19
<212> TYPE: DNA
<213> ORGANISM: Artificial sequence
<220> FEATURE:

<223> OTHER INFORMATION: Synthetic

<400> SEQUENCE: 238
gctgagtgag ggagggtgc                                              19

<210> SEQ ID NO 239
<211> LENGTH: 19
<212> TYPE: DNA
<213> ORGANISM: Artificial sequence
<220> FEATURE:
<223> OTHER INFORMATION: Synthetic

<400> SEQUENCE: 239
cggcccagcc tcgtggcta                                              19

<210> SEQ ID NO 240
<211> LENGTH: 23
<212> TYPE: DNA
<213> ORGANISM: Artificial sequence
<220> FEATURE:
<223> OTHER INFORMATION: Synthetic

<400> SEQUENCE: 240
tgtcttgggc ctctgagaag ggg                                         23

<210> SEQ ID NO 241
<211> LENGTH: 18
<212> TYPE: DNA
<213> ORGANISM: Artificial sequence
<220> FEATURE:
<223> OTHER INFORMATION: Synthetic

<400> SEQUENCE: 241
accatgtcgc tcatggtc                                               18

<210> SEQ ID NO 242
<211> LENGTH: 19
<212> TYPE: DNA
<213> ORGANISM: Artificial sequence
<220> FEATURE:
<223> OTHER INFORMATION: Synthetic

<400> SEQUENCE: 242
ggctcatcac tccatctct                                              19

<210> SEQ ID NO 243
<211> LENGTH: 19
<212> TYPE: DNA
<213> ORGANISM: Artificial sequence
<220> FEATURE:
<223> OTHER INFORMATION: Synthetic

<400> SEQUENCE: 243
gaaggggctg gctatcaag                                              19

<210> SEQ ID NO 244
<211> LENGTH: 19
<212> TYPE: DNA
<213> ORGANISM: Artificial sequence
<220> FEATURE:
<223> OTHER INFORMATION: Synthetic

<400> SEQUENCE: 244
gacttccctc ccgtttcag                                              19

```
<210> SEQ ID NO 245
<211> LENGTH: 19
<212> TYPE: DNA
<213> ORGANISM: Artificial sequence
<220> FEATURE:
<223> OTHER INFORMATION: Synthetic

<400> SEQUENCE: 245
agagagacac cttctaaac                                                    19

<210> SEQ ID NO 246
<211> LENGTH: 19
<212> TYPE: DNA
<213> ORGANISM: Artificial sequence
<220> FEATURE:
<223> OTHER INFORMATION: Synthetic

<400> SEQUENCE: 246
cacctgggtc tccaagtcc                                                    19

<210> SEQ ID NO 247
<211> LENGTH: 19
<212> TYPE: DNA
<213> ORGANISM: Artificial sequence
<220> FEATURE:
<223> OTHER INFORMATION: Synthetic

<400> SEQUENCE: 247
agttctcagg tcaggtgtg                                                    19

<210> SEQ ID NO 248
<211> LENGTH: 19
<212> TYPE: DNA
<213> ORGANISM: Artificial sequence
<220> FEATURE:
<223> OTHER INFORMATION: Synthetic

<400> SEQUENCE: 248
ggaagctcct cagctaagg                                                    19

<210> SEQ ID NO 249
<211> LENGTH: 21
<212> TYPE: DNA
<213> ORGANISM: Artificial sequence
<220> FEATURE:
<223> OTHER INFORMATION: Synthetic

<400> SEQUENCE: 249
ctggactccc agggcccaat g                                                 21

<210> SEQ ID NO 250
<211> LENGTH: 19
<212> TYPE: DNA
<213> ORGANISM: Artificial sequence
<220> FEATURE:
<223> OTHER INFORMATION: Synthetic

<400> SEQUENCE: 250
ttccacctcc ccagggttc                                                    19

<210> SEQ ID NO 251
<211> LENGTH: 19
<212> TYPE: DNA
<213> ORGANISM: Artificial sequence
<220> FEATURE:
<223> OTHER INFORMATION: Synthetic
```

<400> SEQUENCE: 251
cgccatttgg gtgcttgtc                                              19

<210> SEQ ID NO 252
<211> LENGTH: 19
<212> TYPE: DNA
<213> ORGANISM: Artificial sequence
<220> FEATURE:
<223> OTHER INFORMATION: Synthetic

<400> SEQUENCE: 252
ggtgaggaac acacatccg                                              19

<210> SEQ ID NO 253
<211> LENGTH: 19
<212> TYPE: DNA
<213> ORGANISM: Artificial sequence
<220> FEATURE:
<223> OTHER INFORMATION: Synthetic

<400> SEQUENCE: 253
agtctgctgt tggcaactg                                              19

<210> SEQ ID NO 254
<211> LENGTH: 19
<212> TYPE: DNA
<213> ORGANISM: Artificial sequence
<220> FEATURE:
<223> OTHER INFORMATION: Synthetic

<400> SEQUENCE: 254
cctcctgatg gtcttgttc                                              19

<210> SEQ ID NO 255
<211> LENGTH: 19
<212> TYPE: DNA
<213> ORGANISM: Artificial sequence
<220> FEATURE:
<223> OTHER INFORMATION: Synthetic

<400> SEQUENCE: 255
ctcggcccag cctcgtggc                                              19

<210> SEQ ID NO 256
<211> LENGTH: 19
<212> TYPE: DNA
<213> ORGANISM: Artificial sequence
<220> FEATURE:
<223> OTHER INFORMATION: Synthetic

<400> SEQUENCE: 256
caactttgga tctgggctc                                              19

<210> SEQ ID NO 257
<211> LENGTH: 19
<212> TYPE: DNA
<213> ORGANISM: Artificial sequence
<220> FEATURE:
<223> OTHER INFORMATION: Synthetic

<400> SEQUENCE: 257
ggcgccaaat aacatcctg                                              19

<210> SEQ ID NO 258
<211> LENGTH: 19

<212> TYPE: DNA
<213> ORGANISM: Artificial sequence
<220> FEATURE:
<223> OTHER INFORMATION: Synthetic

<400> SEQUENCE: 258
gcccagatct ccatccccg                                       19

<210> SEQ ID NO 259
<211> LENGTH: 19
<212> TYPE: DNA
<213> ORGANISM: Artificial sequence
<220> FEATURE:
<223> OTHER INFORMATION: Synthetic

<400> SEQUENCE: 259
ggcactgagk gtgagtttc                                       19

<210> SEQ ID NO 260
<211> LENGTH: 19
<212> TYPE: DNA
<213> ORGANISM: Artificial sequence
<220> FEATURE:
<223> OTHER INFORMATION: Synthetic

<400> SEQUENCE: 260
tgacaggact tccctcccg                                       19

<210> SEQ ID NO 261
<211> LENGTH: 22
<212> TYPE: DNA
<213> ORGANISM: Artificial sequence
<220> FEATURE:
<223> OTHER INFORMATION: Synthetic

<400> SEQUENCE: 261
gacaccttct aaattcacaa ac                                   22

<210> SEQ ID NO 262
<211> LENGTH: 21
<212> TYPE: DNA
<213> ORGANISM: Artificial sequence
<220> FEATURE:
<223> OTHER INFORMATION: Synthetic

<400> SEQUENCE: 262
ctctgcatcc caatgacaat g                                    21

<210> SEQ ID NO 263
<211> LENGTH: 19
<212> TYPE: DNA
<213> ORGANISM: Artificial sequence
<220> FEATURE:
<223> OTHER INFORMATION: Synthetic

<400> SEQUENCE: 263
cctccctgag gaaaatgcc                                       19

<210> SEQ ID NO 264
<211> LENGTH: 19
<212> TYPE: DNA
<213> ORGANISM: Artificial sequence
<220> FEATURE:
<223> OTHER INFORMATION: Synthetic

<400> SEQUENCE: 264

```
tcataggaca tgggacagc                                              19

<210> SEQ ID NO 265
<211> LENGTH: 21
<212> TYPE: DNA
<213> ORGANISM: Artificial sequence
<220> FEATURE:
<223> OTHER INFORMATION: Synthetic

<400> SEQUENCE: 265
cagggcccaa tattagataa c                                           21

<210> SEQ ID NO 266
<211> LENGTH: 21
<212> TYPE: DNA
<213> ORGANISM: Artificial sequence
<220> FEATURE:
<223> OTHER INFORMATION: Synthetic

<400> SEQUENCE: 266
ggagtatctg gagttcggag a                                           21

<210> SEQ ID NO 267
<211> LENGTH: 21
<212> TYPE: DNA
<213> ORGANISM: Artificial sequence
<220> FEATURE:
<223> OTHER INFORMATION: Synthetic

<400> SEQUENCE: 267
ctgtcaatca agaaatgcga g                                           21

<210> SEQ ID NO 268
<211> LENGTH: 19
<212> TYPE: DNA
<213> ORGANISM: Artificial sequence
<220> FEATURE:
<223> OTHER INFORMATION: Synthetic

<400> SEQUENCE: 268
ggaacacaca cccgcgtgc                                              19

<210> SEQ ID NO 269
<211> LENGTH: 21
<212> TYPE: DNA
<213> ORGANISM: Artificial sequence
<220> FEATURE:
<223> OTHER INFORMATION: Synthetic

<400> SEQUENCE: 269
agatagaatg tctgagtctg c                                           21

<210> SEQ ID NO 270
<211> LENGTH: 21
<212> TYPE: DNA
<213> ORGANISM: Artificial sequence
<220> FEATURE:
<223> OTHER INFORMATION: Synthetic

<400> SEQUENCE: 270
acacagtgat ccaattatgc g                                           21

<210> SEQ ID NO 271
<211> LENGTH: 19
<212> TYPE: DNA
<213> ORGANISM: Artificial sequence
```

<220> FEATURE:
<223> OTHER INFORMATION: Synthetic

<400> SEQUENCE: 271
ggtaggtgct cctcggccc                                                19

<210> SEQ ID NO 272
<211> LENGTH: 19
<212> TYPE: DNA
<213> ORGANISM: Artificial sequence
<220> FEATURE:
<223> OTHER INFORMATION: Synthetic

<400> SEQUENCE: 272
atgggagctg gcaacccgg                                                19

<210> SEQ ID NO 273
<211> LENGTH: 19
<212> TYPE: DNA
<213> ORGANISM: Artificial sequence
<220> FEATURE:
<223> OTHER INFORMATION: Synthetic

<400> SEQUENCE: 273
cagggcgcca aataacatc                                                19

<210> SEQ ID NO 274
<211> LENGTH: 19
<212> TYPE: DNA
<213> ORGANISM: Artificial sequence
<220> FEATURE:
<223> OTHER INFORMATION: Synthetic

<400> SEQUENCE: 274
cagatctcca tccccgcac                                                19

<210> SEQ ID NO 275
<211> LENGTH: 19
<212> TYPE: DNA
<213> ORGANISM: Artificial sequence
<220> FEATURE:
<223> OTHER INFORMATION: Synthetic

<400> SEQUENCE: 275
agggcctggc tgccaagac                                                19

<210> SEQ ID NO 276
<211> LENGTH: 19
<212> TYPE: DNA
<213> ORGANISM: Artificial sequence
<220> FEATURE:
<223> OTHER INFORMATION: Synthetic

<400> SEQUENCE: 276
aatgtgggcc gagcatccg                                                19

<210> SEQ ID NO 277
<211> LENGTH: 21
<212> TYPE: DNA
<213> ORGANISM: Artificial sequence
<220> FEATURE:
<223> OTHER INFORMATION: Synthetic

<400> SEQUENCE: 277
ggggagaatc ttctgggcac t                                             21

-continued

<210> SEQ ID NO 278
<211> LENGTH: 19
<212> TYPE: DNA
<213> ORGANISM: Artificial sequence
<220> FEATURE:
<223> OTHER INFORMATION: Synthetic

<400> SEQUENCE: 278
tgatgggacc ctgacggac                                          19

<210> SEQ ID NO 279
<211> LENGTH: 19
<212> TYPE: DNA
<213> ORGANISM: Artificial sequence
<220> FEATURE:
<223> OTHER INFORMATION: Synthetic

<400> SEQUENCE: 279
tggaggcacc tgcaccagg                                          19

<210> SEQ ID NO 280
<211> LENGTH: 19
<212> TYPE: DNA
<213> ORGANISM: Artificial sequence
<220> FEATURE:
<223> OTHER INFORMATION: Synthetic

<400> SEQUENCE: 280
tggtacagac ctcaccaag                                          19

<210> SEQ ID NO 281
<211> LENGTH: 20
<212> TYPE: DNA
<213> ORGANISM: Artificial sequence
<220> FEATURE:
<223> OTHER INFORMATION: Synthetic

<400> SEQUENCE: 281
caggtatgag gggagctatg                                         20

<210> SEQ ID NO 282
<211> LENGTH: 19
<212> TYPE: DNA
<213> ORGANISM: Artificial sequence
<220> FEATURE:
<223> OTHER INFORMATION: Synthetic

<400> SEQUENCE: 282
cctgtctgcc atcctgcgc                                          19

<210> SEQ ID NO 283
<211> LENGTH: 20
<212> TYPE: DNA
<213> ORGANISM: Artificial sequence
<220> FEATURE:
<223> OTHER INFORMATION: Synthetic

<400> SEQUENCE: 283
aagcaccctc atttcctcac                                         20

<210> SEQ ID NO 284
<211> LENGTH: 19
<212> TYPE: DNA
<213> ORGANISM: Artificial sequence
<220> FEATURE:
<223> OTHER INFORMATION: Synthetic -continued

<400> SEQUENCE: 284
caacacttgc atccaaggc                                                19

<210> SEQ ID NO 285
<211> LENGTH: 19
<212> TYPE: DNA
<213> ORGANISM: Artificial sequence
<220> FEATURE:
<223> OTHER INFORMATION: Synthetic

<400> SEQUENCE: 285
cccgccatct gggtgcttg                                                19

<210> SEQ ID NO 286
<211> LENGTH: 19
<212> TYPE: DNA
<213> ORGANISM: Artificial sequence
<220> FEATURE:
<223> OTHER INFORMATION: Synthetic

<400> SEQUENCE: 286
tcctgcttcc ccacatggc                                                19

<210> SEQ ID NO 287
<211> LENGTH: 19
<212> TYPE: DNA
<213> ORGANISM: Artificial sequence
<220> FEATURE:
<223> OTHER INFORMATION: Synthetic

<400> SEQUENCE: 287
ccagaagtgc cctccgagc                                                19

<210> SEQ ID NO 288
<211> LENGTH: 21
<212> TYPE: DNA
<213> ORGANISM: Artificial sequence
<220> FEATURE:
<223> OTHER INFORMATION: Synthetic

<400> SEQUENCE: 288
tgtttgggaa taacactagc c                                             21

<210> SEQ ID NO 289
<211> LENGTH: 19
<212> TYPE: DNA
<213> ORGANISM: Artificial sequence
<220> FEATURE:
<223> OTHER INFORMATION: Synthetic

<400> SEQUENCE: 289
cgtggctagt gttattccc                                                19

<210> SEQ ID NO 290
<211> LENGTH: 19
<212> TYPE: DNA
<213> ORGANISM: Artificial sequence
<220> FEATURE:
<223> OTHER INFORMATION: Synthetic

<400> SEQUENCE: 290
atgggagctg gcaactcgg                                                19

<210> SEQ ID NO 291

<211> LENGTH: 21
<212> TYPE: DNA
<213> ORGANISM: Artificial sequence
<220> FEATURE:
<223> OTHER INFORMATION: Synthetic

<400> SEQUENCE: 291
gccaaataac atcctgtgcg c                                              21

<210> SEQ ID NO 292
<211> LENGTH: 19
<212> TYPE: DNA
<213> ORGANISM: Artificial sequence
<220> FEATURE:
<223> OTHER INFORMATION: Synthetic

<400> SEQUENCE: 292
taggccgaga tctccatcc                                                 19

<210> SEQ ID NO 293
<211> LENGTH: 21
<212> TYPE: DNA
<213> ORGANISM: Artificial sequence
<220> FEATURE:
<223> OTHER INFORMATION: Synthetic

<400> SEQUENCE: 293
gaggctaagt ttaccttcag c                                              21

<210> SEQ ID NO 294
<211> LENGTH: 19
<212> TYPE: DNA
<213> ORGANISM: Artificial sequence
<220> FEATURE:
<223> OTHER INFORMATION: Synthetic

<400> SEQUENCE: 294
gacttccctc ctgtttcag                                                 19

<210> SEQ ID NO 295
<211> LENGTH: 19
<212> TYPE: DNA
<213> ORGANISM: Artificial sequence
<220> FEATURE:
<223> OTHER INFORMATION: Synthetic

<400> SEQUENCE: 295
ggcccagcac tgtggtgcc                                                 19

<210> SEQ ID NO 296
<211> LENGTH: 19
<212> TYPE: DNA
<213> ORGANISM: Artificial sequence
<220> FEATURE:
<223> OTHER INFORMATION: Synthetic

<400> SEQUENCE: 296
gcccatttcc cctgtattc                                                 19

<210> SEQ ID NO 297
<211> LENGTH: 19
<212> TYPE: DNA
<213> ORGANISM: Artificial sequence
<220> FEATURE:
<223> OTHER INFORMATION: Synthetic

<400> SEQUENCE: 297
gagagatgcc ttctaaact                                              19

<210> SEQ ID NO 298
<211> LENGTH: 21
<212> TYPE: DNA
<213> ORGANISM: Artificial sequence
<220> FEATURE:
<223> OTHER INFORMATION: Synthetic

<400> SEQUENCE: 298
tctccataag aatcccacgc t                                           21

<210> SEQ ID NO 299
<211> LENGTH: 19
<212> TYPE: DNA
<213> ORGANISM: Artificial sequence
<220> FEATURE:
<223> OTHER INFORMATION: Synthetic

<400> SEQUENCE: 299
cctccctgag gaaactgcc                                              19

<210> SEQ ID NO 300
<211> LENGTH: 19
<212> TYPE: DNA
<213> ORGANISM: Artificial sequence
<220> FEATURE:
<223> OTHER INFORMATION: Synthetic

<400> SEQUENCE: 300
gaaagagccg aagcatctg                                              19

<210> SEQ ID NO 301
<211> LENGTH: 21
<212> TYPE: DNA
<213> ORGANISM: Artificial sequence
<220> FEATURE:
<223> OTHER INFORMATION: Synthetic

<400> SEQUENCE: 301
caacctcaaa gatttccatt g                                           21

<210> SEQ ID NO 302
<211> LENGTH: 19
<212> TYPE: DNA
<213> ORGANISM: Artificial sequence
<220> FEATURE:
<223> OTHER INFORMATION: Synthetic

<400> SEQUENCE: 302
caacacttgc atccaaggc                                              19

<210> SEQ ID NO 303
<211> LENGTH: 21
<212> TYPE: DNA
<213> ORGANISM: Artificial sequence
<220> FEATURE:
<223> OTHER INFORMATION: Synthetic

<400> SEQUENCE: 303
gagatgttcc atgtggttac c                                           21

<210> SEQ ID NO 304
<211> LENGTH: 19
<212> TYPE: DNA

```
<213> ORGANISM: Artificial sequence
<220> FEATURE:
<223> OTHER INFORMATION: Synthetic

<400> SEQUENCE: 304
ggaacacaca cccgcgtgc                                                  19

<210> SEQ ID NO 305
<211> LENGTH: 19
<212> TYPE: DNA
<213> ORGANISM: Artificial sequence
<220> FEATURE:
<223> OTHER INFORMATION: Synthetic

<400> SEQUENCE: 305
tctgagtctg gatgttggc                                                  19

<210> SEQ ID NO 306
<211> LENGTH: 21
<212> TYPE: DNA
<213> ORGANISM: Artificial sequence
<220> FEATURE:
<223> OTHER INFORMATION: Synthetic

<400> SEQUENCE: 306
gggtcttgtt catcagagtc c                                               21

<210> SEQ ID NO 307
<211> LENGTH: 19
<212> TYPE: DNA
<213> ORGANISM: Artificial sequence
<220> FEATURE:
<223> OTHER INFORMATION: Synthetic

<400> SEQUENCE: 307
cctcggccca gcctcacgg                                                  19

<210> SEQ ID NO 308
<211> LENGTH: 19
<212> TYPE: DNA
<213> ORGANISM: Artificial sequence
<220> FEATURE:
<223> OTHER INFORMATION: Synthetic

<400> SEQUENCE: 308
gactgtggtg ctcgtgggc                                                  19

<210> SEQ ID NO 309
<211> LENGTH: 23
<212> TYPE: DNA
<213> ORGANISM: Artificial sequence
<220> FEATURE:
<223> OTHER INFORMATION: Synthetic

<400> SEQUENCE: 309
acaacatcct gtgtgctgct gaa                                             23

<210> SEQ ID NO 310
<211> LENGTH: 19
<212> TYPE: DNA
<213> ORGANISM: Artificial sequence
<220> FEATURE:
<223> OTHER INFORMATION: Synthetic

<400> SEQUENCE: 310
tccctccctc gattccctt                                                  19
```

<210> SEQ ID NO 311
<211> LENGTH: 19
<212> TYPE: DNA
<213> ORGANISM: Artificial sequence
<220> FEATURE:
<223> OTHER INFORMATION: Synthetic

<400> SEQUENCE: 311
gatgtacaga tggatcatc                                              19

<210> SEQ ID NO 312
<211> LENGTH: 21
<212> TYPE: DNA
<213> ORGANISM: Artificial sequence
<220> FEATURE:
<223> OTHER INFORMATION: Synthetic

<400> SEQUENCE: 312
gtcaaccccc tgtgtcgcct g                                           21

<210> SEQ ID NO 313
<211> LENGTH: 19
<212> TYPE: DNA
<213> ORGANISM: Artificial sequence
<220> FEATURE:
<223> OTHER INFORMATION: Synthetic

<400> SEQUENCE: 313
gctccacatc ctcctctct                                              19

<210> SEQ ID NO 314
<211> LENGTH: 19
<212> TYPE: DNA
<213> ORGANISM: Artificial sequence
<220> FEATURE:
<223> OTHER INFORMATION: Synthetic

<400> SEQUENCE: 314
atcccccttt accccaaat                                              19

<210> SEQ ID NO 315
<211> LENGTH: 21
<212> TYPE: DNA
<213> ORGANISM: Artificial sequence
<220> FEATURE:
<223> OTHER INFORMATION: Synthetic

<400> SEQUENCE: 315
gggaagcctc acttatttca g                                           21

<210> SEQ ID NO 316
<211> LENGTH: 19
<212> TYPE: DNA
<213> ORGANISM: Artificial sequence
<220> FEATURE:
<223> OTHER INFORMATION: Synthetic

<400> SEQUENCE: 316
acctggggct tccagtcct                                              19

<210> SEQ ID NO 317
<211> LENGTH: 19
<212> TYPE: DNA
<213> ORGANISM: Artificial sequence
<220> FEATURE:

<223> OTHER INFORMATION: Synthetic

<400> SEQUENCE: 317
gagagctgtg acaasgaag                                    19

<210> SEQ ID NO 318
<211> LENGTH: 19
<212> TYPE: DNA
<213> ORGANISM: Artificial sequence
<220> FEATURE:
<223> OTHER INFORMATION: Synthetic

<400> SEQUENCE: 318
gcaggaagct cctcagcta                                    19

<210> SEQ ID NO 319
<211> LENGTH: 19
<212> TYPE: DNA
<213> ORGANISM: Artificial sequence
<220> FEATURE:
<223> OTHER INFORMATION: Synthetic

<400> SEQUENCE: 319
gtgagacaat tcatataga                                    19

<210> SEQ ID NO 320
<211> LENGTH: 19
<212> TYPE: DNA
<213> ORGANISM: Artificial sequence
<220> FEATURE:
<223> OTHER INFORMATION: Synthetic

<400> SEQUENCE: 320
tgcttcccca catggccct                                    19

<210> SEQ ID NO 321
<211> LENGTH: 19
<212> TYPE: DNA
<213> ORGANISM: Artificial sequence
<220> FEATURE:
<223> OTHER INFORMATION: Synthetic

<400> SEQUENCE: 321
gacctcaggc acctatggc                                    19

<210> SEQ ID NO 322
<211> LENGTH: 19
<212> TYPE: DNA
<213> ORGANISM: Artificial sequence
<220> FEATURE:
<223> OTHER INFORMATION: Synthetic

<400> SEQUENCE: 322
gagtgaggga gggtgctca                                    19

<210> SEQ ID NO 323
<211> LENGTH: 19
<212> TYPE: DNA
<213> ORGANISM: Artificial sequence
<220> FEATURE:
<223> OTHER INFORMATION: Synthetic

<400> SEQUENCE: 323
crtggctagt cttattccc                                    19

```
<210> SEQ ID NO 324
<211> LENGTH: 19
<212> TYPE: DNA
<213> ORGANISM: Artificial sequence
<220> FEATURE:
<223> OTHER INFORMATION: Synthetic

<400> SEQUENCE: 324
ccctagaaga tcccatcaa                                                  19

<210> SEQ ID NO 325
<211> LENGTH: 19
<212> TYPE: DNA
<213> ORGANISM: Artificial sequence
<220> FEATURE:
<223> OTHER INFORMATION: Synthetic

<400> SEQUENCE: 325
aagccatgct ccgctcttg                                                  19

<210> SEQ ID NO 326
<211> LENGTH: 19
<212> TYPE: DNA
<213> ORGANISM: Artificial sequence
<220> FEATURE:
<223> OTHER INFORMATION: Synthetic

<400> SEQUENCE: 326
cagatctcca tccccgcac                                                  19

<210> SEQ ID NO 327
<211> LENGTH: 18
<212> TYPE: DNA
<213> ORGANISM: Artificial sequence
<220> FEATURE:
<223> OTHER INFORMATION: Synthetic

<400> SEQUENCE: 327
agtgggggca gcagggtg                                                   18

<210> SEQ ID NO 328
<211> LENGTH: 19
<212> TYPE: DNA
<213> ORGANISM: Artificial sequence
<220> FEATURE:
<223> OTHER INFORMATION: Synthetic

<400> SEQUENCE: 328
aatgtgggcc gagcatccg                                                  19

<210> SEQ ID NO 329
<211> LENGTH: 21
<212> TYPE: DNA
<213> ORGANISM: Artificial sequence
<220> FEATURE:
<223> OTHER INFORMATION: Synthetic

<400> SEQUENCE: 329
ggggagaatc ttctgggcac t                                               21

<210> SEQ ID NO 330
<211> LENGTH: 19
<212> TYPE: DNA
<213> ORGANISM: Artificial sequence
<220> FEATURE:
<223> OTHER INFORMATION: Synthetic
```

<400> SEQUENCE: 330
tgatgggacc ctgacggac                                              19

<210> SEQ ID NO 331
<211> LENGTH: 19
<212> TYPE: DNA
<213> ORGANISM: Artificial sequence
<220> FEATURE:
<223> OTHER INFORMATION: Synthetic

<400> SEQUENCE: 331
ggagagagac agacacggg                                              19

<210> SEQ ID NO 332
<211> LENGTH: 19
<212> TYPE: DNA
<213> ORGANISM: Artificial sequence
<220> FEATURE:
<223> OTHER INFORMATION: Synthetic

<400> SEQUENCE: 332
tggtacagac ctcaccaag                                              19

<210> SEQ ID NO 333
<211> LENGTH: 19
<212> TYPE: DNA
<213> ORGANISM: Artificial sequence
<220> FEATURE:
<223> OTHER INFORMATION: Synthetic

<400> SEQUENCE: 333
caggtgtgag gggagctgt                                              19

<210> SEQ ID NO 334
<211> LENGTH: 19
<212> TYPE: DNA
<213> ORGANISM: Artificial sequence
<220> FEATURE:
<223> OTHER INFORMATION: Synthetic

<400> SEQUENCE: 334
cctgtctgcc atcctgcgc                                              19

<210> SEQ ID NO 335
<211> LENGTH: 21
<212> TYPE: DNA
<213> ORGANISM: Artificial sequence
<220> FEATURE:
<223> OTHER INFORMATION: Synthetic

<400> SEQUENCE: 335
tcaagacagt gggcatcgca c                                           21

<210> SEQ ID NO 336
<211> LENGTH: 21
<212> TYPE: DNA
<213> ORGANISM: Artificial sequence
<220> FEATURE:
<223> OTHER INFORMATION: Synthetic

<400> SEQUENCE: 336
gggaggtttg agccaacgct t                                           21

<210> SEQ ID NO 337
<211> LENGTH: 21

```
<212> TYPE: DNA
<213> ORGANISM: Artificial sequence
<220> FEATURE:
<223> OTHER INFORMATION: Synthetic

<400> SEQUENCE: 337
cgctgtatgt ggttacctgt g                                              21

<210> SEQ ID NO 338
<211> LENGTH: 19
<212> TYPE: DNA
<213> ORGANISM: Artificial sequence
<220> FEATURE:
<223> OTHER INFORMATION: Synthetic

<400> SEQUENCE: 338
ggtgaggaac acacacccg                                                 19

<210> SEQ ID NO 339
<211> LENGTH: 19
<212> TYPE: DNA
<213> ORGANISM: Artificial sequence
<220> FEATURE:
<223> OTHER INFORMATION: Synthetic

<400> SEQUENCE: 339
ccagaagtgc cctccgagc                                                 19

<210> SEQ ID NO 340
<211> LENGTH: 19
<212> TYPE: DNA
<213> ORGANISM: Artificial sequence
<220> FEATURE:
<223> OTHER INFORMATION: Synthetic

<400> SEQUENCE: 340
gctgagtgag ggagggtgc                                                 19

<210> SEQ ID NO 341
<211> LENGTH: 19
<212> TYPE: DNA
<213> ORGANISM: Artificial sequence
<220> FEATURE:
<223> OTHER INFORMATION: Synthetic

<400> SEQUENCE: 341
cgtggctagt gttattccc                                                 19

<210> SEQ ID NO 342
<211> LENGTH: 19
<212> TYPE: DNA
<213> ORGANISM: Artificial sequence
<220> FEATURE:
<223> OTHER INFORMATION: Synthetic

<400> SEQUENCE: 342
ggcctctgag aagggcgag                                                 19
```